(12) United States Patent
Bosch et al.

(10) Patent No.: US 6,780,408 B1
(45) Date of Patent: Aug. 24, 2004

(54) **GENES ENCODING HYBRID *BACILLUS THURINGIENSIS* TOXINS**

(75) Inventors: Hendrik Jan Bosch, Utrecht (NL); Willem Johannes Stiekema, Wageningen (NL)

(73) Assignee: Syngenta Participations AG, Schwaarzwaldallee (CH)

( * ) Notice: Subject to any disclaimer, the term of this patent is extended or adjusted under 35 U.S.C. 154(b) by 629 days.

(21) Appl. No.: 09/668,650

(22) Filed: Sep. 22, 2000

Related U.S. Application Data

(60) Division of application No. 09/001,982, filed on Dec. 31, 1997, now Pat. No. 6,204,246, which is a continuation-in-part of application No. 08/602,737, filed as application No. PCT/EP94/02909 on Sep. 1, 1994, now Pat. No. 5,736,131.

(30) Foreign Application Priority Data

Sep. 2, 1993 (GB) .............................................. 9318207

(51) Int. Cl.[7] ...................... A01N 63/00; C12N 15/32; C12N 15/63; C12N 1/00; C12N 5/10; C12P 21/02; A01H 5/00; A01H 5/10

(52) U.S. Cl. ................ 424/93.2; 424/93.461; 435/320.1; 435/69.7; 435/69.1; 435/252.3; 435/254.11; 435/419; 435/418; 536/23.71; 800/302

(58) Field of Search .................... 536/23.71; 435/320.1, 435/418–419, 252.3, 252.33, 254.11, 69.1, 69.7, 252.31; 424/93.2, 93.461, 93.1; 800/302

(56) References Cited

U.S. PATENT DOCUMENTS

| | | |
|---|---|---|
| 5,508,264 A | 4/1996 | Bradfish et al. .............. 514/12 |
| 5,593,881 A | 1/1997 | Thompson et al. ......... 435/418 |
| 5,736,131 A | 4/1998 | Bosch et al. ................. 800/300 |

FOREIGN PATENT DOCUMENTS

| | | |
|---|---|---|
| EP | 0228838 | 4/1992 |
| WO | WO91/01087 | 2/1991 |
| WO | WO95/30753 | 11/1995 |

OTHER PUBLICATIONS

Honee et al., *Molecular Microbiology*, 5(11):2799–2806 (1991).
Nakamura et al., *Agric. Biol. Chem.*, 54(3):715–724 (1990).
Ge et al., *Proc. Nat. Acad. Sci.*, USA 86:4037–4041 (1989).
Bosch et al., *Bio/technology* 12:915–918 (1994).
Visser et al., Domain–function studies of Bacillus thuringiensis crystal proteins: a genetic approach in Bacillus thuringiensis, an environmental biopesticide: theory and practice. (eds, Entwistle et al.) Chicester: Wiley & Sons (1993) p 71–86.
Schnepf et al., *J. Biol Chem.*, 265(34):20923–20930 (1990).
Raymond et al., *Mol. Microbiology* 4(11):1967–1973 (1990).
Li et al., Nature, 353:815–821, Oct. 31, 1991.
DeMaagd et al., Applied and Environmental Microbiology, 62(5):1537–1543, May 1996.

*Primary Examiner*—Gabriele Bugaisky
(74) *Attorney, Agent, or Firm*—Syngenta Biotechnology, Inc.

(57) ABSTRACT

The present invention provides, inter alia, a B.t. hybrid toxin fragment comprising at its C-terminus domain III of a first Cry protein, or a part of said domain or a protein substantially similar to said domain; and comprising at its N-terminus the N-terminal region of a second Cry protein, or a part of said region or a protein substantially similar to said region.

29 Claims, 7 Drawing Sheets

FIG. 3

CryIC-CryIE HYBRIDS

```
                                        Domain     F26
              F59  F71                  II↔  →III   ↓
               ↓    ↓                              RSAILTNIQPERINQ

FIG. 6A

```
              1520      1530      1540      1550      1560      1570
               *         *         *         *         *         *
CRYIGTOX   AAAAGTCTGGCTCGTAACAATACCATTAATCCAGATAGAATTACACAGATACCATTGACG
            :::       :::  ::   :::::  :::  :::::::  ::::::::  ::  :::::: ::    :
CRYICTOX   CGTAGTGCAACTCTTACAAATACAATTGATCCAGAGAGAATTAATCAAATACCTTTAGTG
                                             |         |         |
Hybrid HK28-                               -12       -1        -24
```

FIG. 6B

```
              490       500       510       520       530
               *         *         #         *         *         *
CRYIGTOX   GGLRQVASNRRSSLVMYGWTHKSLARNNTINPDRITQIPLTKVDTRGTGV
            :::       :       ::: :     ::: : ::  ::::  :                :
CRYICTOX   TG-------------VVFSWTHRSATLTNTIDPERINQIPLVKGFRVWGGT
                                        |   |   |
Hybrid HK28-                           -12 -1  -24
```

GENES ENCODING HYBRID BACILLUS THURINGIENSIS TOXINS

This application is a division of application Ser. No. 09/001,982, filed Dec. 31, 1997, U.S. Pat No. 6,204,246 which is a continuation-in-part of application Ser. No. 08/602,737, filed Feb. 21, 1996, now U.S. Pat. No. 5,736, 131, which is a §371 of international application no. PCT/EP94/02909, filed Sep. 1, 1994. The aforementioned applications are incorporated herein by reference.

FIELD OF THE INVENTION

The present invention relates to hybrid toxin fragments, and toxins comprising them, derived from *Bacillus thuringiensis* insecticidal crystal proteins.

BACKGROUND OF THE INVENTION

*Bacillus thuringiensis* (hereinafter B.t.) is capable of producing proteins that accumulate intra-cellularly as crystals. These crystal proteins are toxic to a number of insect larvae. Based on sequence homology and insecticidal specificity, crystal proteins have been categorized into different classes. Best studied are the CryI class of proteins, which are produced as 140 kDa protoxins and are active towards lepidopterans.

To some extent, the mode of action of crystal proteins has been elucidated. After oral uptake, the crystals dissolve in the alkaline environment of the larval midgul The solubilized proteins are subsequently processed by midgut proteinases to a proteinase-resistant toxic fragment of about 65 kDa, which binds to receptors on epithelial cells of the insect midgut and penetrates the cell membrane. This eventually leads to bursting of the cells and death of the larvae.

The activity spectrum of a particular crystal protein is to a large extent determined by the occurrence of receptors on the midgut epithelial cells of susceptible insects. The activity spectrum is co-determined by the efficiency of solubilization of the crystal protein and its proteolytic activation in vivo.

The importance of the binding of the crystal protein to midgut epithelial receptors is further demonstrated where insects have developed resistance to one of the crystal proteins, such that the binding of crystal proteins to midgut epithelial cells in resistant insects is significantly reduced.

Toxic fragments of crystal proteins are thought to be composed of three distinct structural domains. Domain I, the most N-terminal domain, consists of 7 α-helices. Domain II comprises 3 β-sheets. Domain III, the most C-terminal domain, folds into a β-sandwich. If projected on CryI sequences, domain I runs from about amino acid residues 28 to 260, domain II from about 260 to 5 460, and domain m from about 460 to 600.

DESCRIPTION OF THE INVENTION

The present invention concerns hybrid crystal proteins particularly, though not exclusively, involving CryIC together with CryIE, CryIA, or CryIG. The nucleotide sequence of the CryIC gene from B.t. sub. sp. *entomocidus* 60.5 is given in SEQ ID NO:1, and the corresponding amino acid sequence of the protein encoded by said nucleotide sequence is given in SEQ ID NO:2. The Id nucleotide sequence of the CryIE gene from B.t. sub. sp. *kenyae* 4FI is given in SEQ ID No.3, and the corresponding amino acid sequence of the protein encoded by said nucleotide sequence is given in SEQ ID NO:4. The nucleotide sequence of a B.t. CryIG gene is given in SEQ ID NO:9, and the corresponding amino acid sequence of the protein encoded by said nucleotide sequence is given in SEQ ID NO:10. These proteins are toxic to lepidopterans, but within this order of insects, each protein has different specificity. CryIC, for example, is particularly active against *S. exigua* and *M. brassicae*.

According to the present invention, there is provided an isolated B.t. hybrid toxin fragment comprising at its C-terminus domain III of a first Cry protein, or a part of said domain or a protein substantially similar to said domain; and comprising at its N-terminus the N-terminal region of a second Cry protein, or a part of said region or a protein substantially similar to said region. For example, a preferred B.t. hybrid toxin fragment according to the present invention comprises at its C-terminus domain III of a first Cry protein and comprises at its N-terminus domains I and II of a second Cry protein. A preferred fragment is one that does not bind to the CryIC binding site in an insect gut when it comprises at its C-terminus domain III of CryIC, or a part of said domain or a protein substantially similar to said domain; or one that does not bind to a CryIA binding site when it comprises at its C-terminus domain m of CryIA, or a part of said domain or a protein substantially similar to said domain.

In the context of the present invention, "substantially similar" means a pure protein having an amino acid sequence that is at least 75% similar to the sequence of a protein according to the invention. It is preferred that the degree of similarity is at least 85%, more preferred that the degree of similarity is at least 90%, and still more preferred that the degree of similarity is at least 95%. In the context of the present invention, two amino acid sequences with at least 75%, 85%, 90%, or 95% similarity to each other have at least 75%, 85%, 90%, or 95% identical or conservatively replaced amino acid residues in a like position when aligned optimally allowing for up to 6 gaps, with the proviso that, with respect to the gaps, a total not more than 15 amino acid residues are affected. For the purpose of the present invention, conservative replacements may be made between amino acids within the following groups:

(i) Serine and Threonine;
(ii) Glutamic acid and Aspartic acid;
(iii) Arginine and Lysine;
(iv) Asparagine and Glutamine;
(v) Isoleucine, Leucine, Valine, and Methionine;
(vi) Phenylalanine, Tyrosine, and Tryptophan; and
(vii) Alanine and Glycine, with the proviso that in SEQ ID NO:6, Ser and Tyr are conservative replacements at position 620, and Ala and Glu are conservative replacements at position 618; and that SEQ ID NO:8, Ser and Tyr are conservative replacements at position 627, and Ala and Glu are conservative replacements at position 625.

In the context of the present invention, "part" of a protein means a peptide comprised by said protein and having at least 80% of the consecutive sequence thereof.

In the context of the present invention, "binding site" means a site on a molecule wherein the binding between site and toxin is reversible such that the Ka between site and toxin is in the order of at least $10^4 dm^3$ $mole^{-1}$.

The toxin fragment may comprise at its N-terminus the N-terminal region of any insecticidal protein from B.t. being commonly known as "Cry" or "Cyt", including: CryIA(a), CryIA(b) CryIA(c), CryIB, CryIC, CryID, CryIE, CryIF, CryIG, CryIH, CryIIA, CryIB, CryIIC, CryIIIA, CryIIIB, CryIIIB(b), CryIVA, CryrVB CryIVC, CryIVD, CYTA, CryX1(IIIC), CryX2(MD), CryX3, CryV, and CryX4, or a part of said region or a protein substantially similar to said region. The toxin fragment may comprise at its C-terminus domain m of CryIC, or a part of said domain or a protein substantially similar to said domain.

Thus, the fragment may comprise domain II of CryIE, CryIB, CryID, CryIA, or CryIG, or a part of said domain II or a protein substantially simidlar to said domain II, and domain m of CryIC or a part of said domain III or a protein substantially similar to said domain III. It is particularly preferred that the fragment comprises domains I and II of CryIE, CryIB, CryID, CryIA, or CryIG, or a part thereof or a protein substantially similar to said domains I and II, and domain III of CryIC or a part thereof or a protein substantially similar to said domain III.

It is most preferred that the toxin fragment comprises a region at its C-terminus comprising the sequence from amino acid position 454 to position 602 of CryIC, or a sequence substantially similar to said sequence. The fragment may comprise a region at its C-terminus comprising the sequence from amino acid position 478 to 602 of CryIC, or a sequence substantially similar to said sequence, with the proviso that if the sequence comprising amino acids 478 to 602 of CryIC is fused directly to the C-terminus of domain II of CryIA, CryIB, CryID, CryIE, or CryIG, then the folding of the fusion product is satisfactory to yield an insecticidal component of the fragment. The routineer in the art will recognize that it may be necessary to add a peptide region to the C-terminus of domain II that spaces the C-terminal region of CryIC apart, thus enabling it to fold in such a way as to exhibit insecticidal activity.

It is most particularly preferred that the toxin fragment according to the invention comprises one of the following:

i) an amino acid sequence from about amino acid 1 to about amino acid 620 in SEQ ID NO:6, or an amino acid sequence from about amino acid 1 to about amino acid 620 in SEQ ID NO:6, wherein with respect to said sequence, at least one of the following alterations is present:
   Ile at position 609 is replaced with Leu,
   Ala at position 618 is replaced with Glu,
   Ser at position 620 is replaced with Tyr;
ii) an amino acid sequence from about amino acid 1 to about amino acid 627 in SEQ ID NO:8, or an amino acid sequence from about amino acid 1 to about amino acid 627 in SEQ ID NO:8, wherein with respect to said sequence, at least one of the following alterations is present:
   Ile at position 616 is replaced with Leu,
   Ala at position 625 is replaced with Glu,
   Ser at position 627 is replaced with Tyr; and
iii) an amino acid sequence from about amino acid 1 to about amino acid 602 in SEQ ID NO:12.

Whatever amino acid alterations are permitted, however, one or more of the following residues indicated sequence-wise with respect to the CryIC sequence is invariable: Phe (501), Val (478), Trp (479), and Thr (486).

The invention also includes a hybrid toxin comprising the above disclosed fragment or a toxin at least 85% similar to such a hybrid toxin, which has substantially similar insecticidal activity or receptor binding properties.

The invention still further includes pure proteins that are at least 90% similar to the toxin fragments or hybrid toxins according to the invention.

The invention still further includes recombinant DNA comprising a sequence encoding a protein comprising an amino acid sequence of one of the above-disclosed toxins or fragments thereof. The invention still further includes recombinant DNA comprising the sequence from about nucleotide 1 to about nucleotide 1860 given in SEQ ID NO:5, or DNA similar thereto encoding a substantially similar protein; or recombinant DNA comprising the sequence from about nucleotide 1 to about nucleotide 1881 in SEQ ID NO:7, or DNA similar thereto encoding a substantially similar protein; or recombinant DNA comprising the sequence from about nucleotide 1 to about nucleotide 1806 in SEQ ID NO:11, or DNA similar thereto encoding a substantially similar protein.

In the context of the present invention, "similar DNA" means a test sequence that is capable of hybridizing to the inventive recombinant sequence. When the test and inventive sequences are double stranded, the nucleic acid constituting the test sequence preferably has a TM within 20° C. of that of the inventive sequence. In the case that the test and inventive sequences are mixed together and denatured simultaneously, the TM values of the sequences are preferably within 10° C. of each other. More preferably, the hybridization is performed under stringent conditions, with either the test or inventive DNA preferably being supported. Thus, either a denatured test or inventive, sequence is preferably first bound to a support and hybridization is effected for a specified period of time at a temperature of between 50° C. and 70° C. in double strength citrate buffered saline containing 0.1% SDS, followed by rinsing of the support at the same temperature but with a buffer having a reduced SC concentration. Depending upon the degree of stringency required, and thus the degree of similarity of the sequences, such reduced concentration buffers are typically single strength SC containing 0.1% SDS, half strength SC containing 0.1% SDS and one tenth strength SC containing in 0.1% SDS. Sequences having the greatest degree of similarity are those the hybridization of which is least affected by washing in buffers of reduced concentration. It is most preferred that the test and inventive sequences are so similar that the hybridization between them is substantially unaffected by washing or incubation in one tenth strength sodium citrate buffer containing0.1% SDS. Typical stringent conditions are as follows: hybridization at 7% sodium dodecyl sulfate (SDS), 0.5 M NaPO$_4$ pH 7.0, 1 mM EDTA at 50° C.; wash with 2×SSC, 1% SDS, at 50° C.

The recombinant DNA may further encode a protein having herbicide resistance, plant growth-promoting, anti-fungal, anti bacterial, anti-viral, and/or anti-nematode properties. In the case that the DNA is to be introduced into a heterologous organism, it may be modified to remove known mRNA instability motifs (such as AT rich regions) and polyadenylation signals, and/or codons that are preferred by the organism into which the recombinant DNA is to be inserted may be used so that expression of the thus modified DNA in the organism yields substantially similar protein to that obtained by expression of the unmodified recombinant DNA in the organism in which the protein components of the hybrid toxin or toxin fragments are endogenous.

The invention still further includes a DNA sequence complementary to one that hybridizes under stringent conditions with the recombinant DNA according to the invention.

Also included in the present invention are the following: a vector containing such a recombinant (or complementary thereto) DNA: sequence; a plant or microorganism that includes and enables expression of such DNA; plants transformed with such DNA; the progeny of such plants that contain the DNA stably incorporated and hereditable in a Mendelian manner, and/or the, seeds of such plants and such progeny.

The invention still further includes protein derived from expression of the recombinant DNA of the invention, and insecticidal protein produced by expression of the recombinant DNA within plants transformed therewith.

The invention still further includes the following: an insecticidal composition containing one or more of the toxin fragments or toxins comprising them according to the invention; a process for combating insects that comprises exposing them to such fragments or toxins or compositions; and an extraction process for obtaining insecticidal proteins from organic material containing them, comprising submitting the material to maceration and solvent extraction.

DESCRIPTION OF THE FIGURES

FIG. 3 shows the alignment of amino acid residues 420 to 630 of CryIE and CryIC. The border between domain II and III is indicated. Only amino acid residues of CryIC that differ from CryIE are depicted; identical residues are indicated by dots. The crossover positions (F59, F71, F26, and E7) in the CryIC/CryIE hybrid toxin fragments are indicated on the Figure.

FIG. 6A shows the alignment of the cry1G. and cry1C genes with the crossover points of the cry1G/cry1C hybrids. The position relative to the first nucleotide of the start codon of cry1G is shown.

FIG. 6B shows the alignment of the encoded Cry1G and Cry1C proteins with the crossover points of the Cry1G/Cry1C hybrids. The approximate position of the domain II–III border is indicated by #. The position relative to the initiation codon of Cry1G is also indicated.

DESCRIPTION OF THE SEQUENCES IN THE SEQUENCE LISTING

Figure 1:
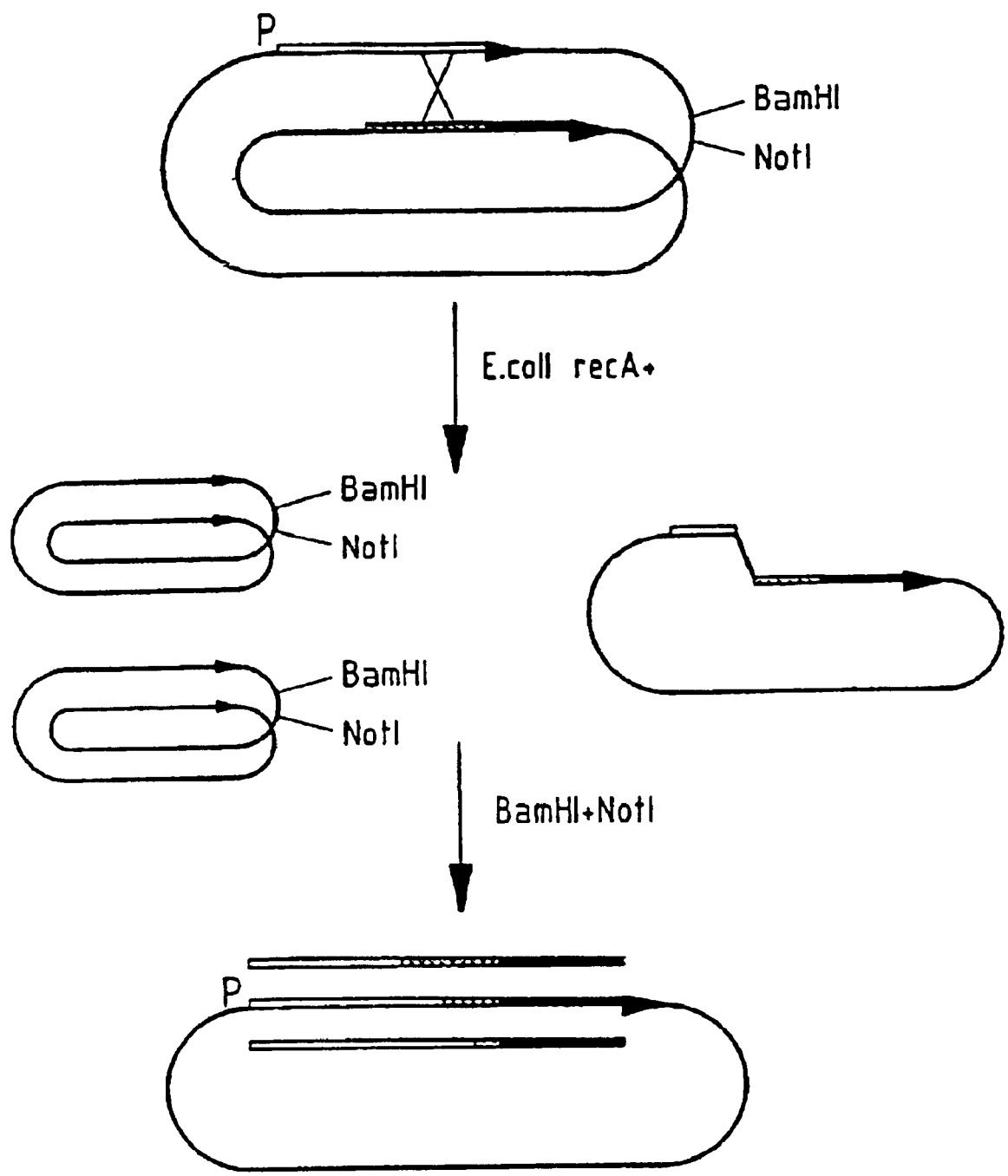
FIG. 1 shows the generation of hybrid crystal protein genes via in vivo recombination. Tandem plasmids (pBD560 and pBD 650) carrying two truncated crystal protein genes in direct repeat orientation are constructed. The 5' located gene (open bar) lacks the protoxin encoding region (solid bar) and of the 3' located gene (dashed bar) part of the domain I encoding region is deleted. In vivo recombination between homologous regions (domain It and E) occurs in recA+ strain JM101. Selection against non-recombinants by digestion with Not and BamHI and subsequent transformation results in sets of plasmids encoding hybrid crystal proteins.

SEQ ID NO:1 shows the nucleotide sequence of the CryIC gene from B.t. sub. sp. *entomocidus* 60.5.

SEQ ID NO:2 shows the amino acid sequence of the protein encoded by the CryIC gene shown in SEQ ID NO:1.

SEQ ID NO:3 shows the nucleotide sequence of the CryIE gene from B.t. sub. sp. *kenyae* 4FI.

SEQ ID NO:4 shows the amino acid sequence of the protein encoded by the CryIE gene shown in SEQ ID NO:3.

SEQ ID NO:5 shows the nucleotide sequence encoding a preferred CryIE/CryIC B.t. hybrid toxin fragment according to the invention.

SEQ ID NO:6 shows the amino acid sequence of the protein encoded by the nucleotide sequence shown in SEQ ID NO:5.

SEQ ID NO:7 shows the nucleotide sequence of a CryIA/CryIC hybrid toxin fragment according to the invention.

SEQ ID NO:8 shows the amino acid sequence of the protein encoded by the nucleotide sequence depicted in SEQ ID NO:7.

SEQ ID NO:9 shows the nucleotide sequence of a B.t. CryIG gene.

SEQ ID NO:10 shows the amino acid sequence of the protein encoded by the CryIG gene shown in SEQ ID NO:9.

SEQ ID NO.11 shows the nucleotide sequence encoding a preferred CryIG/CryIC B.t. hybrid toxin fragment (hybrid HK28-24) according to the invention.

SEQ ID NO:12 shows the amino acid sequence of the protein encoded by the nucleotide sequence shown in SEQ ID NO:11.

SEQ ID NOs:13–15 are oligonucleotides.

The invention will be further apparent from the following non-limiting Examples, which describe the production of B.t. hybrid toxin fragments according to the invention, taken in conjunction with the associated Figures and Sequence Listing.

EXAMPLES

Production Of Plasmids Encoding Hybrid Toxin Fragments

In the production of plasmids carrying the CryIC or CryIE genes, *Escherichia coli* XU-blue (Stratagene Inc.) is used as plasmid host except in cases were JM101 is used as recA+ background. A vector for the expression of crystal proteins in *E. coli* is derived from pKK233-2 (Pharmacia LKB Biotechnology). The size of pKK233-2 is reduced by deleting an EcoRI-PvuII fragment carrying the gene encoding tetracycline resistance. Subsequently a 6 bp XhoI linker is ligated into the HindIII site resulting in pBD10. Plasmid BK+is created by insertion of a BglII linker in the SacI site of Bluescript SK+ (Stratagene Inc.). The polylinker of BK+from BglII to XhoI is introduced between the NcoI-XhoI site in pBD10. The resulting expression vector pBD11 contains the highly expressed trc promoter, the lacZ ribosome binding site and ATG initiation codon. The initiation codon overlaps with a NcoI site and is followed by the polylinker to facilitate insertions into the vector. Transcription is terminated by the rrnB transcription terminator.

The cloning of the cryIC and cryIE genes from B.t. sub. sp. *entomocidus* 60.5 and *kenya* 4F1 respectively is as described previously (Honée et al., 1990 (Appl. Environ. Microbiol. 56, pp. 823–825); Visser et al., 1990 (J. Bacteriol. 172, pp. 6783–6788)). For cloning purposes, an NcoI site overlapping with the start codon of cryIC is created by in vitro mutagenesis. A BglII site is created directly downstream of the translation termination codon of cryIC by site directed mutagenesis, resulting in the sequence A<u>TAA</u>GATCTGIT (SEQ ID NO:13—stopcodon underlined). The NcoI-BglII fragment containing the cryIC coding region is ligated into pBD11, resulting in CryIC expression plasmid pBD150. pBD155 is a derivative of pBD150, in which the polylinker sequences 3' of cryIC are deleted.

A DraI fragment from pEM14 (Visser et al., 1990) containing the complete cryIE gene is cloned in the EcoRV site of SK+, resulting in plasmid pEM15. Subsequently, an NcoI site is: introduced by site directed mutagenesis at the start codon of the gene, and cryIE is transferred as an NcoI-XhoI fragment to pBD11, resulting in CryIE expression plasmid pBD160.

Plasmids carrying only toxic fragment-encoding regions of the cryI genes are constructed. BglII linkers are ligated to XmnI sites present at bp position 1835 of cryIC, and to the HgiAI site at position 1839 of cryIE. Subsequently, NcoI-BglII fragments containing the cryIC (1835 bp) and cryIE (1839 bp)toxic fragment-encoding regions are ligated into pBD11, resulting in pBD151 and pBD161 respectively as described below.

Tandem plasmids used for the generation of cryIC-cryIE hybrid genes are constructed as follows: BamHI linkers are ligated to pBD160 digested with HpaI. This DNA is incubated with BamHI and XhoI and the truncated cryIE gene running from bp 704 is ligated into pBD151 resulting in pBD560. To construct a tandem plasmid for the generation of cryIE-cryIC hybrids, pBD155 is digested with NsiI and XhoI. The fragment carrying the truncated cryIC gene, running from bp 266, is ligated into PstI/XhoI digested pBD161, resulting in plasmid pBD650. Due to polylinker sequences, unique NotI and BamH1 restriction sites are present between the truncated cryI genes present in the tandem plasmids pBD560 and pBD650.

DNA Manipulations and Construction of Hybrid Toxins

All recombinant DNA techniques are as described by Sambrook et al. 1989 (in "Molecular Cloning, A Laboratory Manual: Cold Spring Harbour Press, Cold Spring Harbour). DNA sequencing is performed by the dideoxytriphosphate method with fluorescent dyes attached to the dideoxynucleotides. Analysis is automated by using an Applied Biosystems 370A nucleotide sequence analyzer.

The homology present between cryI genes permits intramolecular recombination in vivo. Two tandem plasmids are created, each carrying two truncated crystal protein genes overlapping only in domains II and III. Therefore, recombination occurs only in regions encoding domains II and III. In-frame recombinations, which can be selected for by restriction enzyme digestion, generate plasmids that express full size 140 kDa hybrid protoxins. To generate in vivo recombinants, a tandem plasmid (either pBD560 or pBD650; FIG. 2) is transferred to JM101. 5 mg of DNA is isolated from independently generated recombinants and is digested with NotI and BamHI cutting between the two truncated cryI genes to select against non-recombinants, and the DNA is transformed to *E. coli* XL1-blue. 5 single colonies are grown and protein patterns and plasmid content are analyzed.

CryIC/CryIE and CryIE/CryIC hybrid toxins are generated using the tandem plasmids pBD560 and pBD650 respectively, which are allowed to recombine in a recA+ background. DNA is isolated, digested, and transferred to recA− strain as described above.

100 colonies of 20 independent experiments are analyzed on SDS-PAGE. 85% of these clones produce a 140 kDa protein indicating in frame recombinations between cryIC and cryIE, and cryIE and cryIC, respectively. In *E. coli,* CryI proteins are produced as crystals that can be solubilized in vitro at high pH. Approximately 15% of hybrid toxins produced as above are solubilized at high pH. The recombinants producing soluble hybrid toxins are first classified using restriction enzymes. Subsequently, for each class, the crossover point of selected hybrids is: determined by DNA sequence analysis. All crossovers resulting in soluble hybrid toxins occur in or very close to domain III.

Protein Purification and Analysis

Crystal proteins are isolated essentially as described by Convents et al (J. Biol. Chem. 265, pp. 1369–1375; Eur. J. Biochem., 195, pp. 631–635). Briefly, recombinant *E. coli* are grown at 30° C. in 250 ml TB medium to an $OD_{660}$ of 10–15. Crystals isolated from the *E.coli* lysate are solubilized during incubation for 2 hours in 20 mM $Na_2CO_3$, 10 mM dithiothreitol, 100 mM NaCl, pH10, at 37° C. The pH of the solution is lowered to 8 with Tris-HCl and incubated with trypsin. The toxin solution is dialysed against 20 mM Tris-HCl, 100 mM, NaCl pH9. Subsequently, the toxic fragment is purified on a Mono Q 5/5 column connected to a fast-protein liquid chromatography (FPLC) system (Pharmacia LKB Biotechnology). Proteins are separated by 7.5% sodium dodecyl sulfate-polyacrylamide gel electrophoreses.

Biochemical Analysis and Isolation of 65 kDa Toxic Fragments

Isolated crystals of purified CryIC, CryIE, and the hybrid proteins are solubilized at high pH and incubated with trypsin. Like CryIC and CryIE, all soluble hybrid toxins with crossovers in domain III are converted to stable 65 kDa fragments. The 65 kDa fragments can be purified using anion exchange chromatography under similar conditions as the parental proteins. Hybrids F59 and F71, which have crossovers in domain II, are completely degraded by trypsin. Apparently, although these hybrids do not precipitate as insoluble aggregates, trypsin cleavage sites buried in the parental proteins may become exposed to trypsin. Because of this phenomenon, no 65 kDa fragments are isolated from F59 and F71.

Table 1 shows the constitution of 5 CryIE/CryIC hybrid toxins: (G27, H8, H17, H13, H7, and H21) and 4 CryIC/CryIE hybrid toxins (F59 F71, F26, and E7) with reference to the cryIC and CryIE proteins from which they are derived. The amino acid sequences of the CryIE/CryIC toxins comprising the toxic fragments of the present invention run to amino acid; 1189 of the CryIC parent protein. The amino acid sequences of the CryIC/CryIE hybrid toxins run to amino acid 1171 of the CryIE parent protein. Table 1 also shows the relative insecticidal effectiveness of these various hybrid toxins with respect to the CryIC and CryIE proteins.

TABLE 1

| Toxin | aa IE | aa IC | *M. sexta* | *S. exigua* | *M. brassicae* |
|---|---|---|---|---|---|
| IC | 0 | 28–627 | ++ | ++ | ++ |
| IE | 29–612 | 0 | ++ | – | – |
| G27 | 1–474 | 478–627 | ++ | ++(+) | +(+) |
| H8 | 1–497 | 501–627 | ++ | – | – |
| H17 | 1–529 | 533–627 | ++ | – | – |
| H7 | 1–577 | 588–627 | – | – | – |
| H21 | 1–605 | 621–627 | | | |
| F59 | 421–612 | 1–423 | – | – | – |
| F71 | 428–612 | 1–430 | – | – | – |
| F26 | 455–612 (1171) | 1–458 | ++ | – | – |
| E7 | 588–612 (1171) | 1–602 | ++ | ++ | ++ |

Table. 1. Constitution and toxicity of hybrid toxins with respect to the parent proteins. Most bioassays were performed with purified toxin fragments. In case of CryIC these run from about aa 28 to about aa 627, and in case of CryIE till 612. The length of complete protoxins is indicated between brackets.

Insect Toxicity Assays and Insecticidal Activity of cryIC/cryIE Hybrid Gene Products Bacterial cultures are concentrated to $OD_{660}$ 6.0, and 100 ml are spotted on 2 cm² of artificial diet in a 24-well tissue culture plate. Alternatively, diluted samples of purified toxins are applied to the diet Second instar larvae of either *S. exigua, M. brassicae,* or *M. sexta,* are fed on this diet (16 per sample dilution) for days, after which the larval weight is scored. The relative growth (EC50, the concentration giving 50% growth reduction) is determined by calculating the ratio between the mean weight of larvae grown on diet supplemented with toxin and the mean weight of control larvae grown on a diet without toxin. *M. sexta* egg layers are supplied by Carolina Biological Supply Company, North Carolina, USA.

The toxic fragments encoded by the hybrid gene products are tested for activity towards three different insect species as described above. *M. sexta* is susceptible to both CryIC and CryIE. As may be anticipated from their sensitivity to trypsin, hybrids F59 and F71 are not active against this insect (Table 1). Although H7 is converted by trypsin to stable 65 kDa proteins, it is not toxic to *M. sexta*. All of the other hybrids given in Table 1 are toxic and are apparently in the native, biologically active conformation.

Figure 2:
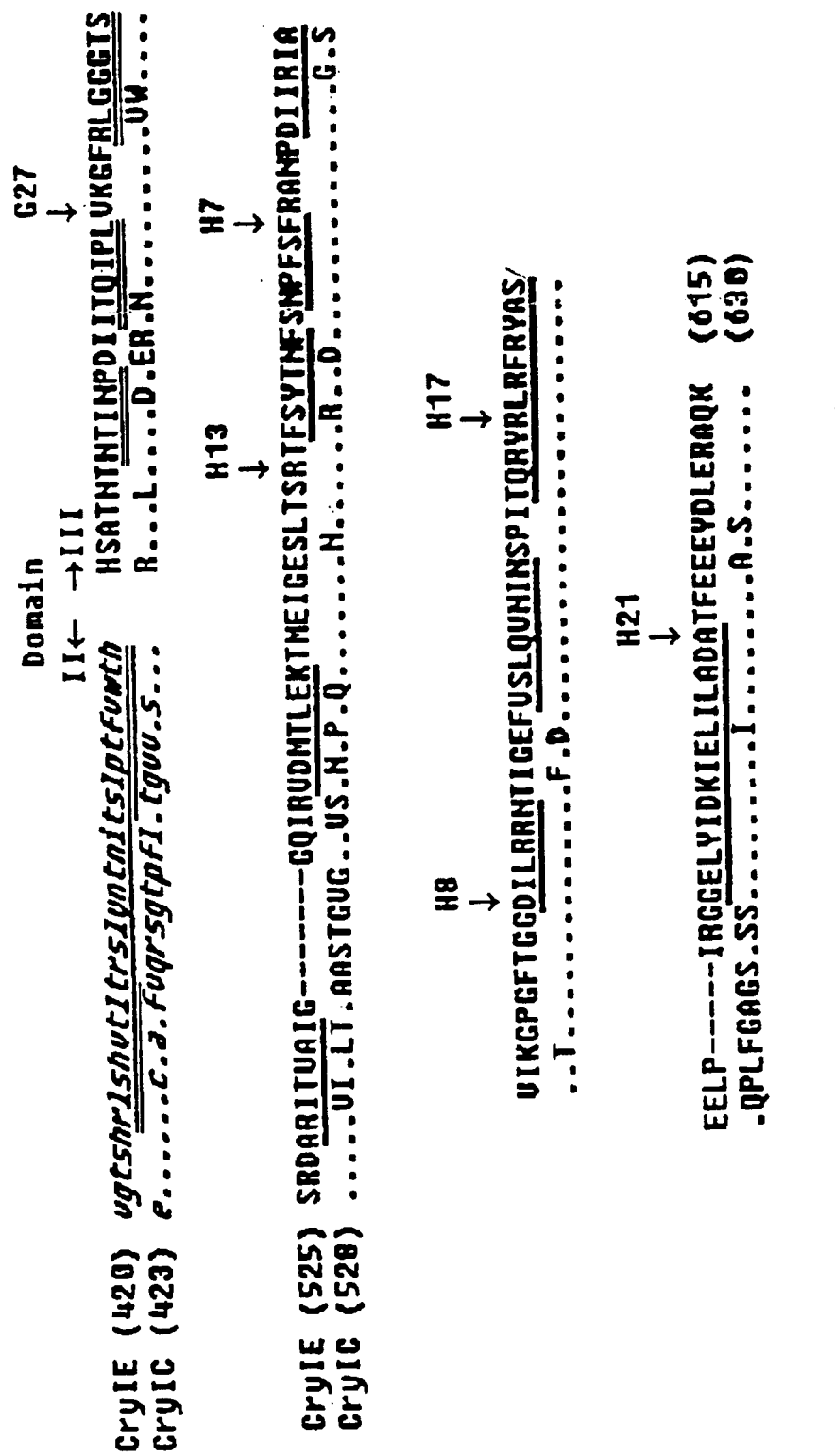
FIG. 2 shows the alignment of amino acid residues 420 to 630 of CryIE and CryIC. The border between domain II and m is indicated. Only amino acid residues of CryIC that differ from CryIF are depicted; identical residues are indicated by dots. The crossover positions (G27, H13, H7, H8, H17, and H21l) in the CryIE/CryIC hybrid toxin fragments according to the invention are indicated on the Figure.

The 65 kDa fragment of CryIC is highly toxic towards *S. exigua* and *M. brassicae,* whereas CryIE is not. G27 (Table 1; FIG. 2), a CryIE-CryIC hybrid with a crossover at the junction of domain II and m is active towards both insects. This demonstrates that domain III of CryIC confers full activity towards *S. exigua* and *M. brassicae*. Hybrid H8, which differs in only three amino acid residues (see FIG. 3) from G27, although active against *M. sexta,* is not active against *S. exigua* and *M. brassicae*.

F26 (Table 1; FIG. 3), the reciprocal hybrid of G27, in which domain III of CryIC has been exchanged by domain III of CryIE, is not active against *S. exigua* or *M. brassicae*. Apparently, although the protein is toxic to *M. sexta,* the CryIC sequences running from amino acid 28–462 are not sufficient to kill *S. exigua* and *M. brassicae*. Only when CryIC sequences Up to amino acid residue 602 are present in the hybrid (E7) is insecticidal activity against these insects restored. The present disclosure indicates that amino acid residues from 478–602 of CryIC can confer high insecticidal activity to CryIE against *S. exigua* and *M. brassicae*.

Biotinylation of Crystal Proteins and Binding Assays

Biotinylation is performed using biotin-N-hydroxysuccinimide ester essentially as described by the manufacturer (Amersham). 1 mg of crystal protein is incubated with 40 ml biotinylation reagent in 50 mM $NaHCO_3$, 150 mM NaCl, pH8, for one hour at 20° C. The solution is loaded on a Sephadex 25 column equilibrated with the same buffer containing 0.1% BSA to remove unbound biotin, and samples of the fractions are spotted on a nitrocellulose membrane. Fractions containing biotinylated crystal proteins are visualized using streptavidin-peroxidase conjugate (Amersham) which catalyzes the oxidation of luminol, resulting in chemiluminescence (ECL, Amersham), and pooled.

Brush border membrane vesicles are isolated as described by Wolfersberger et al. (1987) (Corp. Biochem. Physiol. 86a, pp. 301–308) except that the vesicles are washed once more with isolation buffer containing 0.1% Tween 20. Binding of biotinylated crystal proteins to brush border membrane vesicles (100 mg/ml) is performed in 100 ml of PBS containing 1% BSA, 0.1% Tween-20 (pH 7.6). Vesicles (20 µg vesicle protein) are incubated with 10 ng biotinylated crystal proteins in the presence or absence of 1000-fold excess of unlabelled crystal proteins for 1 hour at 20° C. Subsequently, the vesicles are re-isolated by centrifugation for 10 minutes at 14,000 g in an Eppendorf centrifuge, washed twice with binding buffer, re-suspended in sample buffer, denatured by heating, and loaded on 7.5% polyacrylamide gels. After electrophoresis, proteins are blotted to nitrocellulose membranes and biotinylated crystal proteins that are re-isolated with the vesicles are visualized by incubation of the nitrocellulose with streptavidin-peroxidase conjugate (Amersham), which catalyzes the oxidation of luminol, resulting in chemiluminescence (ECL, Amersham).

Figure 4:
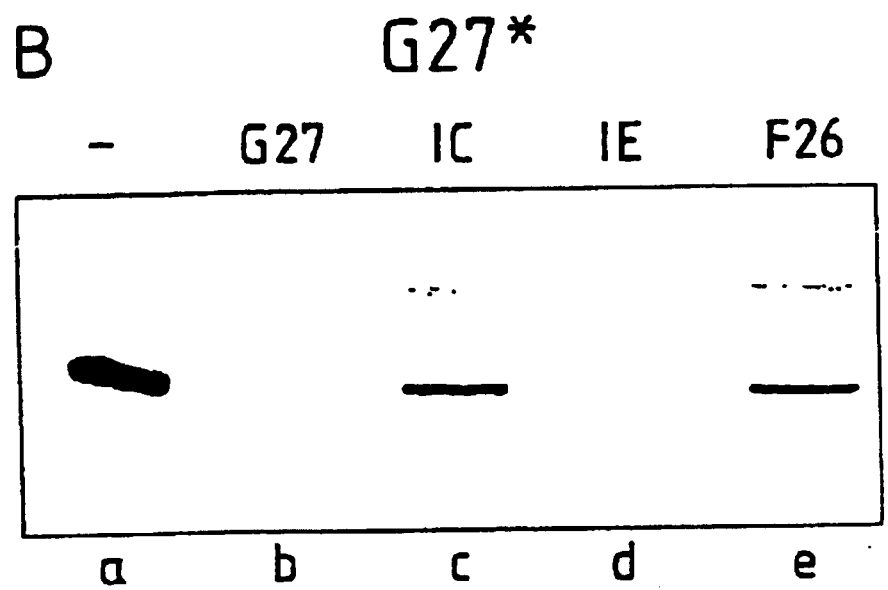
FIG. 4 shows the results of heterologous competition experiments. Biotinylated CryIC (panel A) and G27 (panel B) are incubated with S. exigua BBMV vesicles in the absence (lanes a) or presence of an excess of unlabelled protein as indicated. After the incubation, the vesicles are washed, loaded on a SDS-polyacrylamide gel and blotted to a nitrocellulose membrane. Biotinylated crystal proteins, re-isolated with the vesicles, are visualized using streptavidin-peroxidase conjugate and are indicated on the Figure with an arrow head.
Figure 4:
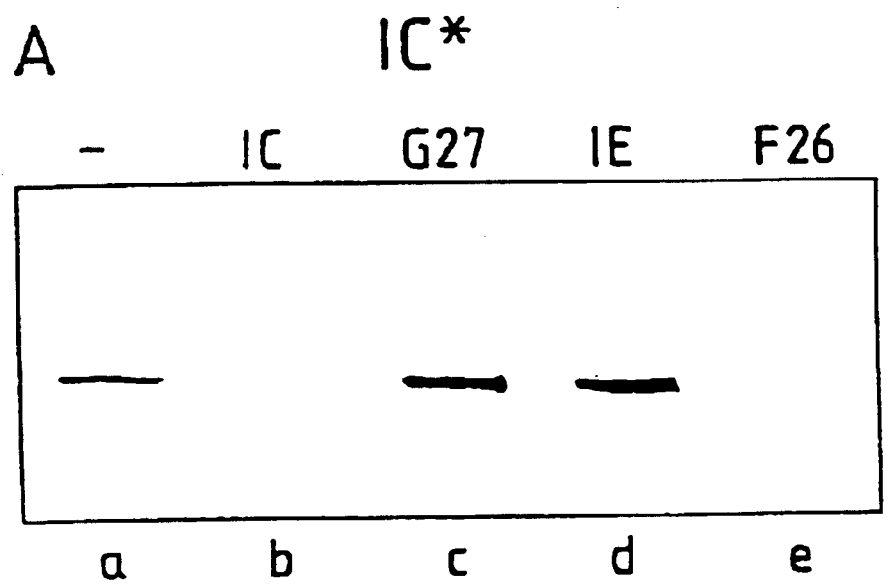

Because binding to epithelial gut cells is a key step in the mode of action of crystal proteins, the binding of crystal proteins to *S. exigua* brush border membrane vesicles is investigated in heterologous competition experiments. Competition experiments demonstrate that the binding of labeled CryIC (FIG. 4A, lane a) and labeled F26 (not shown) can be outcompeted by an excess of both unlabelled CryIC (lane b) or F26 (lane e) but not with an excess of G27 (lane c) or CryIE (lane d). Furthermore, binding of labeled G27 (FIG. 4B, lane a) and labeled CryIE (not shown) can be outcompeted by an excess of G27 (lane b) or CryIE (lane d), but not with an excess of CryIC (lane a) or F26 (lane e). From these results, it is concluded that G27 and CryIE recognize the same binding sites on *S. exigua* midgut membranes and that these sites differ from those that are recognized by CryIC and F26. The toxicity and binding assays combined demonstrate that G27 is as toxic as CryIC but that it binds a receptor different therefrom. As insects can develop resistance against a crystal protein by changing receptor binding characteristics, G27 may be used in resistance management programs as an alternative to CryIC.

Expression of cryIE/cryIC Hybrid Toxin Genes in Heterologous Systems

The G27 cryIE/cryIC hybrid toxin gene is expressed in *E.coli,* and the gene product exhibits at least the same insecticidal activity (at least against Spodoptera) as CryIC. Moreover, the product exhibits an increase in such activity when expressed in a *Bacillus thuringiensis* strain (see below). The gene encoding the G27 hybrid toxin is introduced into a suitable shuttle vector system, which is then introduced into an appropriate B.t. host. Such transformed cells are then cultured, and the resulting toxin from both whole cultures and purified crystals is assayed for insecticidal activity.

Figure 5:
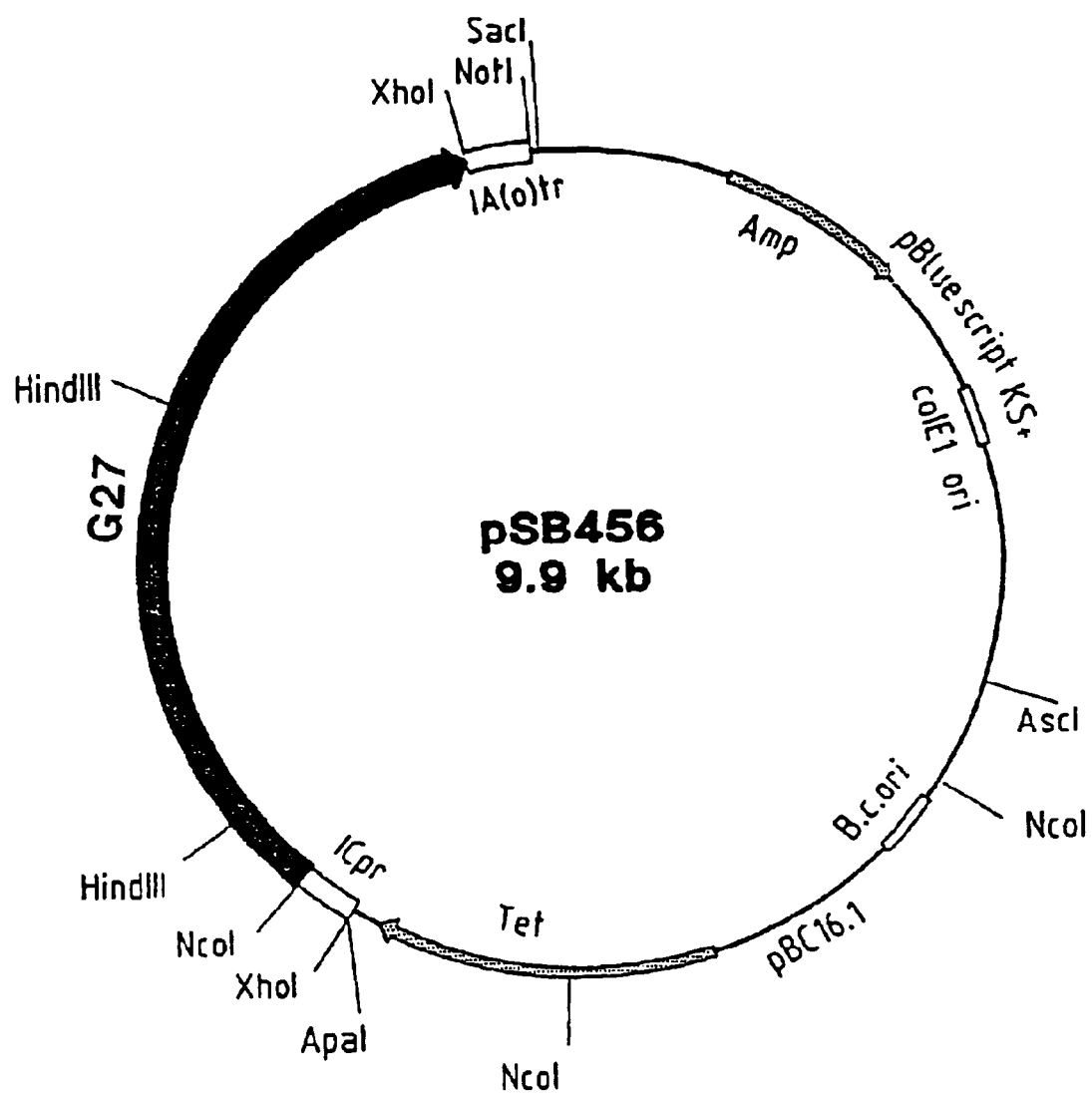
FIG. 5 shows the plasmid map of pSB456, which encodes the G27 hybrid toxin fragment and is used to transform the crystal toxin minus strain B.t. 51.

Construction of a G27-Containing Shuttle Vector, Transformation of Bt51, and Purification of Toxin Protein Therefrom The gene encoding hybrid G27 (3.4 kb) is cleaved from a pKK233 *E. coli* expression plasmid using NcoI and XhoI. The XhoI site is filled in using the Klenow fragment of *E. coli*. DNA Polymerase I. The resulting fragment is ligated to NcoI/SmaI-digested pSB635 (pBluescriptKS+, $P_{cryIC}$, and the CryIA(c) transcription terminator). The resulting plasmid, pSB453, is digested with ApaI and NotI, yielding a 4.2 kbp fragment carrying the promoter, the hybrid G27 ORF, and the terminator. This fragment is ligated to ApaI/NotI-digested pSB634 (shuttle vector containing pBC16.1 and pBluescriptKS+), yielding pSB456 (see FIG. 5). Plasmid DNA isolated from *E. coli* DH10B is used to transform the crystal toxin minus B.t. strain, Bt51. Positive isolates are tetracycline resistant, show the presence of pSB456, and contain large inclusions corresponding to a 135 kDa protein (as determined by SDS-PAGE). G27 hybrid toxin samples are prepared from cultures of transformed Bt51 grown through sporulation at 30° C. in CYS-Tc[10] media.: Insecticidal bioassays (Table 2) are performed on both full whole cultures and on washed crystal protein preparations. Controls include Bt51 (pSB440) containing the CryIC toxin and Bt51 (pSB636) containing CryIE. Toxin concentrations are estimated by SDS-PAGE.

TABLE 2

Bioassay of the hybrid toxin G27 in comparison to CryIC and CryIE. The number of samples is given in parentheses. The hybrid toxin G27 is about 50% more effective than either CryIE or CryIC with respect to toxicity to Spodoptera sp.

| Toxin | Whole Culture (ppt) | | | $LC_{50}$ Washed Crystal Protein (ppm) | |
|---|---|---|---|---|---|
| CryIC | 56(2) | 36(2) | 40(4) | 7.8(2) | 8.1(4) |
| CryIE | 79(1) | 78(1) | 33(4) | 11.1(6) | 7.5(4) |
| G27 | 29(2) | 21(2) | 25(4) | 4.7(4) | 6.0(4) |
| Ratio (IC/G27) | 1.93 | 1.71 | 1.60 | 1.66 | 1.35 |

Production and Selection of Cry1G/Cry1C Hybrid Toxins

To obtain Cry1G/Cry1C hybrid toxins by in vivo recombination, expression vector pHK26 was constructed with a C-terminal truncated cryIG (a k a. Cry9A) gene(see, SEQ ID NO:9) and a N-terminal truncated cryIC gene (see, SEQ ID NO:1) cloned in tandem. The plasmid pHK26 contains the trc promoter followed by bases 1–1650 of cryIG, part of the pBluescript SK+ polylinker, and bases 266–3570 of cryIC. pHK26 is a derivative of pRM7 in which the cry1A(b) coding sequences from NcoI to BglII have been replaced by part of the cry1G gene. The 1650 bp NcoI-BglII cry1G fragment was isolated by PCR amplification from plasmid pSB1501 using the primers dGCTAGC-CATGGATCAAAATAAACACGGAATrATTG (SEQ ID NO:14) and dCTGGTCAGATTGAAGTAGAGCTCC (SEQ ID NO:15). After allowing intramolecular recombination of pHK26 in E. coli strain JM101, plasmid DNA was isolated and digested with BamHI and PinAI to linearize non-recombinant plasmids. Both BamHI as well as PinAI have unique recognition sites in pHK26, in the polylinker and at position 1074 of cryIC, respectively. The overlap between the two truncated cry genes in pHK26 that allows recombination extends approximately 1400 base pairs, vet primary interest was in recombinations in or close to domain III. Therefore, PinAI was chosen rather than a second enzyme with a recognition site in the polylinker. This strategy allowed linearization of recombinants with crossovers in front of the PinAI site, thereby effectively selecting for recombinants with crossovers in or near the domain III-encoding sequences.

Digested plasmids were transferred to E. coli XL1 cells by transformation, and plasmids from transformants were subsequently analyzed by restriction enzyme digestion and DNA electrophoresis. Over 80% of the transformants contained a plasmid with an insert size corresponding to a single, intact cry gene, indicating that selection for homologous recombination events had been efficient. Thirty separate colonies were grown in TB medium and assayed for production of alkaline-soluble protoxins that could be converted to stable 65 kD toxic fragments upon trypsin incubation. This screening method yielded 6.colonies producing a stable 65 kD toxic fragment of the expected size. The location of the crossovers in the hybrid genes was first determined by restriction analysis and finally by nucleotide sequencing. Only three different crossover sites occurred in the 6 hybrid genes thus tested. The hybrid genes were designated HK28-12, HK28-1, and HK28-24. The location of the three different crossover sites is shown in FIGS. 6A and 6B. The three crossovers are located close to the border between domains II and III, with the three hybrid toxins, designated HK28-12, HK28-1, and HK28-24, differing only one amino acid from each other. Both the solubility of the hybrid protoxins as well as the occurrence of trypsin-resistant products of the expected size suggested that these hybrids proteins were properly folded and might have biological activity. This was subsequently tested against larvae of Spodoptera exigua.

Figure 7:
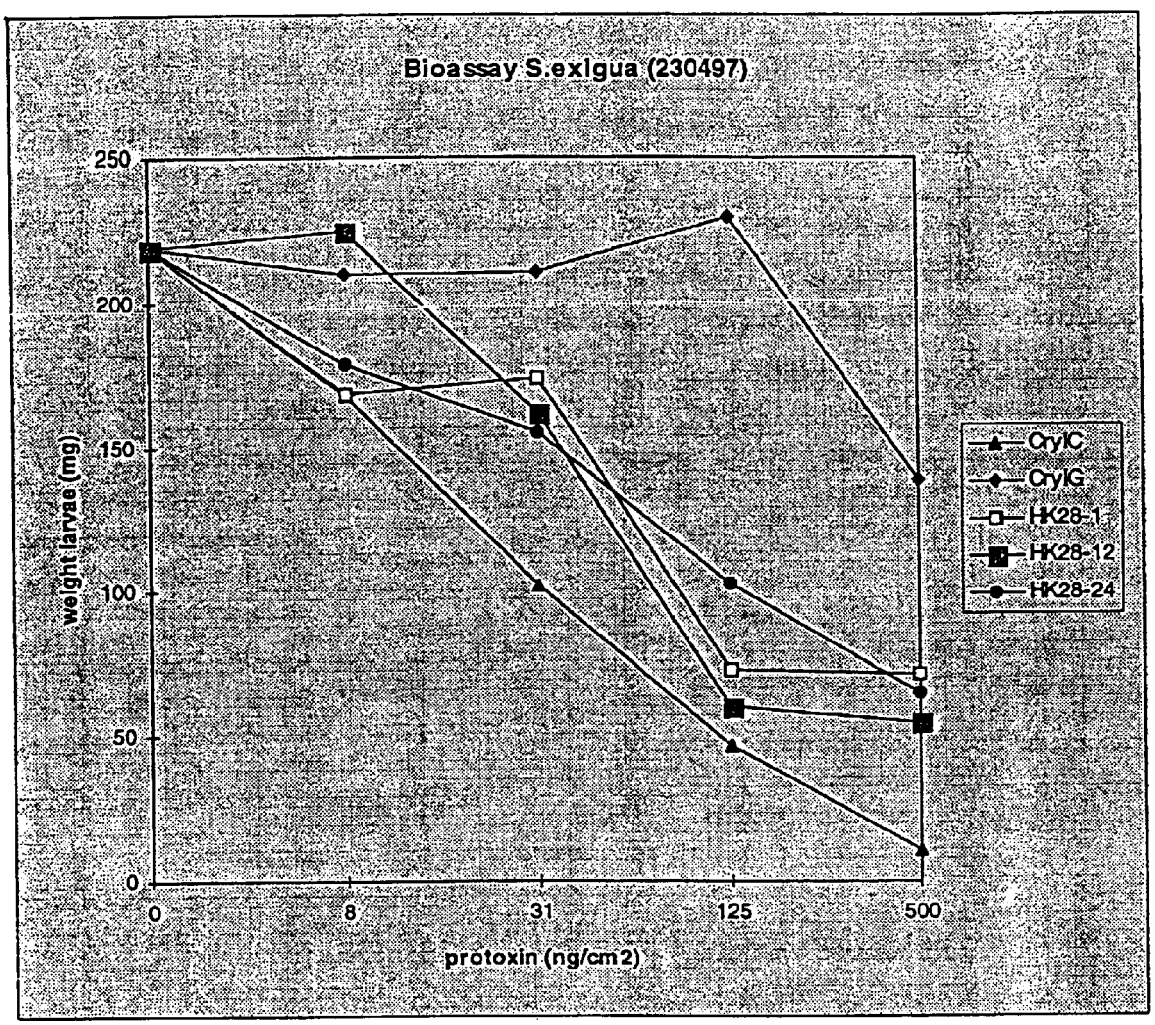
FIG. 7 shows the results of assays measuring the toxicity of Cry1G/Cry1C hybrid toxins towards *Spodoptera exigua*.

Toxicity of CryIG/CryIC Hybrid Toxins Towards Spodoptera exigua,

The cryIC, cryIG, and newly isolated cryIG/cryIC hybrid genes were introduced in E. coli strain XL1-blue and grown for 48 hours at 28° C. in TB medium with ampicillin. Cells were disrupted by sonification, and protoxin-containing crystals were isolated by centrifugation. After washing the crystals, the protoxins were solubilized at high pH and the concentration of the 140 protoxins in the supernatant was estimated by SDS-PAGE. These samples were assayed for their toxicity to S. exigua larvae. Results are shown in FIG. 7.

CryIG protoxin is much less toxic to S. exigua than CryIC. The hybrids containing domain III of CryIC are significantly more toxic than Cry1G. These results show that, as was demonstrated earlier for CryIE and Cry1A(b), CryIG can be made considerably more toxic to S. exigua by substituting its domain III with that of CryIC. For example, hybrid HK28-24 (SEQ ID NO:12) is much more toxic to S. exigua than Cry1G (SEQ ID NO:10). Hybrid HK28-24 is also much more toxic to S. frugiperda than Cry1G (data not shown).

Although the present invention has been particularly described with reference to the production of Cry1E/Cry1C and Cry1G/Cry1C hybrid toxins, the routineer in the art will appreciate that many other hybrid toxins having improved insecticidal characteristics may be produced according to the present disclosure. SEQ ID NOs:7 and 8, for example, depict the nucleotide and amino acid sequences, respectively, of a CryIA/CryIC hybrid toxin fragment according to the invention that has improved insecticidal activity. Hybrid toxins may be produced comprising domain III of CryIC and the N-terminal region, including domains I and II, of any other Cry protein. In terms of bioassays, the hybrid toxin-carrying transformants may be grown in SOP media to expedite the assay procedures and reduce the volumes of material required. Moreover, the genes encoding the Cry1E/Cry1C, Cry1G/Cry1C, Cry1A/Cry1C, and/or other hybrid toxins according to the invention may be transferred into toxin-encoding strains of B.t. and/or integrated into the chromosome of selected strains of B.t. or introduced into plant genomes to provide for insecticidal activity in situ within the plant per se. In this regard, it is particularly preferred that the recombinant DNA encoding the toxins is modified so that codons that are preferred by the plant into which the recombinant DNA is to be inserted are used, whereby expression of the thus modified DNA in the plant yields substantially similar protein to that obtained by expression of the unmodified recombinant DNA in the organism in which the protein components of the hybrid toxin or toxin fragments are endogenous.

Isolation of Additional B.t. Toxin Genes Based on Sequence Similarity to Known B.t. Toxin Genes A library is plated at a density of approximately 8,000 pfu per 10 cm Petri dish, and filter lifts of the plaques are made after 7 hours growth at 37° C. The plaque lifts are probed with the cDNA set forth in SEQ ID NO:1, 3, or 9 labeled with 32P-dCTP by the random priming method by means of a PrimeTime kit (International Biotechnologies, Inc., New Haven, Conn.). Exemplary hybridization conditions are 7% sodium dodecyl sulfate (SDS), 0.5 M NaPO₄ pH 7.0, 1 mM EDTA at 50° C. After hybridization overnight, the filters are washed with 2×SSC, 1% SDS at 50° C. Positively hybridizing plaques are detected by autoradiography. After purification to single plaques, cDNA inserts are isolated, and their sequences determined by the chain in termination method using dideoxy terminators labeled with fluorescent dyes (Applied Biosystems, Inc., Foster City, Calif.). This experimental protocol can be used by one of ordinary skill in the art to obtain B.t. toxin genes substantially similar to those set forth in the Sequence Listing.

SEQUENCE LISTING (1) GENERAL INFORMATION:

(iii) NUMBER OF SEQUENCES: 15

(2) INFORMATION FOR SEQ ID NO: 1:

(i) SEQUENCE CHARACTERISTICS:
       (A) LENGTH: 3567 base pairs
       (B) TYPE: nucleic acid
       (C) STRANDEDNESS: single
       (D) TOPOLOGY: unknown (ii) MOLECULE TYPE: cDNA (iii) HYPOTHETICAL: NO (iv) ANTI-SENSE: NO (vi) ORIGINAL SOURCE:
       (A) ORGANISM: Bacillus thuringiensis (ix) FEATURE:
       (A) NAME/KEY: CDS
       (B) LOCATION: 1..3567

(xi) SEQUENCE DESCRIPTION: SEQ ID NO: 1:

```
ATG GAG GAA AAT AAT CAA AAT CAA TGC ATA CCT TAC AAT TGT TTA AGT        48
Met Glu Glu Asn Asn Gln Asn Gln Cys Ile Pro Tyr Asn Cys Leu Ser
 1               5                  10                  15

AAT CCT GAA GAA GTA CTT TTG GAT GGA GAA CGG ATA TCA ACT GGT AAT        96
Asn Pro Glu Glu Val Leu Leu Asp Gly Glu Arg Ile Ser Thr Gly Asn
             20                  25                  30

TCA TCA ATT GAT ATT TCT CTG TCA CTT GTT CAG TTT CTG GTA TCT AAC       144
Ser Ser Ile Asp Ile Ser Leu Ser Leu Val Gln Phe Leu Val Ser Asn
         35                  40                  45

TTT GTA CCA GGG GGA GGA TTT TTA GTT GGA TTA ATA GAT TTT GTA TGG       192
Phe Val Pro Gly Gly Gly Phe Leu Val Gly Leu Ile Asp Phe Val Trp
     50                  55                  60

GGA ATA GTT GGC CCT TCT CAA TGG GAT GCA TTT CTA GTA CAA ATT GAA       240
Gly Ile Val Gly Pro Ser Gln Trp Asp Ala Phe Leu Val Gln Ile Glu
 65                  70                  75                  80

CAA TTA ATT AAT GAA AGA ATA GCT GAA TTT GCT AGG AAT GCT GCT ATT       288
Gln Leu Ile Asn Glu Arg Ile Ala Glu Phe Ala Arg Asn Ala Ala Ile
                 85                  90                  95

GCT AAT TTA GAA GGA TTA GGA AAC AAT TTC AAT ATA TAT GTG GAA GCA       336
Ala Asn Leu Glu Gly Leu Gly Asn Asn Phe Asn Ile Tyr Val Glu Ala
            100                 105                 110

TTT AAA GAA TGG GAA GAA GAT CCT AAT AAT CCA GAA ACC AGG ACC AGA       384
Phe Lys Glu Trp Glu Glu Asp Pro Asn Asn Pro Glu Thr Arg Thr Arg
        115                 120                 125

GTA ATT GAT CGC TTT CGT ATA CTT GAT GGG CTA CTT GAA AGG GAC ATT       432
Val Ile Asp Arg Phe Arg Ile Leu Asp Gly Leu Leu Glu Arg Asp Ile
    130                 135                 140

CCT TCG TTT CGA ATT TCT GGA TTT GAA GTA CCC CTT TTA TCC GTT TAT       480
Pro Ser Phe Arg Ile Ser Gly Phe Glu Val Pro Leu Leu Ser Val Tyr
```

```
                145                 150                 155                 160
GCT CAA GCG GCC AAT CTG CAT CTA GCT ATA TTA AGA GAT TCT GTA ATT          528
Ala Gln Ala Ala Asn Leu His Leu Ala Ile Leu Arg Asp Ser Val Ile
                    165                 170                 175

TTT GGA GAA AGA TGG GGA TTG ACA ACG ATA AAT GTC AAT GAA AAC TAT          576
Phe Gly Glu Arg Trp Gly Leu Thr Thr Ile Asn Val Asn Glu Asn Tyr
                180                 185                 190

AAT AGA CTA ATT AGG CAT ATT GAT GAA TAT GCT GAT CAC TGT GCA AAT          624
Asn Arg Leu Ile Arg His Ile Asp Glu Tyr Ala Asp His Cys Ala Asn
            195                 200                 205

ACG TAT AAT CGG GGA TTA AAT AAT TTA CCG AAA TCT ACG TAT CAA GAT          672
Thr Tyr Asn Arg Gly Leu Asn Asn Leu Pro Lys Ser Thr Tyr Gln Asp
        210                 215                 220

TGG ATA ACA TAT AAT CGA TTA CGG AGA GAC TTA ACA TTG ACT GTA TTA          720
Trp Ile Thr Tyr Asn Arg Leu Arg Arg Asp Leu Thr Leu Thr Val Leu
225                 230                 235                 240

GAT ATC GCC GCT TTC TTT CCA AAC TAT GAC AAT AGG AGA TAT CCA ATT          768
Asp Ile Ala Ala Phe Phe Pro Asn Tyr Asp Asn Arg Arg Tyr Pro Ile
                    245                 250                 255

CAG CCA GTT GGT CAA CTA ACA AGG GAA GTT TAT ACG GAC CCA TTA ATT          816
Gln Pro Val Gly Gln Leu Thr Arg Glu Val Tyr Thr Asp Pro Leu Ile
                260                 265                 270

AAT TTT AAT CCA CAG TTA CAG TCT GTA GCT CAA TTA CCT ACT TTT AAC          864
Asn Phe Asn Pro Gln Leu Gln Ser Val Ala Gln Leu Pro Thr Phe Asn
            275                 280                 285

GTT ATG GAG AGC AGC GCA ATT AGA AAT CCT CAT TTA TTT GAT ATA TTG          912
Val Met Glu Ser Ser Ala Ile Arg Asn Pro His Leu Phe Asp Ile Leu
        290                 295                 300

AAT AAT CTT ACA ATC TTT ACG GAT TGG TTT AGT GTT GGA CGC AAT TTT          960
Asn Asn Leu Thr Ile Phe Thr Asp Trp Phe Ser Val Gly Arg Asn Phe
305                 310                 315                 320

TAT TGG GGA GGA CAT CGA GTA ATA TCT AGC CTT ATA GGA GGT GGT AAC         1008
Tyr Trp Gly Gly His Arg Val Ile Ser Ser Leu Ile Gly Gly Gly Asn
                    325                 330                 335

ATA ACA TCT CCT ATA TAT GGA AGA GAG GCG AAC CAG GAG CCT CCA AGA         1056
Ile Thr Ser Pro Ile Tyr Gly Arg Glu Ala Asn Gln Glu Pro Pro Arg
                340                 345                 350

TCC TTT ACT TTT AAT GGA CCG GTA TTT AGG ACT TTA TCA AAT CCT ACT         1104
Ser Phe Thr Phe Asn Gly Pro Val Phe Arg Thr Leu Ser Asn Pro Thr
            355                 360                 365

TTA CGA TTA TTA CAG CAA CCT TGG CCA GCG CCA CCA TTT AAT TTA CGT         1152
Leu Arg Leu Leu Gln Gln Pro Trp Pro Ala Pro Pro Phe Asn Leu Arg
        370                 375                 380

GGT GTT GAA GGA GTA GAA TTT TCT ACA CCT ACA AAT AGC TTT ACG TAT         1200
Gly Val Glu Gly Val Glu Phe Ser Thr Pro Thr Asn Ser Phe Thr Tyr
385                 390                 395                 400

CGA GGA AGA GGT ACG GTT GAT TCT TTA ACT GAA TTA CCG CCT GAG GAT         1248
Arg Gly Arg Gly Thr Val Asp Ser Leu Thr Glu Leu Pro Pro Glu Asp
                    405                 410                 415

AAT AGT GTG CCA CCT CGC GAA GGA TAT AGT CAT CGT TTA TGT CAT GCA         1296
Asn Ser Val Pro Pro Arg Glu Gly Tyr Ser His Arg Leu Cys His Ala
                420                 425                 430

ACT TTT GTT CAA AGA TCT GGA ACA CCT TTT TTA ACA ACT GGT GTA GTA         1344
Thr Phe Val Gln Arg Ser Gly Thr Pro Phe Leu Thr Thr Gly Val Val
            435                 440                 445

TTT TCT TGG ACG CAT CGT AGT GCA ACT CTT ACA AAT ACA ATT GAT CCA         1392
Phe Ser Trp Thr His Arg Ser Ala Thr Leu Thr Asn Thr Ile Asp Pro
        450                 455                 460

GAG AGA ATT AAT CAA ATA CCT TTA GTG AAA GGA TTT AGA GTT TGG GGG         1440
```

| | | |
|---|---|---|
| Glu Arg Ile Asn Gln Ile Pro Leu Val Lys Gly Phe Arg Val Trp Gly<br>465                          470                     475                    480 | | |
| GGC ACC TCT GTC ATT ACA GGA CCA GGA TTT ACA GGA GGG GAT ATC CTT<br>Gly Thr Ser Val Ile Thr Gly Pro Gly Phe Thr Gly Gly Asp Ile Leu<br>                        485                     490                     495 | 1488 |
| CGA AGA AAT ACC TTT GGT GAT TTT GTA TCT CTA CAA GTC AAT ATT AAT<br>Arg Arg Asn Thr Phe Gly Asp Phe Val Ser Leu Gln Val Asn Ile Asn<br>            500                     505                     510 | 1536 |
| TCA CCA ATT ACC CAA AGA TAC CGT TTA AGA TTT CGT TAC GCT TCC AGT<br>Ser Pro Ile Thr Gln Arg Tyr Arg Leu Arg Phe Arg Tyr Ala Ser Ser<br>            515                     520                     525 | 1584 |
| AGG GAT GCA CGA GTT ATA GTA TTA ACA GGA GCG GCA TCC ACA GGA GTG<br>Arg Asp Ala Arg Val Ile Val Leu Thr Gly Ala Ala Ser Thr Gly Val<br>530                          535                     540 | 1632 |
| GGA GGC CAA GTT AGT GTA AAT ATG CCT CTT CAG AAA ACT ATG GAA ATA<br>Gly Gly Gln Val Ser Val Asn Met Pro Leu Gln Lys Thr Met Glu Ile<br>545                        550                     555                     560 | 1680 |
| GGG GAG AAC TTA ACA TCT AGA ACA TTT AGA TAT ACC GAT TTT AGT AAT<br>Gly Glu Asn Leu Thr Ser Arg Thr Phe Arg Tyr Thr Asp Phe Ser Asn<br>                    565                     570                     575 | 1728 |
| CCT TTT TCA TTT AGA GCT AAT CCA GAT ATA ATT GGG ATA AGT GAA CAA<br>Pro Phe Ser Phe Arg Ala Asn Pro Asp Ile Ile Gly Ile Ser Glu Gln<br>            580                     585                     590 | 1776 |
| CCT CTA TTT GGT GCA GGT TCT ATT AGT AGC GGT GAA CTT TAT ATA GAT<br>Pro Leu Phe Gly Ala Gly Ser Ile Ser Ser Gly Glu Leu Tyr Ile Asp<br>              595                     600                     605 | 1824 |
| AAA ATT GAA ATT ATT CTA GCA GAT GCA ACA TTT GAA GCA GAA TCT GAT<br>Lys Ile Glu Ile Ile Leu Ala Asp Ala Thr Phe Glu Ala Glu Ser Asp<br>610                          615                     620 | 1872 |
| TTA GAA AGA GCA CAA AAG GCG GTG AAT GCC CTG TTT ACT TCT TCC AAT<br>Leu Glu Arg Ala Gln Lys Ala Val Asn Ala Leu Phe Thr Ser Ser Asn<br>625                        630                     635                    640 | 1920 |
| CAA ATC GGG TTA AAA ACC GAT GTG ACG GAT TAT CAT ATT GAT CAA GTA<br>Gln Ile Gly Leu Lys Thr Asp Val Thr Asp Tyr His Ile Asp Gln Val<br>              645                     650                     655 | 1968 |
| TCC AAT TTA GTG GAT TGT TTA TCA GAT GAA TTT TGT CTG GAT GAA AAG<br>Ser Asn Leu Val Asp Cys Leu Ser Asp Glu Phe Cys Leu Asp Glu Lys<br>                660                     665                     670 | 2016 |
| CGA GAA TTG TCC GAG AAA GTC AAA CAT GCG AAG CGA CTC AGT GAT GAG<br>Arg Glu Leu Ser Glu Lys Val Lys His Ala Lys Arg Leu Ser Asp Glu<br>            675                     680                     685 | 2064 |
| CGG AAT TTA CTT CAA GAT CCA AAC TTC AGA GGG ATC AAT AGA CAA CCA<br>Arg Asn Leu Leu Gln Asp Pro Asn Phe Arg Gly Ile Asn Arg Gln Pro<br>            690                     695                     700 | 2112 |
| GAC CGT GGC TGG AGA GGA AGT ACA GAT ATT ACC ATC CAA GGA GGA GAT<br>Asp Arg Gly Trp Arg Gly Ser Thr Asp Ile Thr Ile Gln Gly Gly Asp<br>705                          710                     715                    720 | 2160 |
| GAC GTA TTC AAA GAG AAT TAC GTC ACA CTA CCG GGT ACC GTT GAT GAG<br>Asp Val Phe Lys Glu Asn Tyr Val Thr Leu Pro Gly Thr Val Asp Glu<br>              725                     730                     735 | 2208 |
| TGC TAT CCA ACG TAT TTA TAT CAG AAA ATA GAT GAG TCG AAA TTA AAA<br>Cys Tyr Pro Thr Tyr Leu Tyr Gln Lys Ile Asp Glu Ser Lys Leu Lys<br>            740                     745                     750 | 2256 |
| GCT TAT ACC CGT TAT GAA TTA AGA GGG TAT ATC GAA GAT AGT CAA GAC<br>Ala Tyr Thr Arg Tyr Glu Leu Arg Gly Tyr Ile Glu Asp Ser Gln Asp<br>              755                     760                     765 | 2304 |
| TTA GAA ATC TAT TTG ATC CGT TAC AAT GCA AAA CAC GAA ATA GTA AAT<br>Leu Glu Ile Tyr Leu Ile Arg Tyr Asn Ala Lys His Glu Ile Val Asn<br>        770                     775                     780 | 2352 |

```
                                                          -continued

GTG CCA GGC ACG GGT TCC TTA TGG CCG CTT TCA GCC CAA AGT CCA ATC        2400
Val Pro Gly Thr Gly Ser Leu Trp Pro Leu Ser Ala Gln Ser Pro Ile
785                 790                 795                 800

GGA AAG TGT GGA GAA CCG AAT CGA TGC GCG CCA CAC CTT GAA TGG AAT        2448
Gly Lys Cys Gly Glu Pro Asn Arg Cys Ala Pro His Leu Glu Trp Asn
                805                 810                 815

CCT GAT CTA GAT TGT TCC TGC AGA GAC GGG GAA AAA TGT GCA CAT CAT        2496
Pro Asp Leu Asp Cys Ser Cys Arg Asp Gly Glu Lys Cys Ala His His
        820                 825                 830

TCC CAT CAT TTC ACC TTG GAT ATT GAT GTT GGA TGT ACA GAC TTA AAT        2544
Ser His His Phe Thr Leu Asp Ile Asp Val Gly Cys Thr Asp Leu Asn
            835                 840                 845

GAG GAC TTA GGT GTA TGG GTG ATA TTC AAG ATT AAG ACG CAA GAT GGC        2592
Glu Asp Leu Gly Val Trp Val Ile Phe Lys Ile Lys Thr Gln Asp Gly
850                 855                 860

CAT GCA AGA CTA GGG AAT CTA GAG TTT CTC GAA GAG AAA CCA TTA TTA        2640
His Ala Arg Leu Gly Asn Leu Glu Phe Leu Glu Glu Lys Pro Leu Leu
865                 870                 875                 880

GGG GAA GCA CTA GCT CGT GTG AAA AGA GCG GAG AAG AAG TGG AGA GAC        2688
Gly Glu Ala Leu Ala Arg Val Lys Arg Ala Glu Lys Lys Trp Arg Asp
                885                 890                 895

AAA CGA GAG AAA CTG CAG TTG GAA ACA AAT ATT GTT TAT AAA GAG GCA        2736
Lys Arg Glu Lys Leu Gln Leu Glu Thr Asn Ile Val Tyr Lys Glu Ala
        900                 905                 910

AAA GAA TCT GTA GAT GCT TTA TTT GTA AAC TCT CAA TAT GAT AGA TTA        2784
Lys Glu Ser Val Asp Ala Leu Phe Val Asn Ser Gln Tyr Asp Arg Leu
            915                 920                 925

CAA GTG GAT ACG AAC ATC GCG ATG ATT CAT GCG GCA GAT AAA CGC GTT        2832
Gln Val Asp Thr Asn Ile Ala Met Ile His Ala Ala Asp Lys Arg Val
930                 935                 940

CAT AGA ATC CGG GAA GCG TAT CTG CCA GAG TTG TCT GTG ATT CCA GGT        2880
His Arg Ile Arg Glu Ala Tyr Leu Pro Glu Leu Ser Val Ile Pro Gly
945                 950                 955                 960

GTC AAT GCG GCC ATT TTC GAA GAA TTA GAG GGA CGT ATT TTT ACA GCG        2928
Val Asn Ala Ala Ile Phe Glu Glu Leu Glu Gly Arg Ile Phe Thr Ala
                965                 970                 975

TAT TCC TTA TAT GAT GCG AGA AAT GTC ATT AAA AAT GGC GAT TTC AAT        2976
Tyr Ser Leu Tyr Asp Ala Arg Asn Val Ile Lys Asn Gly Asp Phe Asn
        980                 985                 990

AAT GGC TTA TTA TGC TGG AAC GTG AAA GGT CAT GTA GAT GTA GAA GAG        3024
Asn Gly Leu Leu Cys Trp Asn Val Lys Gly His Val Asp Val Glu Glu
            995                 1000                1005

CAA AAC AAC CAC CGT TCG GTC CTT GTT ATC CCA GAA TGG GAG GCA GAA        3072
Gln Asn Asn His Arg Ser Val Leu Val Ile Pro Glu Trp Glu Ala Glu
1010                1015                1020

GTG TCA CAA GAG GTT CGT GTC TGT CCA GGT CGT GGC TAT ATC CTT CGT        3120
Val Ser Gln Glu Val Arg Val Cys Pro Gly Arg Gly Tyr Ile Leu Arg
1025                1030                1035                1040

GTC ACA GCA TAT AAA GAG GGA TAT GGA GAG GGC TGC GTA ACG ATC CAT        3168
Val Thr Ala Tyr Lys Glu Gly Tyr Gly Glu Gly Cys Val Thr Ile His
                1045                1050                1055

GAG ATC GAA GAC AAT ACA GAC GAA CTG AAA TTC AGC AAC TGT GTA GAA        3216
Glu Ile Glu Asp Asn Thr Asp Glu Leu Lys Phe Ser Asn Cys Val Glu
        1060                1065                1070

GAG GAA GTA TAT CCA AAC AAC ACA GTA ACG TGT AAT AAT TAT ACT GGG        3264
Glu Glu Val Tyr Pro Asn Asn Thr Val Thr Cys Asn Asn Tyr Thr Gly
            1075                1080                1085

ACT CAA GAA GAA TAT GAG GGT ACG TAC ACT TCT CGT AAT CAA GGA TAT        3312
Thr Gln Glu Glu Tyr Glu Gly Thr Tyr Thr Ser Arg Asn Gln Gly Tyr
1090                1095                1100
```

-continued

```
GAC GAA GCC TAT GGT AAT AAC CCT TCC GTA CCA GCT GAT TAC GCT TCA      3360
Asp Glu Ala Tyr Gly Asn Asn Pro Ser Val Pro Ala Asp Tyr Ala Ser
1105                1110                1115                1120

GTC TAT GAA GAA AAA TCG TAT ACA GAT GGA CGA AGA GAG AAT CCT TGT      3408
Val Tyr Glu Glu Lys Ser Tyr Thr Asp Gly Arg Arg Glu Asn Pro Cys
                1125                1130                1135

GAA TCT AAC AGA GGC TAT GGG GAT TAC ACA CCA CTA CCG GCT GGT TAT      3456
Glu Ser Asn Arg Gly Tyr Gly Asp Tyr Thr Pro Leu Pro Ala Gly Tyr
            1140                1145                1150

GTA ACA AAG GAT TTA GAG TAC TTC CCA GAG ACC GAT AAG GTA TGG ATT      3504
Val Thr Lys Asp Leu Glu Tyr Phe Pro Glu Thr Asp Lys Val Trp Ile
        1155                1160                1165

GAG ATC GGA GAA ACA GAA GGA ACA TTC ATC GTG GAT AGC GTG GAA TTA      3552
Glu Ile Gly Glu Thr Glu Gly Thr Phe Ile Val Asp Ser Val Glu Leu
1170                1175                1180

CTC CTT ATG GAG GAA                                                   3567
Leu Leu Met Glu Glu
1185
```

(2) INFORMATION FOR SEQ ID NO: 2:

(i) SEQUENCE CHARACTERISTICS:
        (A) LENGTH: 1189 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Glu Glu Asn Asn Gln Asn Gln Cys Ile Pro Tyr Asn Cys Leu Ser
1               5                   10                  15

Asn Pro Glu Glu Val Leu Leu Asp Gly Glu Arg Ile Ser Thr Gly Asn
            20                  25                  30

Ser Ser Ile Asp Ile Ser Leu Ser Leu Val Gln Phe Leu Val Ser Asn
        35                  40                  45

Phe Val Pro Gly Gly Gly Phe Leu Val Gly Leu Ile Asp Phe Val Trp
    50                  55                  60

Gly Ile Val Gly Pro Ser Gln Trp Asp Ala Phe Leu Val Gln Ile Glu
65                  70                  75                  80

Gln Leu Ile Asn Glu Arg Ile Ala Glu Phe Ala Arg Asn Ala Ala Ile
                85                  90                  95

Ala Asn Leu Glu Gly Leu Gly Asn Asn Phe Asn Ile Tyr Val Glu Ala
            100                 105                 110

Phe Lys Glu Trp Glu Glu Asp Pro Asn Asn Pro Glu Thr Arg Thr Arg
        115                 120                 125

Val Ile Asp Arg Phe Arg Ile Leu Asp Gly Leu Leu Glu Arg Asp Ile
    130                 135                 140

Pro Ser Phe Arg Ile Ser Gly Phe Glu Val Pro Leu Leu Ser Val Tyr
145                 150                 155                 160

Ala Gln Ala Ala Asn Leu His Leu Ala Ile Leu Arg Asp Ser Val Ile
                165                 170                 175

Phe Gly Glu Arg Trp Gly Leu Thr Thr Ile Asn Val Asn Glu Asn Tyr
            180                 185                 190

Asn Arg Leu Ile Arg His Ile Asp Glu Tyr Ala Asp His Cys Ala Asn
        195                 200                 205

Thr Tyr Asn Arg Gly Leu Asn Asn Leu Pro Lys Ser Thr Tyr Gln Asp
    210                 215                 220
```

-continued

```
Trp Ile Thr Tyr Asn Arg Leu Arg Arg Asp Leu Thr Leu Thr Val Leu
225                 230                 235                 240

Asp Ile Ala Ala Phe Phe Pro Asn Tyr Asp Asn Arg Arg Tyr Pro Ile
                245                 250                 255

Gln Pro Val Gly Gln Leu Thr Arg Glu Val Tyr Thr Asp Pro Leu Ile
            260                 265                 270

Asn Phe Asn Pro Gln Leu Gln Ser Val Ala Gln Leu Pro Thr Phe Asn
        275                 280                 285

Val Met Glu Ser Ser Ala Ile Arg Asn Pro His Leu Phe Asp Ile Leu
    290                 295                 300

Asn Asn Leu Thr Ile Phe Thr Asp Trp Phe Ser Val Gly Arg Asn Phe
305                 310                 315                 320

Tyr Trp Gly Gly His Arg Val Ile Ser Ser Leu Ile Gly Gly Gly Asn
                325                 330                 335

Ile Thr Ser Pro Ile Tyr Gly Arg Glu Ala Asn Gln Glu Pro Pro Arg
            340                 345                 350

Ser Phe Thr Phe Asn Gly Pro Val Phe Arg Thr Leu Ser Asn Pro Thr
        355                 360                 365

Leu Arg Leu Leu Gln Gln Pro Trp Pro Ala Pro Pro Phe Asn Leu Arg
    370                 375                 380

Gly Val Glu Gly Val Glu Phe Ser Thr Pro Thr Asn Ser Phe Thr Tyr
385                 390                 395                 400

Arg Gly Arg Gly Thr Val Asp Ser Leu Thr Glu Leu Pro Pro Glu Asp
                405                 410                 415

Asn Ser Val Pro Pro Arg Glu Gly Tyr Ser His Arg Leu Cys His Ala
            420                 425                 430

Thr Phe Val Gln Arg Ser Gly Thr Pro Phe Leu Thr Thr Gly Val Val
        435                 440                 445

Phe Ser Trp Thr His Arg Ser Ala Thr Leu Thr Asn Thr Ile Asp Pro
    450                 455                 460

Glu Arg Ile Asn Gln Ile Pro Leu Val Lys Gly Phe Arg Val Trp Gly
465                 470                 475                 480

Gly Thr Ser Val Ile Thr Gly Pro Gly Phe Thr Gly Gly Asp Ile Leu
                485                 490                 495

Arg Arg Asn Thr Phe Gly Asp Phe Val Ser Leu Gln Val Asn Ile Asn
            500                 505                 510

Ser Pro Ile Thr Gln Arg Tyr Arg Leu Arg Phe Arg Tyr Ala Ser Ser
        515                 520                 525

Arg Asp Ala Arg Val Ile Val Leu Thr Gly Ala Ala Ser Thr Gly Val
    530                 535                 540

Gly Gly Gln Val Ser Val Asn Met Pro Leu Gln Lys Thr Met Glu Ile
545                 550                 555                 560

Gly Glu Asn Leu Thr Ser Arg Thr Phe Arg Tyr Thr Asp Phe Ser Asn
                565                 570                 575

Pro Phe Ser Phe Arg Ala Asn Pro Asp Ile Ile Gly Ile Ser Glu Gln
            580                 585                 590

Pro Leu Phe Gly Ala Gly Ser Ile Ser Ser Gly Glu Leu Tyr Ile Asp
        595                 600                 605

Lys Ile Glu Ile Ile Leu Ala Asp Ala Thr Phe Glu Ala Glu Ser Asp
    610                 615                 620

Leu Glu Arg Ala Gln Lys Ala Val Asn Ala Leu Phe Thr Ser Ser Asn
625                 630                 635                 640

Gln Ile Gly Leu Lys Thr Asp Val Thr Asp Tyr His Ile Asp Gln Val
```

-continued

```
                645                 650                 655
Ser Asn Leu Val Asp Cys Leu Ser Asp Glu Phe Cys Leu Asp Glu Lys
            660                 665                 670
Arg Glu Leu Ser Glu Lys Val Lys His Ala Lys Arg Leu Ser Asp Glu
            675                 680                 685
Arg Asn Leu Leu Gln Asp Pro Asn Phe Arg Gly Ile Asn Arg Gln Pro
            690                 695                 700
Asp Arg Gly Trp Arg Gly Ser Thr Asp Ile Thr Ile Gln Gly Gly Asp
705                 710                 715                 720
Asp Val Phe Lys Glu Asn Tyr Val Thr Leu Pro Gly Thr Val Asp Glu
            725                 730                 735
Cys Tyr Pro Thr Tyr Leu Tyr Gln Lys Ile Asp Glu Ser Lys Leu Lys
            740                 745                 750
Ala Tyr Thr Arg Tyr Glu Leu Arg Gly Tyr Ile Glu Asp Ser Gln Asp
            755                 760                 765
Leu Glu Ile Tyr Leu Ile Arg Tyr Asn Ala Lys His Glu Ile Val Asn
            770                 775                 780
Val Pro Gly Thr Gly Ser Leu Trp Pro Leu Ser Ala Gln Ser Pro Ile
785                 790                 795                 800
Gly Lys Cys Gly Glu Pro Asn Arg Cys Ala Pro His Leu Glu Trp Asn
            805                 810                 815
Pro Asp Leu Asp Cys Ser Cys Arg Asp Gly Glu Lys Cys Ala His His
            820                 825                 830
Ser His His Phe Thr Leu Asp Ile Asp Val Gly Cys Thr Asp Leu Asn
            835                 840                 845
Glu Asp Leu Gly Val Trp Val Ile Phe Lys Ile Lys Thr Gln Asp Gly
850                 855                 860
His Ala Arg Leu Gly Asn Leu Glu Phe Leu Glu Glu Lys Pro Leu Leu
865                 870                 875                 880
Gly Glu Ala Leu Ala Arg Val Lys Arg Ala Glu Lys Lys Trp Arg Asp
            885                 890                 895
Lys Arg Glu Lys Leu Gln Leu Glu Thr Asn Ile Val Tyr Lys Glu Ala
            900                 905                 910
Lys Glu Ser Val Asp Ala Leu Phe Val Asn Ser Gln Tyr Asp Arg Leu
            915                 920                 925
Gln Val Asp Thr Asn Ile Ala Met Ile His Ala Ala Asp Lys Arg Val
            930                 935                 940
His Arg Ile Arg Glu Ala Tyr Leu Pro Glu Leu Ser Val Ile Pro Gly
945                 950                 955                 960
Val Asn Ala Ala Ile Phe Glu Glu Leu Glu Gly Arg Ile Phe Thr Ala
            965                 970                 975
Tyr Ser Leu Tyr Asp Ala Arg Asn Val Ile Lys Asn Gly Asp Phe Asn
            980                 985                 990
Asn Gly Leu Leu Cys Trp Asn Val Lys Gly His Val Asp Val Glu Glu
            995                 1000                1005
Gln Asn Asn His Arg Ser Val Leu Val Ile Pro Glu Trp Glu Ala Glu
            1010                1015                1020
Val Ser Gln Glu Val Arg Val Cys Pro Gly Arg Gly Tyr Ile Leu Arg
1025                1030                1035                1040
Val Thr Ala Tyr Lys Glu Gly Tyr Gly Glu Gly Cys Val Thr Ile His
            1045                1050                1055
Glu Ile Glu Asp Asn Thr Asp Glu Leu Lys Phe Ser Asn Cys Val Glu
            1060                1065                1070
```

```
Glu Glu Val Tyr Pro Asn Asn Thr Val Thr Cys Asn Asn Tyr Thr Gly
        1075                1080                1085

Thr Gln Glu Glu Tyr Glu Gly Thr Tyr Thr Ser Arg Asn Gln Gly Tyr
        1090                1095                1100

Asp Glu Ala Tyr Gly Asn Asn Pro Ser Val Pro Ala Asp Tyr Ala Ser
1105                1110                1115                1120

Val Tyr Glu Glu Lys Ser Tyr Thr Asp Gly Arg Arg Glu Asn Pro Cys
            1125                1130                1135

Glu Ser Asn Arg Gly Tyr Gly Asp Tyr Thr Pro Leu Pro Ala Gly Tyr
            1140                1145                1150

Val Thr Lys Asp Leu Glu Tyr Phe Pro Glu Thr Asp Lys Val Trp Ile
        1155                1160                1165

Glu Ile Gly Glu Thr Glu Gly Thr Phe Ile Val Asp Ser Val Glu Leu
        1170                1175                1180

Leu Leu Met Glu Glu
1185

(2) INFORMATION FOR SEQ ID NO: 3:

(i) SEQUENCE CHARACTERISTICS:
        (A) LENGTH: 3513 base pairs
        (B) TYPE: nucleic acid
        (C) STRANDEDNESS: single
        (D) TOPOLOGY: unknown (ii) MOLECULE TYPE: cDNA (iii) HYPOTHETICAL: NO (iv) ANTI-SENSE: NO (vi) ORIGINAL SOURCE:
         (A) ORGANISM: Bacillus thuringiensis (ix) FEATURE:
         (A) NAME/KEY: CDS
         (B) LOCATION: 1..3513

(xi) SEQUENCE DESCRIPTION: SEQ ID NO: 3:

ATG GAG ATA GTG AAT AAT CAG AAT CAA TGC GTG CCT TAT AAT TGT TTA        48
Met Glu Ile Val Asn Asn Gln Asn Gln Cys Val Pro Tyr Asn Cys Leu
 1               5                  10                  15

AAT AAT CCT GAA AAT GAG ATA TTA GAT ATT GAA AGG TCA AAT AGT ACT        96
Asn Asn Pro Glu Asn Glu Ile Leu Asp Ile Glu Arg Ser Asn Ser Thr
                20                  25                  30

GTA GCA ACA AAC ATC GCC TTG GAG ATT AGT CGT CTG CTC GCT TCC GCA       144
Val Ala Thr Asn Ile Ala Leu Glu Ile Ser Arg Leu Leu Ala Ser Ala
         35                  40                  45

ACT CCA ATA GGG GGG ATT TTA TTA GGA TTG TTT GAT GCA ATA TGG GGG       192
Thr Pro Ile Gly Gly Ile Leu Leu Gly Leu Phe Asp Ala Ile Trp Gly
     50                  55                  60

TCT ATA GGC CCT TCA CAA TGG GAT TTA TTT TTA GAG CAA ATT GAG CTA       240
Ser Ile Gly Pro Ser Gln Trp Asp Leu Phe Leu Glu Gln Ile Glu Leu
 65                  70                  75                  80

TTG ATT GAC CAA AAA ATA GAG GAA TTC GCT AGA AAC CAG GCA ATT TCT       288
Leu Ile Asp Gln Lys Ile Glu Glu Phe Ala Arg Asn Gln Ala Ile Ser
                85                  90                  95

AGA TTG GAA GGG ATA AGC AGT CTG TAC GGA ATT TAT ACA GAA GCT TTT       336
Arg Leu Glu Gly Ile Ser Ser Leu Tyr Gly Ile Tyr Thr Glu Ala Phe
                100                 105                 110

AGA GAG TGG GAA GCA GAT CCT ACT AAT CCA GCA TTA AAA GAA GAG ATG       384
Arg Glu Trp Glu Ala Asp Pro Thr Asn Pro Ala Leu Lys Glu Glu Met
```

|  |  |  |  |  |  |  |  |  |  |  |  |  |  |  |  |
|---|---|---|---|---|---|---|---|---|---|---|---|---|---|---|---|
|  | 115 |  |  |  | 120 |  |  |  |  | 125 |  |  |  |  |  |

```
CGT ACT CAA TTT AAT GAC ATG AAC AGT ATT CTT GTA ACA GCT ATT CCT         432
Arg Thr Gln Phe Asn Asp Met Asn Ser Ile Leu Val Thr Ala Ile Pro
    130                 135                 140

CTT TTT TCA GTT CAA AAT TAT CAA GTC CCA TTT TTA TCA GTA TAT GTT         480
Leu Phe Ser Val Gln Asn Tyr Gln Val Pro Phe Leu Ser Val Tyr Val
145                 150                 155                 160

CAA GCT GCA AAT TTA CAT TTA TCG GTT TTG AGA GAT GTT TCA GTG TTT         528
Gln Ala Ala Asn Leu His Leu Ser Val Leu Arg Asp Val Ser Val Phe
                165                 170                 175

GGG CAG GCT TGG GGA TTT GAT ATA GCA ACA ATA AAT AGT CGT TAT AAT         576
Gly Gln Ala Trp Gly Phe Asp Ile Ala Thr Ile Asn Ser Arg Tyr Asn
            180                 185                 190

GAT CTG ACT AGA CTT ATT CCT ATA TAT ACA GAT TAT GCT GTA CGC TGG         624
Asp Leu Thr Arg Leu Ile Pro Ile Tyr Thr Asp Tyr Ala Val Arg Trp
        195                 200                 205

TAC AAT ACG GGA TTA GAT CGC TTA CCA CGA ACT GGT GGG CTG CGA AAC         672
Tyr Asn Thr Gly Leu Asp Arg Leu Pro Arg Thr Gly Gly Leu Arg Asn
    210                 215                 220

TGG GCA AGA TTT AAT CAG TTT AGA AGA GAG TTA ACA ATA TCA GTA TTA         720
Trp Ala Arg Phe Asn Gln Phe Arg Arg Glu Leu Thr Ile Ser Val Leu
225                 230                 235                 240

GAT ATT ATT TCT TTT TTC AGA AAT TAC GAT TCT AGA TTA TAT CCA ATT         768
Asp Ile Ile Ser Phe Phe Arg Asn Tyr Asp Ser Arg Leu Tyr Pro Ile
                245                 250                 255

CCA ACA AGC TCC CAA TTA ACG CGG GAA GTA TAT ACA GAT CCG GTA ATT         816
Pro Thr Ser Ser Gln Leu Thr Arg Glu Val Tyr Thr Asp Pro Val Ile
            260                 265                 270

AAT ATA ACT GAC TAT AGA GTT GGC CCC AGC TTC GAG AAT ATT GAG AAC         864
Asn Ile Thr Asp Tyr Arg Val Gly Pro Ser Phe Glu Asn Ile Glu Asn
        275                 280                 285

TCA GCC ATT AGA AGC CCC CAC CTT ATG GAC TTC TTA AAT AAT TTG ACC         912
Ser Ala Ile Arg Ser Pro His Leu Met Asp Phe Leu Asn Asn Leu Thr
    290                 295                 300

ATT GAT ACG GAT TTG ATT AGA GGT GTT CAC TAT TGG GCA GGG CAT CGT         960
Ile Asp Thr Asp Leu Ile Arg Gly Val His Tyr Trp Ala Gly His Arg
305                 310                 315                 320

GTA ACT TCT CAT TTT ACA GGT AGT TCT CAA GTG ATA ACA ACC CCT CAA        1008
Val Thr Ser His Phe Thr Gly Ser Ser Gln Val Ile Thr Thr Pro Gln
                325                 330                 335

TAT GGG ATA ACC GCA AAT GCG GAA CCA AGA CGA ACT ATT GCT CCT AGT        1056
Tyr Gly Ile Thr Ala Asn Ala Glu Pro Arg Arg Thr Ile Ala Pro Ser
            340                 345                 350

ACT TTT CCA GGT CTT AAC CTA TTT TAT AGA ACA TTA TCA AAT CCT TTC        1104
Thr Phe Pro Gly Leu Asn Leu Phe Tyr Arg Thr Leu Ser Asn Pro Phe
        355                 360                 365

TTC CGA AGA TCA GAA AAT ATT ACT CCT ACC TTA GGG ATA AAT GTA GTA        1152
Phe Arg Arg Ser Glu Asn Ile Thr Pro Thr Leu Gly Ile Asn Val Val
    370                 375                 380

CAG GGA GTA GGG TTC ATT CAA CCA AAT AAT GCT GAA GTT CTA TAT AGA        1200
Gln Gly Val Gly Phe Ile Gln Pro Asn Asn Ala Glu Val Leu Tyr Arg
385                 390                 395                 400

AGT AGG GGG ACA GTA GAT TCT CTT AAT GAG TTA CCA ATT GAT GGT GAG        1248
Ser Arg Gly Thr Val Asp Ser Leu Asn Glu Leu Pro Ile Asp Gly Glu
                405                 410                 415

AAT TCA TTA GTT GGA TAT AGT CAT CGA TTA AGT CAT GTT ACA CTA ACC        1296
Asn Ser Leu Val Gly Tyr Ser His Arg Leu Ser His Val Thr Leu Thr
            420                 425                 430

AGG TCG TTA TAT AAT ACT AAT ATA ACT AGC CTG CCA ACA TTT GTT TGG        1344
```

-continued

```
                Arg Ser Leu Tyr Asn Thr Asn Ile Thr Ser Leu Pro Thr Phe Val Trp
                        435                 440                 445

ACA CAT CAC AGT GCT ACT AAT ACA AAT ACA ATT AAT CCA GAT ATT ATT              1392
Thr His His Ser Ala Thr Asn Thr Asn Thr Ile Asn Pro Asp Ile Ile
        450                 455                 460

ACA CAA ATA CCT TTA GTG AAA GGA TTT AGA CTT GGT GGT GGC ACC TCT              1440
Thr Gln Ile Pro Leu Val Lys Gly Phe Arg Leu Gly Gly Gly Thr Ser
465                 470                 475                 480

GTC ATT AAA GGA CCA GGA TTT ACA GGA GGG GAT ATC CTT CGA AGA AAT              1488
Val Ile Lys Gly Pro Gly Phe Thr Gly Gly Asp Ile Leu Arg Arg Asn
                485                 490                 495

ACC ATT GGT GAG TTT GTG TCT TTA CAA GTC AAT ATT AAC TCA CCA ATT              1536
Thr Ile Gly Glu Phe Val Ser Leu Gln Val Asn Ile Asn Ser Pro Ile
            500                 505                 510

ACC CAA AGA TAC CGT TTA AGA TTT CGT TAT GCT TCC AGT AGG GAT GCA              1584
Thr Gln Arg Tyr Arg Leu Arg Phe Arg Tyr Ala Ser Ser Arg Asp Ala
        515                 520                 525

CGA ATT ACT GTA GCG ATA GGA GGA CAA ATT AGA GTA GAT ATG ACC CTT              1632
Arg Ile Thr Val Ala Ile Gly Gly Gln Ile Arg Val Asp Met Thr Leu
    530                 535                 540

GAA AAA ACC ATG GAA ATT GGG GAG AGC TTA ACA TCT AGA ACA TTT AGC              1680
Glu Lys Thr Met Glu Ile Gly Glu Ser Leu Thr Ser Arg Thr Phe Ser
545                 550                 555                 560

TAT ACC AAT TTT AGT AAT CCT TTT TCA TTT AGG GCT AAT CCA GAT ATA              1728
Tyr Thr Asn Phe Ser Asn Pro Phe Ser Phe Arg Ala Asn Pro Asp Ile
                565                 570                 575

ATT AGA ATA GCT GAA GAA CTT CCT ATT CGT GGT GGT GAG CTT TAT ATA              1776
Ile Arg Ile Ala Glu Glu Leu Pro Ile Arg Gly Gly Glu Leu Tyr Ile
            580                 585                 590

GAT AAA ATT GAA CTT ATT CTA GCA GAT GCA ACA TTT GAA GAA GAA TAT              1824
Asp Lys Ile Glu Leu Ile Leu Ala Asp Ala Thr Phe Glu Glu Glu Tyr
        595                 600                 605

GAT TTG GAA AGA GCA CAG AAG GCG GTG AAT GCC CTG TTT ACT TCT ACA              1872
Asp Leu Glu Arg Ala Gln Lys Ala Val Asn Ala Leu Phe Thr Ser Thr
    610                 615                 620

AAT CAA CTA GGG CTA AAA ACA GAT GTG ACG GAT TAT CAT ATT GAT CAA              1920
Asn Gln Leu Gly Leu Lys Thr Asp Val Thr Asp Tyr His Ile Asp Gln
625                 630                 635                 640

GTT TCC AAT TTA GTT GAG TGT TTA TCG GAT GAA TTT TGT CTG GAT GAA              1968
Val Ser Asn Leu Val Glu Cys Leu Ser Asp Glu Phe Cys Leu Asp Glu
                645                 650                 655

AAG AGA GAA TTA TCC GAG AAA GTC AAA CAT GCG AAG CGA CTC AGT GAT              2016
Lys Arg Glu Leu Ser Glu Lys Val Lys His Ala Lys Arg Leu Ser Asp
            660                 665                 670

GAA CGG AAT TTA CTT CAA GAT CCA AAC TTC AGA GGG ATC AAT AGG CAA              2064
Glu Arg Asn Leu Leu Gln Asp Pro Asn Phe Arg Gly Ile Asn Arg Gln
        675                 680                 685

CCA GAC CGT GGC TGG AGA GGA AGC ACG GAT ATT ACT ATC CAA GGT GGA              2112
Pro Asp Arg Gly Trp Arg Gly Ser Thr Asp Ile Thr Ile Gln Gly Gly
    690                 695                 700

GAT GAC GTA TTC AAA GAG AAT TAC GTC ACA TTA CCG GGT ACC TTT GAT              2160
Asp Asp Val Phe Lys Glu Asn Tyr Val Thr Leu Pro Gly Thr Phe Asp
705                 710                 715                 720

GAG TGC TAT CCA ACG TAT TTA TAT CAA AAA ATA GAT GAG TCG AAG TTA              2208
Glu Cys Tyr Pro Thr Tyr Leu Tyr Gln Lys Ile Asp Glu Ser Lys Leu
                725                 730                 735

AAA GCT TAT ACC CGC TAT GAA TTA AGA GGG TAT ATC GAG GAT AGT CAA              2256
Lys Ala Tyr Thr Arg Tyr Glu Leu Arg Gly Tyr Ile Glu Asp Ser Gln
            740                 745                 750
```

-continued

```
GAC TTA GAA ATC TAT TTA ATT CGC TAC AAT GCA AAA CAC GAG ACA GTA      2304
Asp Leu Glu Ile Tyr Leu Ile Arg Tyr Asn Ala Lys His Glu Thr Val
            755                 760                 765

AAC GTG CCA GGT ACG GGT TCC TTA TGG CCG CTT TCA GCC CAA AGT CCA      2352
Asn Val Pro Gly Thr Gly Ser Leu Trp Pro Leu Ser Ala Gln Ser Pro
770                 775                 780

ATC GGA AAG TGT GGA GAA CCG AAT CGA TGC GCG CCA CAC CTT GAA TGG      2400
Ile Gly Lys Cys Gly Glu Pro Asn Arg Cys Ala Pro His Leu Glu Trp
785                 790                 795                 800

AAT CCT AAT CTA GAT TGC TCC TGC AGA GAC GGG GAA AAA TGT GCC CAT      2448
Asn Pro Asn Leu Asp Cys Ser Cys Arg Asp Gly Glu Lys Cys Ala His
            805                 810                 815

CAT TCC CAT CAT TTC TCC TTG GAC ATT GAT GTT GGA TGT ACA GAC TTA      2496
His Ser His His Phe Ser Leu Asp Ile Asp Val Gly Cys Thr Asp Leu
                820                 825                 830

AAT GAG GAC TTA GGT GTA TGG GTG ATA TTC AAG ATT AAG ACA CAA GAT      2544
Asn Glu Asp Leu Gly Val Trp Val Ile Phe Lys Ile Lys Thr Gln Asp
            835                 840                 845

GGC TAT GCA AGA CTA GGA AAT CTA GAG TTT CTC GAA GAG AAC CCA CTA      2592
Gly Tyr Ala Arg Leu Gly Asn Leu Glu Phe Leu Glu Glu Asn Pro Leu
850                 855                 860

TTA GGG GAA GCA CTA GCT CGT GTG AAA AGA GCG GAG AAA AAA TGG AGA      2640
Leu Gly Glu Ala Leu Ala Arg Val Lys Arg Ala Glu Lys Lys Trp Arg
865                 870                 875                 880

GAC AAA TGC GAA AAA TTG GAA TGG GAA ACA AAT ATT GTT TAT AAA GAG      2688
Asp Lys Cys Glu Lys Leu Glu Trp Glu Thr Asn Ile Val Tyr Lys Glu
            885                 890                 895

GCA AAA GAA TCT GTA GAT GCT TTA TTT GTA AAC TCT CAA TAT GAT AGA      2736
Ala Lys Glu Ser Val Asp Ala Leu Phe Val Asn Ser Gln Tyr Asp Arg
900                 905                 910

TTA CAA GCG GAT ACG AAT ATC GCG ATG ATT CAT GCG GCA GAT AAA CGC      2784
Leu Gln Ala Asp Thr Asn Ile Ala Met Ile His Ala Ala Asp Lys Arg
            915                 920                 925

GTT CAT AGC ATT CGA GAA GCG TAT CTG CCA GAG CTG TCT GTG ATT CCG      2832
Val His Ser Ile Arg Glu Ala Tyr Leu Pro Glu Leu Ser Val Ile Pro
                930                 935                 940

GGT GTC AAT GCG GCT ATT TTT GAA GAA TTA GAA GGG CGT ATT TTC ACT      2880
Gly Val Asn Ala Ala Ile Phe Glu Glu Leu Glu Gly Arg Ile Phe Thr
945                 950                 955                 960

GCA TTC TCC CTA TAT GAT GCG AGA AAT GTC ATT AAA AAT GGC GAT TTC      2928
Ala Phe Ser Leu Tyr Asp Ala Arg Asn Val Ile Lys Asn Gly Asp Phe
                965                 970                 975

AAT AAT GGC TTA TCA TGC TGG AAC GTG AAA GGG CAT GTA GAT GTA GAA      2976
Asn Asn Gly Leu Ser Cys Trp Asn Val Lys Gly His Val Asp Val Glu
            980                 985                 990

GAA CAG AAC AAC CAT CGT TCG GTC CTT GTT GTT CCA GAA TGG GAA GCA      3024
Glu Gln Asn Asn His Arg Ser Val Leu Val Val Pro Glu Trp Glu Ala
            995                 1000                1005

GAA GTG TCA CAA GAA GTT CGT GTT TGT CCG GGT CGT GGC TAT ATC CTT      3072
Glu Val Ser Gln Glu Val Arg Val Cys Pro Gly Arg Gly Tyr Ile Leu
        1010                1015                1020

CGT GTT ACA GCG TAC AAA GAG GGA TAT GGA GAG GGC TGT GTA ACG ATT      3120
Arg Val Thr Ala Tyr Lys Glu Gly Tyr Gly Glu Gly Cys Val Thr Ile
1025                1030                1035                1040

CAT GAG ATC GAA GAC AAT ACA GAC GAA CTG AAA TTC AGC AAC TGT GTA      3168
His Glu Ile Glu Asp Asn Thr Asp Glu Leu Lys Phe Ser Asn Cys Val
                1045                1050                1055

GAA GAG GAA GTA TAT CCA AAC AAC ACG GTA ACG TGT AAT AAT TAT ACT      3216
Glu Glu Glu Val Tyr Pro Asn Asn Thr Val Thr Cys Asn Asn Tyr Thr
            1060                1065                1070
```

```
GCG ACT CAA GAA GAA CAT GAG GGT ACG TAC ACT TCC CGT AAT CGA GGA        3264
Ala Thr Gln Glu Glu His Glu Gly Thr Tyr Thr Ser Arg Asn Arg Gly
        1075                1080                1085

TAT GAC GAA GCC TAT GAA AGC AAT TCT TCT GTA CAT GCG TCA GTC TAT        3312
Tyr Asp Glu Ala Tyr Glu Ser Asn Ser Ser Val His Ala Ser Val Tyr
    1090                1095                1100

GAA GAA AAA TCG TAT ACA GAT AGA CGA AGA GAG AAT CCT TGT GAA TCT        3360
Glu Glu Lys Ser Tyr Thr Asp Arg Arg Arg Glu Asn Pro Cys Glu Ser
1105                1110                1115                1120

AAC AGA GGA TAT GGG GAT TAC ACA CCA CTA CCA GCT GGC TAT GTG ACA        3408
Asn Arg Gly Tyr Gly Asp Tyr Thr Pro Leu Pro Ala Gly Tyr Val Thr
            1125                1130                1135

AAA GAA TTA GAG TAC TTC CCA GAA ACC GAT AAG GTA TGG ATT GAG ATC        3456
Lys Glu Leu Glu Tyr Phe Pro Glu Thr Asp Lys Val Trp Ile Glu Ile
                1140                1145                1150

GGA GAA ACG GAA GGA ACA TTC ATC GTG GAC AGC GTG GAA TTA CTT CTT        3504
Gly Glu Thr Glu Gly Thr Phe Ile Val Asp Ser Val Glu Leu Leu Leu
            1155                1160                1165

ATG GAG GAA                                                            3513
Met Glu Glu
    1170
```

(2) INFORMATION FOR SEQ ID NO: 4:

(i) SEQUENCE CHARACTERISTICS:
        (A) LENGTH: 1171 amino acids
        (B) TYPE: amino acid
        (D) TOPOLOGY: linear (ii) MOLECULE TYPE: protein (xi) SEQUENCE DESCRIPTION: SEQ ID NO: 4:

```
Met Glu Ile Val Asn Asn Gln Asn Gln Cys Val Pro Tyr Asn Cys Leu
  1               5                  10                  15

Asn Asn Pro Glu Asn Glu Ile Leu Asp Ile Glu Arg Ser Asn Ser Thr
                20                  25                  30

Val Ala Thr Asn Ile Ala Leu Glu Ile Ser Arg Leu Leu Ala Ser Ala
            35                  40                  45

Thr Pro Ile Gly Gly Ile Leu Gly Leu Phe Asp Ala Ile Trp Gly
        50                  55                  60

Ser Ile Gly Pro Ser Gln Trp Asp Leu Phe Leu Glu Gln Ile Glu Leu
 65                  70                  75                  80

Leu Ile Asp Gln Lys Ile Glu Glu Phe Ala Arg Asn Gln Ala Ile Ser
                85                  90                  95

Arg Leu Glu Gly Ile Ser Ser Leu Tyr Gly Ile Tyr Thr Glu Ala Phe
            100                 105                 110

Arg Glu Trp Glu Ala Asp Pro Thr Asn Pro Ala Leu Lys Glu Glu Met
        115                 120                 125

Arg Thr Gln Phe Asn Asp Met Asn Ser Ile Leu Val Thr Ala Ile Pro
    130                 135                 140

Leu Phe Ser Val Gln Asn Tyr Gln Val Pro Phe Leu Ser Val Tyr Val
145                 150                 155                 160

Gln Ala Ala Asn Leu His Leu Ser Val Leu Arg Asp Val Ser Val Phe
                165                 170                 175

Gly Gln Ala Trp Gly Phe Asp Ile Ala Thr Ile Asn Ser Arg Tyr Asn
            180                 185                 190

Asp Leu Thr Arg Leu Ile Pro Ile Tyr Thr Asp Tyr Ala Val Arg Trp
        195                 200                 205
```

-continued

```
Tyr Asn Thr Gly Leu Asp Arg Leu Pro Arg Thr Gly Gly Leu Arg Asn
    210                 215                 220

Trp Ala Arg Phe Asn Gln Phe Arg Arg Glu Leu Thr Ile Ser Val Leu
225                 230                 235                 240

Asp Ile Ile Ser Phe Phe Arg Asn Tyr Asp Ser Arg Leu Tyr Pro Ile
                245                 250                 255

Pro Thr Ser Ser Gln Leu Thr Arg Glu Val Tyr Thr Asp Pro Val Ile
            260                 265                 270

Asn Ile Thr Asp Tyr Arg Val Gly Pro Ser Phe Glu Asn Ile Glu Asn
        275                 280                 285

Ser Ala Ile Arg Ser Pro His Leu Met Asp Phe Leu Asn Asn Leu Thr
    290                 295                 300

Ile Asp Thr Asp Leu Ile Arg Gly Val His Tyr Trp Ala Gly His Arg
305                 310                 315                 320

Val Thr Ser His Phe Thr Gly Ser Ser Gln Val Ile Thr Thr Pro Gln
                325                 330                 335

Tyr Gly Ile Thr Ala Asn Ala Glu Pro Arg Arg Thr Ile Ala Pro Ser
            340                 345                 350

Thr Phe Pro Gly Leu Asn Leu Phe Tyr Arg Thr Leu Ser Asn Pro Phe
        355                 360                 365

Phe Arg Arg Ser Glu Asn Ile Thr Pro Thr Leu Gly Ile Asn Val Val
    370                 375                 380

Gln Gly Val Gly Phe Ile Gln Pro Asn Asn Ala Glu Val Leu Tyr Arg
385                 390                 395                 400

Ser Arg Gly Thr Val Asp Ser Leu Asn Glu Leu Pro Ile Asp Gly Glu
                405                 410                 415

Asn Ser Leu Val Gly Tyr Ser His Arg Leu Ser His Val Thr Leu Thr
            420                 425                 430

Arg Ser Leu Tyr Asn Thr Asn Ile Thr Ser Leu Pro Thr Phe Val Trp
        435                 440                 445

Thr His His Ser Ala Thr Asn Thr Asn Thr Ile Asn Pro Asp Ile Ile
    450                 455                 460

Thr Gln Ile Pro Leu Val Lys Gly Phe Arg Leu Gly Gly Gly Thr Ser
465                 470                 475                 480

Val Ile Lys Gly Pro Gly Phe Thr Gly Gly Asp Ile Leu Arg Arg Asn
                485                 490                 495

Thr Ile Gly Glu Phe Val Ser Leu Gln Val Asn Ile Asn Ser Pro Ile
            500                 505                 510

Thr Gln Arg Tyr Arg Leu Arg Phe Arg Tyr Ala Ser Ser Arg Asp Ala
        515                 520                 525

Arg Ile Thr Val Ala Ile Gly Gly Gln Ile Arg Val Asp Met Thr Leu
    530                 535                 540

Glu Lys Thr Met Glu Ile Gly Glu Ser Leu Thr Ser Arg Thr Phe Ser
545                 550                 555                 560

Tyr Thr Asn Phe Ser Asn Pro Phe Ser Phe Arg Ala Asn Pro Asp Ile
                565                 570                 575

Ile Arg Ile Ala Glu Glu Leu Pro Ile Arg Gly Gly Glu Leu Tyr Ile
            580                 585                 590

Asp Lys Ile Glu Leu Ile Leu Ala Asp Ala Thr Phe Glu Glu Glu Tyr
        595                 600                 605

Asp Leu Glu Arg Ala Gln Lys Ala Val Asn Ala Leu Phe Thr Ser Thr
    610                 615                 620
```

-continued

```
Asn Gln Leu Gly Leu Lys Thr Asp Val Thr Asp Tyr His Ile Asp Gln
625                 630                 635                 640

Val Ser Asn Leu Val Glu Cys Leu Ser Asp Glu Phe Cys Leu Asp Glu
            645                 650                 655

Lys Arg Glu Leu Ser Glu Lys Val Lys His Ala Lys Arg Leu Ser Asp
        660                 665                 670

Glu Arg Asn Leu Leu Gln Asp Pro Asn Phe Arg Gly Ile Asn Arg Gln
    675                 680                 685

Pro Asp Arg Gly Trp Arg Gly Ser Thr Asp Ile Thr Ile Gln Gly Gly
690                 695                 700

Asp Asp Val Phe Lys Glu Asn Tyr Val Thr Leu Pro Gly Thr Phe Asp
705                 710                 715                 720

Glu Cys Tyr Pro Thr Tyr Leu Tyr Gln Lys Ile Asp Glu Ser Lys Leu
            725                 730                 735

Lys Ala Tyr Thr Arg Tyr Glu Leu Arg Gly Tyr Ile Glu Asp Ser Gln
        740                 745                 750

Asp Leu Glu Ile Tyr Leu Ile Arg Tyr Asn Ala Lys His Glu Thr Val
    755                 760                 765

Asn Val Pro Gly Thr Gly Ser Leu Trp Pro Leu Ser Ala Gln Ser Pro
770                 775                 780

Ile Gly Lys Cys Gly Glu Pro Asn Arg Cys Ala Pro His Leu Glu Trp
785                 790                 795                 800

Asn Pro Asn Leu Asp Cys Ser Cys Arg Asp Gly Glu Lys Cys Ala His
            805                 810                 815

His Ser His His Phe Ser Leu Asp Ile Asp Val Gly Cys Thr Asp Leu
        820                 825                 830

Asn Glu Asp Leu Gly Val Trp Val Ile Phe Lys Ile Lys Thr Gln Asp
    835                 840                 845

Gly Tyr Ala Arg Leu Gly Asn Leu Glu Phe Leu Glu Glu Asn Pro Leu
850                 855                 860

Leu Gly Glu Ala Leu Ala Arg Val Lys Arg Ala Glu Lys Lys Trp Arg
865                 870                 875                 880

Asp Lys Cys Glu Lys Leu Glu Trp Glu Thr Asn Ile Val Tyr Lys Glu
            885                 890                 895

Ala Lys Glu Ser Val Asp Ala Leu Phe Val Asn Ser Gln Tyr Asp Arg
        900                 905                 910

Leu Gln Ala Asp Thr Asn Ile Ala Met Ile His Ala Ala Asp Lys Arg
    915                 920                 925

Val His Ser Ile Arg Glu Ala Tyr Leu Pro Glu Leu Ser Val Ile Pro
930                 935                 940

Gly Val Asn Ala Ala Ile Phe Glu Glu Leu Glu Gly Arg Ile Phe Thr
945                 950                 955                 960

Ala Phe Ser Leu Tyr Asp Ala Arg Asn Val Ile Lys Asn Gly Asp Phe
            965                 970                 975

Asn Asn Gly Leu Ser Cys Trp Asn Val Lys Gly His Val Asp Val Glu
        980                 985                 990

Glu Gln Asn Asn His Arg Ser Val Leu Val Pro Glu Trp Glu Ala
    995                 1000                1005

Glu Val Ser Gln Glu Val Arg Val Cys Pro Gly Arg Gly Tyr Ile Leu
    1010                1015                1020

Arg Val Thr Ala Tyr Lys Glu Gly Tyr Gly Glu Gly Cys Val Thr Ile
1025                1030                1035                1040

His Glu Ile Glu Asp Asn Thr Asp Glu Leu Lys Phe Ser Asn Cys Val
```

```
                  1045                1050                1055
Glu Glu Glu Val Tyr Pro Asn Asn Thr Val Thr Cys Asn Asn Tyr Thr
            1060                1065                1070

Ala Thr Gln Glu Glu His Glu Gly Thr Tyr Thr Ser Arg Asn Arg Gly
            1075                1080                1085

Tyr Asp Glu Ala Tyr Glu Ser Asn Ser Ser Val His Ala Ser Val Tyr
            1090                1095                1100

Glu Glu Lys Ser Tyr Thr Asp Arg Arg Glu Asn Pro Cys Glu Ser
1105                1110                1115                1120

Asn Arg Gly Tyr Gly Asp Tyr Thr Pro Leu Pro Ala Gly Tyr Val Thr
            1125                1130                1135

Lys Glu Leu Glu Tyr Phe Pro Glu Thr Asp Lys Val Trp Ile Glu Ile
            1140                1145                1150

Gly Glu Thr Glu Gly Thr Phe Ile Val Asp Ser Val Glu Leu Leu Leu
            1155                1160                1165

Met Glu Glu
    1170

(2) INFORMATION FOR SEQ ID NO: 5:

(i) SEQUENCE CHARACTERISTICS:
        (A) LENGTH: 3558 base pairs
        (B) TYPE: nucleic acid
        (C) STRANDEDNESS: single
        (D) TOPOLOGY: unknown (ii) MOLECULE TYPE: cDNA (iii) HYPOTHETICAL: NO (iv) ANTI-SENSE: NO (vi) ORIGINAL SOURCE:
        (A) ORGANISM: Hybrid sequence (ix) FEATURE:
        (A) NAME/KEY: CDS
        (B) LOCATION: 1..3558

(xi) SEQUENCE DESCRIPTION: SEQ ID NO: 5:

ATG GAG ATA GTG AAT AAT CAG AAT CAA TGC GTG CCT TAT AAT TGT TTA      48
Met Glu Ile Val Asn Asn Gln Asn Gln Cys Val Pro Tyr Asn Cys Leu
 1               5                  10                  15

AAT AAT CCT GAA AAT GAG ATA TTA GAT ATT GAA AGG TCA AAT AGT ACT      96
Asn Asn Pro Glu Asn Glu Ile Leu Asp Ile Glu Arg Ser Asn Ser Thr
                20                  25                  30

GTA GCA ACA AAC ATC GCC TTG GAG ATT AGT CGT CTG CTC GCT TCC GCA     144
Val Ala Thr Asn Ile Ala Leu Glu Ile Ser Arg Leu Leu Ala Ser Ala
         35                  40                  45

ACT CCA ATA GGG GGG ATT TTA TTA GGA TTG TTT GAT GCA ATA TGG GGG     192
Thr Pro Ile Gly Gly Ile Leu Leu Gly Leu Phe Asp Ala Ile Trp Gly
     50                  55                  60

TCT ATA GGC CCT TCA CAA TGG GAT TTA TTT TTA GAG CAA ATT GAG CTA     240
Ser Ile Gly Pro Ser Gln Trp Asp Leu Phe Leu Glu Gln Ile Glu Leu
 65                  70                  75                  80

TTG ATT GAC CAA AAA ATA GAG GAA TTC GCT AGA AAC CAG GCA ATT TCT     288
Leu Ile Asp Gln Lys Ile Glu Glu Phe Ala Arg Asn Gln Ala Ile Ser
                85                  90                  95

AGA TTG GAA GGG ATA AGC AGT CTG TAC GGA ATT TAT ACA GAA GCT TTT     336
Arg Leu Glu Gly Ile Ser Ser Leu Tyr Gly Ile Tyr Thr Glu Ala Phe
                100                 105                 110

AGA GAG TGG GAA GCA GAT CCT ACT AAT CCA GCA TTA AAA GAA GAG ATG     384
```

```
Arg Glu Trp Glu Ala Asp Pro Thr Asn Pro Ala Leu Lys Glu Glu Met
        115                 120                 125

CGT ACT CAA TTT AAT GAC ATG AAC AGT ATT CTT GTA ACA GCT ATT CCT      432
Arg Thr Gln Phe Asn Asp Met Asn Ser Ile Leu Val Thr Ala Ile Pro
        130                 135                 140

CTT TTT TCA GTT CAA AAT TAT CAA GTC CCA TTT TTA TCA GTA TAT GTT      480
Leu Phe Ser Val Gln Asn Tyr Gln Val Pro Phe Leu Ser Val Tyr Val
145                 150                 155                 160

CAA GCT GCA AAT TTA CAT TTA TCG GTT TTG AGA GAT GTT TCA GTG TTT      528
Gln Ala Ala Asn Leu His Leu Ser Val Leu Arg Asp Val Ser Val Phe
                165                 170                 175

GGG CAG GCT TGG GGA TTT GAT ATA GCA ACA ATA AAT AGT CGT TAT AAT      576
Gly Gln Ala Trp Gly Phe Asp Ile Ala Thr Ile Asn Ser Arg Tyr Asn
                180                 185                 190

GAT CTG ACT AGA CTT ATT CCT ATA TAT ACA GAT TAT GCT GTA CGC TGG      624
Asp Leu Thr Arg Leu Ile Pro Ile Tyr Thr Asp Tyr Ala Val Arg Trp
            195                 200                 205

TAC AAT ACG GGA TTA GAT CGC TTA CCA CGA ACT GGT GGG CTG CGA AAC      672
Tyr Asn Thr Gly Leu Asp Arg Leu Pro Arg Thr Gly Gly Leu Arg Asn
        210                 215                 220

TGG GCA AGA TTT AAT CAG TTT AGA AGA GAG TTA ACA ATA TCA GTA TTA      720
Trp Ala Arg Phe Asn Gln Phe Arg Arg Glu Leu Thr Ile Ser Val Leu
225                 230                 235                 240

GAT ATT ATT TCT TTT TTC AGA AAT TAC GAT TCT AGA TTA TAT CCA ATT      768
Asp Ile Ile Ser Phe Phe Arg Asn Tyr Asp Ser Arg Leu Tyr Pro Ile
                245                 250                 255

CCA ACA AGC TCC CAA TTA ACG CGG GAA GTA TAT ACA GAT CCG GTA ATT      816
Pro Thr Ser Ser Gln Leu Thr Arg Glu Val Tyr Thr Asp Pro Val Ile
                260                 265                 270

AAT ATA ACT GAC TAT AGA GTT GGC CCC AGC TTC GAG AAT ATT GAG AAC      864
Asn Ile Thr Asp Tyr Arg Val Gly Pro Ser Phe Glu Asn Ile Glu Asn
            275                 280                 285

TCA GCC ATT AGA AGC CCC CAC CTT ATG GAC TTC TTA AAT AAT TTG ACC      912
Ser Ala Ile Arg Ser Pro His Leu Met Asp Phe Leu Asn Asn Leu Thr
        290                 295                 300

ATT GAT ACG GAT TTG ATT AGA GGT GTT CAC TAT TGG GCA GGG CAT CGT      960
Ile Asp Thr Asp Leu Ile Arg Gly Val His Tyr Trp Ala Gly His Arg
305                 310                 315                 320

GTA ACT TCT CAT TTT ACA GGT AGT TCT CAA GTG ATA ACA ACC CCT CAA     1008
Val Thr Ser His Phe Thr Gly Ser Ser Gln Val Ile Thr Thr Pro Gln
                325                 330                 335

TAT GGG ATA ACC GCA AAT GCG GAA CCA AGA CGA ACT ATT GCT CCT AGT     1056
Tyr Gly Ile Thr Ala Asn Ala Glu Pro Arg Arg Thr Ile Ala Pro Ser
                340                 345                 350

ACT TTT CCA GGT CTT AAC CTA TTT TAT AGA ACA TTA TCA AAT CCT TTC     1104
Thr Phe Pro Gly Leu Asn Leu Phe Tyr Arg Thr Leu Ser Asn Pro Phe
            355                 360                 365

TTC CGA AGA TCA GAA AAT ATT ACT CCT ACC TTA GGG ATA AAT GTA GTA     1152
Phe Arg Arg Ser Glu Asn Ile Thr Pro Thr Leu Gly Ile Asn Val Val
        370                 375                 380

CAG GGA GTA GGG TTC ATT CAA CCA AAT AAT GCT GAA GTT CTA TAT AGA     1200
Gln Gly Val Gly Phe Ile Gln Pro Asn Asn Ala Glu Val Leu Tyr Arg
385                 390                 395                 400

AGT AGG GGG ACA GTA GAT TCT CTT AAT GAG TTA CCA ATT GAT GGT GAG     1248
Ser Arg Gly Thr Val Asp Ser Leu Asn Glu Leu Pro Ile Asp Gly Glu
                405                 410                 415

AAT TCA TTA GTT GGA TAT AGT CAT CGA TTA AGT CAT GTT ACA CTA ACC     1296
Asn Ser Leu Val Gly Tyr Ser His Arg Leu Ser His Val Thr Leu Thr
                420                 425                 430
```

```
AGG TCG TTA TAT AAT ACT AAT ATA ACT AGC CTG CCA ACA TTT GTT TGG       1344
Arg Ser Leu Tyr Asn Thr Asn Ile Thr Ser Leu Pro Thr Phe Val Trp
            435                 440                 445

ACA CAT CAC AGT GCT ACT AAT ACA AAT ACA ATT AAT CCA GAT ATT ATT       1392
Thr His His Ser Ala Thr Asn Thr Asn Thr Ile Asn Pro Asp Ile Ile
450                 455                 460

ACA CAA ATA CCT TTA GTG AAA GGA TTT AGA GTT TGG GGG GGC ACC TCT       1440
Thr Gln Ile Pro Leu Val Lys Gly Phe Arg Val Trp Gly Gly Thr Ser
465                 470                 475                 480

GTC ATT ACA GGA CCA GGA TTT ACA GGG GAT ATC CTT CGA AGA AAT           1488
Val Ile Thr Gly Pro Gly Phe Thr Gly Gly Asp Ile Leu Arg Arg Asn
                485                 490                 495

ACC TTT GGT GAT TTT GTA TCT CTA CAA GTC AAT ATT AAT TCA CCA ATT       1536
Thr Phe Gly Asp Phe Val Ser Leu Gln Val Asn Ile Asn Ser Pro Ile
                500                 505                 510

ACC CAA AGA TAC CGT TTA AGA TTT CGT TAC GCT TCC AGT AGG GAT GCA       1584
Thr Gln Arg Tyr Arg Leu Arg Phe Arg Tyr Ala Ser Ser Arg Asp Ala
                515                 520                 525

CGA GTT ATA GTA TTA ACA GGA GCG GCA TCC ACA GGA GTG GGA GGC CAA       1632
Arg Val Ile Val Leu Thr Gly Ala Ala Ser Thr Gly Val Gly Gly Gln
530                 535                 540

GTT AGT GTA AAT ATG CCT CTT CAG AAA ACT ATG GAA ATA GGG GAG AAC       1680
Val Ser Val Asn Met Pro Leu Gln Lys Thr Met Glu Ile Gly Glu Asn
545                 550                 555                 560

TTA ACA TCT AGA ACA TTT AGA TAT ACC GAT TTT AGT AAT CCT TTT TCA       1728
Leu Thr Ser Arg Thr Phe Arg Tyr Thr Asp Phe Ser Asn Pro Phe Ser
                565                 570                 575

TTT AGA GCT AAT CCA GAT ATA ATT GGG ATA AGT GAA CAA CCT CTA TTT       1776
Phe Arg Ala Asn Pro Asp Ile Ile Gly Ile Ser Glu Gln Pro Leu Phe
                580                 585                 590

GGT GCA GGT TCT ATT AGT AGC GGT GAA CTT TAT ATA GAT AAA ATT GAA       1824
Gly Ala Gly Ser Ile Ser Ser Gly Glu Leu Tyr Ile Asp Lys Ile Glu
                595                 600                 605

ATT ATT CTA GCA GAT GCA ACA TTT GAA GCA GAA TCT GAT TTA GAA AGA       1872
Ile Ile Leu Ala Asp Ala Thr Phe Glu Ala Glu Ser Asp Leu Glu Arg
610                 615                 620

GCA CAA AAG GCG GTG AAT GCC CTG TTT ACT TCT TCC AAT CAA ATC GGG       1920
Ala Gln Lys Ala Val Asn Ala Leu Phe Thr Ser Ser Asn Gln Ile Gly
625                 630                 635                 640

TTA AAA ACC GAT GTG ACG GAT TAT CAT ATT GAT CAA GTA TCC AAT TTA       1968
Leu Lys Thr Asp Val Thr Asp Tyr His Ile Asp Gln Val Ser Asn Leu
                645                 650                 655

GTG GAT TGT TTA TCA GAT GAA TTT TGT CTG GAT GAA AAG CGA GAA TTG       2016
Val Asp Cys Leu Ser Asp Glu Phe Cys Leu Asp Glu Lys Arg Glu Leu
                660                 665                 670

TCC GAG AAA GTC AAA CAT GCG AAG CGA CTC AGT GAT GAG CGG AAT TTA       2064
Ser Glu Lys Val Lys His Ala Lys Arg Leu Ser Asp Glu Arg Asn Leu
                675                 680                 685

CTT CAA GAT CCA AAC TTC AGA GGG ATC AAT AGA CAA CCA GAC CGT GGC       2112
Leu Gln Asp Pro Asn Phe Arg Gly Ile Asn Arg Gln Pro Asp Arg Gly
690                 695                 700

TGG AGA GGA AGT ACA GAT ATT ACC ATC CAA GGA GGA GAT GAC GTA TTC       2160
Trp Arg Gly Ser Thr Asp Ile Thr Ile Gln Gly Gly Asp Asp Val Phe
705                 710                 715                 720

AAA GAG AAT TAC GTC ACA CTA CCG GGT ACC GTT GAT GAG TGC TAT CCA       2208
Lys Glu Asn Tyr Val Thr Leu Pro Gly Thr Val Asp Glu Cys Tyr Pro
                725                 730                 735

ACG TAT TTA TAT CAG AAA ATA GAT GAG TCG AAA TTA AAA GCT TAT ACC       2256
Thr Tyr Leu Tyr Gln Lys Ile Asp Glu Ser Lys Leu Lys Ala Tyr Thr
                740                 745                 750
```

```
CGT TAT GAA TTA AGA GGG TAT ATC GAA GAT AGT CAA GAC TTA GAA ATC        2304
Arg Tyr Glu Leu Arg Gly Tyr Ile Glu Asp Ser Gln Asp Leu Glu Ile
        755                 760                 765

TAT TTG ATC CGT TAC AAT GCA AAA CAC GAA ATA GTA AAT GTG CCA GGC        2352
Tyr Leu Ile Arg Tyr Asn Ala Lys His Glu Ile Val Asn Val Pro Gly
    770                 775                 780

ACG GGT TCC TTA TGG CCG CTT TCA GCC CAA AGT CCA ATC GGA AAG TGT        2400
Thr Gly Ser Leu Trp Pro Leu Ser Ala Gln Ser Pro Ile Gly Lys Cys
785                 790                 795                 800

GGA GAA CCG AAT CGA TGC GCG CCA CAC CTT GAA TGG AAT CCT GAT CTA        2448
Gly Glu Pro Asn Arg Cys Ala Pro His Leu Glu Trp Asn Pro Asp Leu
            805                 810                 815

GAT TGT TCC TGC AGA GAC GGG GAA AAA TGT GCA CAT CAT TCC CAT CAT        2496
Asp Cys Ser Cys Arg Asp Gly Glu Lys Cys Ala His His Ser His His
                820                 825                 830

TTC ACC TTG GAT ATT GAT GTT GGA TGT ACA GAC TTA AAT GAG GAC TTA        2544
Phe Thr Leu Asp Ile Asp Val Gly Cys Thr Asp Leu Asn Glu Asp Leu
            835                 840                 845

GGT GTA TGG GTG ATA TTC AAG ATT AAG ACG CAA GAT GGC CAT GCA AGA        2592
Gly Val Trp Val Ile Phe Lys Ile Lys Thr Gln Asp Gly His Ala Arg
850                 855                 860

CTA GGG AAT CTA GAG TTT CTC GAA GAG AAA CCA TTA TTA GGG GAA GCA        2640
Leu Gly Asn Leu Glu Phe Leu Glu Glu Lys Pro Leu Leu Gly Glu Ala
865                 870                 875                 880

CTA GCT CGT GTG AAA AGA GCG GAG AAG AAG TGG AGA GAC AAA CGA GAG        2688
Leu Ala Arg Val Lys Arg Ala Glu Lys Lys Trp Arg Asp Lys Arg Glu
            885                 890                 895

AAA CTG CAG TTG GAA ACA AAT ATT GTT TAT AAA GAG GCA AAA GAA TCT        2736
Lys Leu Gln Leu Glu Thr Asn Ile Val Tyr Lys Glu Ala Lys Glu Ser
                900                 905                 910

GTA GAT GCT TTA TTT GTA AAC TCT CAA TAT GAT AGA TTA CAA GTG GAT        2784
Val Asp Ala Leu Phe Val Asn Ser Gln Tyr Asp Arg Leu Gln Val Asp
            915                 920                 925

ACG AAC ATC GCG ATG ATT CAT GCG GCA GAT AAA CGC GTT CAT AGA ATC        2832
Thr Asn Ile Ala Met Ile His Ala Ala Asp Lys Arg Val His Arg Ile
930                 935                 940

CGG GAA GCG TAT CTG CCA GAG TTG TCT GTG ATT CCA GGT GTC AAT GCG        2880
Arg Glu Ala Tyr Leu Pro Glu Leu Ser Val Ile Pro Gly Val Asn Ala
945                 950                 955                 960

GCC ATT TTC GAA GAA TTA GAG GGA CGT ATT TTT ACA GCG TAT TCC TTA        2928
Ala Ile Phe Glu Glu Leu Glu Gly Arg Ile Phe Thr Ala Tyr Ser Leu
            965                 970                 975

TAT GAT GCG AGA AAT GTC ATT AAA AAT GGC GAT TTC AAT AAT GGC TTA        2976
Tyr Asp Ala Arg Asn Val Ile Lys Asn Gly Asp Phe Asn Asn Gly Leu
                980                 985                 990

TTA TGC TGG AAC GTG AAA GGT CAT GTA GAT GTA GAA GAG CAA AAC AAC        3024
Leu Cys Trp Asn Val Lys Gly His Val Asp Val Glu Glu Gln Asn Asn
            995                 1000                1005

CAC CGT TCG GTC CTT GTT ATC CCA GAA TGG GAG GCA GAA GTG TCA CAA        3072
His Arg Ser Val Leu Val Ile Pro Glu Trp Glu Ala Glu Val Ser Gln
    1010                1015                1020

GAG GTT CGT GTC TGT CCA GGT CGT GGC TAT ATC CTT CGT GTC ACA GCA        3120
Glu Val Arg Val Cys Pro Gly Arg Gly Tyr Ile Leu Arg Val Thr Ala
1025                1030                1035                1040

TAT AAA GAG GGA TAT GGA GAG GGC TGC GTA ACG ATC CAT GAG ATC GAA        3168
Tyr Lys Glu Gly Tyr Gly Glu Gly Cys Val Thr Ile His Glu Ile Glu
            1045                1050                1055

GAC AAT ACA GAC GAA CTG AAA TTC AGC AAC TGT GTA GAA GAG GAA GTA        3216
Asp Asn Thr Asp Glu Leu Lys Phe Ser Asn Cys Val Glu Glu Glu Val
```

```
                1060              1065              1070
TAT CCA AAC AAC ACA GTA ACG TGT AAT AAT TAT ACT GGG ACT CAA GAA     3264
Tyr Pro Asn Asn Thr Val Thr Cys Asn Asn Tyr Thr Gly Thr Gln Glu
        1075                1080                1085

GAA TAT GAG GGT ACG TAC ACT TCT CGT AAT CAA GGA TAT GAC GAA GCC     3312
Glu Tyr Glu Gly Thr Tyr Thr Ser Arg Asn Gln Gly Tyr Asp Glu Ala
        1090                1095                1100

TAT GGT AAT AAC CCT TCC GTA CCA GCT GAT TAC GCT TCA GTC TAT GAA     3360
Tyr Gly Asn Asn Pro Ser Val Pro Ala Asp Tyr Ala Ser Val Tyr Glu
1105                1110                1115                1120

GAA AAA TCG TAT ACA GAT GGA CGA AGA GAG AAT CCT TGT GAA TCT AAC     3408
Glu Lys Ser Tyr Thr Asp Gly Arg Arg Glu Asn Pro Cys Glu Ser Asn
                1125                1130                1135

AGA GGC TAT GGG GAT TAC ACA CCA CTA CCG GCT GGT TAT GTA ACA AAG     3456
Arg Gly Tyr Gly Asp Tyr Thr Pro Leu Pro Ala Gly Tyr Val Thr Lys
                1140                1145                1150

GAT TTA GAG TAC TTC CCA GAG ACC GAT AAG GTA TGG ATT GAG ATC GGA     3504
Asp Leu Glu Tyr Phe Pro Glu Thr Asp Lys Val Trp Ile Glu Ile Gly
        1155                1160                1165

GAA ACA GAA GGA ACA TTC ATC GTG GAT AGC GTG GAA TTA CTC CTT ATG     3552
Glu Thr Glu Gly Thr Phe Ile Val Asp Ser Val Glu Leu Leu Leu Met
        1170                1175                1180

GAG GAA                                                             3558
Glu Glu
1185

(2) INFORMATION FOR SEQ ID NO: 6:

(i) SEQUENCE CHARACTERISTICS:
        (A) LENGTH: 1186 amino acids
        (B) TYPE: amino acid
        (D) TOPOLOGY: linear (ii) MOLECULE TYPE: protein (xi) SEQUENCE DESCRIPTION: SEQ ID NO: 6:

Met Glu Ile Val Asn Asn Gln Asn Gln Cys Val Pro Tyr Asn Cys Leu
 1               5                  10                  15

Asn Asn Pro Glu Asn Glu Ile Leu Asp Ile Glu Arg Ser Asn Ser Thr
            20                  25                  30

Val Ala Thr Asn Ile Ala Leu Glu Ile Ser Arg Leu Leu Ala Ser Ala
        35                  40                  45

Thr Pro Ile Gly Gly Ile Leu Gly Leu Phe Asp Ala Ile Trp Gly
    50                  55                  60

Ser Ile Gly Pro Ser Gln Trp Asp Leu Phe Leu Glu Gln Ile Glu Leu
65                  70                  75                  80

Leu Ile Asp Gln Lys Ile Glu Glu Phe Ala Arg Asn Gln Ala Ile Ser
                85                  90                  95

Arg Leu Glu Gly Ile Ser Ser Leu Tyr Gly Ile Tyr Thr Glu Ala Phe
            100                 105                 110

Arg Glu Trp Glu Ala Asp Pro Thr Asn Pro Ala Leu Lys Glu Glu Met
        115                 120                 125

Arg Thr Gln Phe Asn Asp Met Asn Ser Ile Leu Val Thr Ala Ile Pro
    130                 135                 140

Leu Phe Ser Val Gln Asn Tyr Gln Val Pro Phe Leu Ser Val Tyr Val
145                 150                 155                 160

Gln Ala Ala Asn Leu His Leu Ser Val Leu Arg Asp Val Ser Val Phe
                165                 170                 175
```

```
Gly Gln Ala Trp Gly Phe Asp Ile Ala Thr Ile Asn Ser Arg Tyr Asn
            180                 185                 190

Asp Leu Thr Arg Leu Ile Pro Ile Tyr Thr Asp Tyr Ala Val Arg Trp
            195                 200                 205

Tyr Asn Thr Gly Leu Asp Arg Leu Pro Arg Thr Gly Leu Arg Asn
            210                 215                 220

Trp Ala Arg Phe Asn Gln Phe Arg Arg Glu Leu Thr Ile Ser Val Leu
225                 230                 235                 240

Asp Ile Ile Ser Phe Phe Arg Asn Tyr Asp Ser Arg Leu Tyr Pro Ile
                245                 250                 255

Pro Thr Ser Ser Gln Leu Thr Arg Glu Val Tyr Thr Asp Pro Val Ile
            260                 265                 270

Asn Ile Thr Asp Tyr Arg Val Gly Pro Ser Phe Glu Asn Ile Glu Asn
            275                 280                 285

Ser Ala Ile Arg Ser Pro His Leu Met Asp Phe Leu Asn Asn Leu Thr
            290                 295                 300

Ile Asp Thr Asp Leu Ile Arg Gly Val His Tyr Trp Ala Gly His Arg
305                 310                 315                 320

Val Thr Ser His Phe Thr Gly Ser Ser Gln Val Ile Thr Thr Pro Gln
                325                 330                 335

Tyr Gly Ile Thr Ala Asn Ala Glu Pro Arg Arg Thr Ile Ala Pro Ser
            340                 345                 350

Thr Phe Pro Gly Leu Asn Leu Phe Tyr Arg Thr Leu Ser Asn Pro Phe
            355                 360                 365

Phe Arg Arg Ser Glu Asn Ile Thr Pro Thr Leu Gly Ile Asn Val Val
            370                 375                 380

Gln Gly Val Gly Phe Ile Gln Pro Asn Asn Ala Glu Val Leu Tyr Arg
385                 390                 395                 400

Ser Arg Gly Thr Val Asp Ser Leu Asn Glu Leu Pro Ile Asp Gly Glu
                405                 410                 415

Asn Ser Leu Val Gly Tyr Ser His Arg Leu Ser His Val Thr Leu Thr
            420                 425                 430

Arg Ser Leu Tyr Asn Thr Asn Ile Thr Ser Leu Pro Thr Phe Val Trp
            435                 440                 445

Thr His His Ser Ala Thr Asn Thr Asn Thr Ile Asn Pro Asp Ile Ile
            450                 455                 460

Thr Gln Ile Pro Leu Val Lys Gly Phe Arg Val Trp Gly Gly Thr Ser
465                 470                 475                 480

Val Ile Thr Gly Pro Gly Phe Thr Gly Gly Asp Ile Leu Arg Arg Asn
                485                 490                 495

Thr Phe Gly Asp Phe Val Ser Leu Gln Val Asn Ile Asn Ser Pro Ile
            500                 505                 510

Thr Gln Arg Tyr Arg Leu Arg Phe Arg Tyr Ala Ser Ser Arg Asp Ala
            515                 520                 525

Arg Val Ile Val Leu Thr Gly Ala Ala Ser Thr Gly Val Gly Gly Gln
            530                 535                 540

Val Ser Val Asn Met Pro Leu Gln Lys Thr Met Glu Ile Gly Glu Asn
545                 550                 555                 560

Leu Thr Ser Arg Thr Phe Arg Tyr Thr Asp Phe Ser Asn Pro Phe Ser
                565                 570                 575

Phe Arg Ala Asn Pro Asp Ile Ile Gly Ile Ser Glu Gln Pro Leu Phe
            580                 585                 590

Gly Ala Gly Ser Ile Ser Ser Gly Glu Leu Tyr Ile Asp Lys Ile Glu
```

-continued

```
                595                 600                 605
Ile Ile Leu Ala Asp Ala Thr Phe Glu Ala Glu Ser Asp Leu Glu Arg
610                     615                 620

Ala Gln Lys Ala Val Asn Ala Leu Phe Thr Ser Ser Asn Gln Ile Gly
625                 630                 635                 640

Leu Lys Thr Asp Val Thr Asp Tyr His Ile Asp Gln Val Ser Asn Leu
                    645                 650                 655

Val Asp Cys Leu Ser Asp Glu Phe Cys Leu Asp Glu Lys Arg Glu Leu
                660                 665                 670

Ser Glu Lys Val Lys His Ala Lys Arg Leu Ser Asp Glu Arg Asn Leu
            675                 680                 685

Leu Gln Asp Pro Asn Phe Arg Gly Ile Asn Arg Gln Pro Asp Arg Gly
690                 695                 700

Trp Arg Gly Ser Thr Asp Ile Thr Ile Gln Gly Gly Asp Asp Val Phe
705                 710                 715                 720

Lys Glu Asn Tyr Val Thr Leu Pro Gly Thr Val Asp Glu Cys Tyr Pro
                725                 730                 735

Thr Tyr Leu Tyr Gln Lys Ile Asp Glu Ser Lys Leu Lys Ala Tyr Thr
                740                 745                 750

Arg Tyr Glu Leu Arg Gly Tyr Ile Glu Asp Ser Gln Asp Leu Glu Ile
                755                 760                 765

Tyr Leu Ile Arg Tyr Asn Ala Lys His Glu Ile Val Asn Val Pro Gly
770                 775                 780

Thr Gly Ser Leu Trp Pro Leu Ser Ala Gln Ser Pro Ile Gly Lys Cys
785                 790                 795                 800

Gly Glu Pro Asn Arg Cys Ala Pro His Leu Glu Trp Asn Pro Asp Leu
                805                 810                 815

Asp Cys Ser Cys Arg Asp Gly Glu Lys Cys Ala His His Ser His His
                820                 825                 830

Phe Thr Leu Asp Ile Asp Val Gly Cys Thr Asp Leu Asn Glu Asp Leu
                835                 840                 845

Gly Val Trp Val Ile Phe Lys Ile Lys Thr Gln Asp Gly His Ala Arg
850                 855                 860

Leu Gly Asn Leu Glu Phe Leu Glu Glu Lys Pro Leu Leu Gly Glu Ala
865                 870                 875                 880

Leu Ala Arg Val Lys Arg Ala Glu Lys Lys Trp Arg Asp Lys Arg Glu
                885                 890                 895

Lys Leu Gln Leu Glu Thr Asn Ile Val Tyr Lys Glu Ala Lys Glu Ser
                900                 905                 910

Val Asp Ala Leu Phe Val Asn Ser Gln Tyr Asp Arg Leu Gln Val Asp
                915                 920                 925

Thr Asn Ile Ala Met Ile His Ala Ala Asp Lys Arg Val His Arg Ile
930                 935                 940

Arg Glu Ala Tyr Leu Pro Glu Leu Ser Val Ile Pro Gly Val Asn Ala
945                 950                 955                 960

Ala Ile Phe Glu Glu Leu Glu Gly Arg Ile Phe Thr Ala Tyr Ser Leu
                965                 970                 975

Tyr Asp Ala Arg Asn Val Ile Lys Asn Gly Asp Phe Asn Asn Gly Leu
                980                 985                 990

Leu Cys Trp Asn Val Lys Gly His Val Asp Val Glu Glu Gln Asn Asn
                995                 1000                1005

His Arg Ser Val Leu Val Ile Pro Glu Trp Glu Ala Glu Val Ser Gln
1010                1015                1020
```

```
Glu Val Arg Val Cys Pro Gly Arg Gly Tyr Ile Leu Arg Val Thr Ala
1025                1030                1035                1040

Tyr Lys Glu Gly Tyr Gly Gly Cys Val Thr Ile His Glu Ile Glu
                1045                1050                1055

Asp Asn Thr Asp Glu Leu Lys Phe Ser Asn Cys Val Glu Glu Val
            1060                1065                1070

Tyr Pro Asn Asn Thr Val Thr Cys Asn Asn Tyr Thr Gly Thr Gln Glu
        1075                1080                1085

Glu Tyr Glu Gly Thr Tyr Thr Ser Arg Asn Gln Gly Tyr Asp Glu Ala
    1090                1095                1100

Tyr Gly Asn Asn Pro Ser Val Pro Ala Asp Tyr Ala Ser Val Tyr Glu
1105                1110                1115                1120

Glu Lys Ser Tyr Thr Asp Gly Arg Arg Glu Asn Pro Cys Glu Ser Asn
                1125                1130                1135

Arg Gly Tyr Gly Asp Tyr Thr Pro Leu Pro Ala Gly Tyr Val Thr Lys
                1140                1145                1150

Asp Leu Glu Tyr Phe Pro Glu Thr Asp Lys Val Trp Ile Glu Ile Gly
                1155                1160                1165

Glu Thr Glu Gly Thr Phe Ile Val Asp Ser Val Glu Leu Leu Leu Met
    1170                1175                1180

Glu Glu
1185

(2) INFORMATION FOR SEQ ID NO: 7:

(i) SEQUENCE CHARACTERISTICS:
        (A) LENGTH: 3579 base pairs
        (B) TYPE: nucleic acid
        (C) STRANDEDNESS: single
        (D) TOPOLOGY: unknown (ii) MOLECULE TYPE: cDNA (iii) HYPOTHETICAL: NO (iv) ANTI-SENSE: NO (vi) ORIGINAL SOURCE:
        (A) ORGANISM: Hybrid toxin (ix) FEATURE:
        (A) NAME/KEY: CDS
        (B) LOCATION: 1..3579

(xi) SEQUENCE DESCRIPTION: SEQ ID NO: 7:

ATG GAT AAC AAT CCG AAC ATC AAT GAA TGC ATT CCT TAT AAT TGT TTA         48
Met Asp Asn Asn Pro Asn Ile Asn Glu Cys Ile Pro Tyr Asn Cys Leu
1               5                   10                  15

AGT AAC CCT GAA GTA GAA GTA TTA GGT GGA GAA AGA ATA GAA ACT GGT         96
Ser Asn Pro Glu Val Glu Val Leu Gly Gly Glu Arg Ile Glu Thr Gly
            20                  25                  30

TAC ACC CCA ATC GAT ATT TCC TTG TCG CTA ACG CAA TTT CTT TTG AGT        144
Tyr Thr Pro Ile Asp Ile Ser Leu Ser Leu Thr Gln Phe Leu Leu Ser
        35                  40                  45

GAA TTT GTT CCC GGT GCT GGA TTT GTG TTA GGA CTA GTT GAT ATA ATA        192
Glu Phe Val Pro Gly Ala Gly Phe Val Leu Gly Leu Val Asp Ile Ile
    50                  55                  60

TGG GGA ATT TTT GGT CCC TCT CAA TGG GAC GCA TTT CTT GTA CAA ATT        240
Trp Gly Ile Phe Gly Pro Ser Gln Trp Asp Ala Phe Leu Val Gln Ile
65                  70                  75                  80

GAA CAG TTA ATT AAC CAA AGA ATA GAA GAA TTC GCT AGG AAC CAA GCC        288
```

```
                                                                -continued

Glu Gln Leu Ile Asn Gln Arg Ile Glu Glu Phe Ala Arg Asn Gln Ala
            85                  90                  95

ATT TCT AGA TTA GAA GGA CTA AGC AAT CTT TAT CAA ATT TAC GCA GAA        336
Ile Ser Arg Leu Glu Gly Leu Ser Asn Leu Tyr Gln Ile Tyr Ala Glu
            100                 105                 110

TCT TTT AGA GAG TGG GAA GCA GAT CCT ACT AAT CCA GCA TTA AGA GAA        384
Ser Phe Arg Glu Trp Glu Ala Asp Pro Thr Asn Pro Ala Leu Arg Glu
            115                 120                 125

GAG ATG CGT ATT CAA TTC AAT GAC ATG AAC AGT GCC CTT ACA ACC GCT        432
Glu Met Arg Ile Gln Phe Asn Asp Met Asn Ser Ala Leu Thr Thr Ala
    130                 135                 140

ATT CCT CTT TTT GCA GTT CAA AAT TAT CAA GTT CCT CTT TTA TCA GTA        480
Ile Pro Leu Phe Ala Val Gln Asn Tyr Gln Val Pro Leu Leu Ser Val
145                 150                 155                 160

TAT GTT CAA GCT GCA AAT TTA CAT TTA TCA GTT TTG AGA GAT GTT TCA        528
Tyr Val Gln Ala Ala Asn Leu His Leu Ser Val Leu Arg Asp Val Ser
                165                 170                 175

GTG TTT GGA CAA AGG TGG GGA TTT GAT GCC GCG ACT ATC AAT AGT CGT        576
Val Phe Gly Gln Arg Trp Gly Phe Asp Ala Ala Thr Ile Asn Ser Arg
            180                 185                 190

TAT AAT GAT TTA ACT AGG CTT ATT GGC AAC TAT ACA GAT CAT GCT GTA        624
Tyr Asn Asp Leu Thr Arg Leu Ile Gly Asn Tyr Thr Asp His Ala Val
            195                 200                 205

CGC TGG TAC AAT ACG GGA TTA GAG CGT GTA TGG GGA CCG GAT TCT AGA        672
Arg Trp Tyr Asn Thr Gly Leu Glu Arg Val Trp Gly Pro Asp Ser Arg
    210                 215                 220

GAT TGG ATA AGA TAT AAT CAA TTT AGA AGA GAA TTA ACA CTA ACT GTA        720
Asp Trp Ile Arg Tyr Asn Gln Phe Arg Arg Glu Leu Thr Leu Thr Val
225                 230                 235                 240

TTA GAT ATC GTT TCT CTA TTT CCG AAC TAT GAT AGT AGA ACG TAT CCA        768
Leu Asp Ile Val Ser Leu Phe Pro Asn Tyr Asp Ser Arg Thr Tyr Pro
                245                 250                 255

ATT CGA ACA GTT TCC CAA TTA ACA AGA GAA ATT TAT ACA AAC CCA GTA        816
Ile Arg Thr Val Ser Gln Leu Thr Arg Glu Ile Tyr Thr Asn Pro Val
            260                 265                 270

TTA GAA AAT TTT GAT GGT AGT TTT CGA GGC TCG GCT CAG GGC ATA GAA        864
Leu Glu Asn Phe Asp Gly Ser Phe Arg Gly Ser Ala Gln Gly Ile Glu
            275                 280                 285

GGA AGT ATT AGG AGT CCA CAT TTG ATG GAT ATA CTT AAC AGT ATA ACC        912
Gly Ser Ile Arg Ser Pro His Leu Met Asp Ile Leu Asn Ser Ile Thr
    290                 295                 300

ATC TAT ACG GAT GCT CAT AGA GGA GAA TAT TAT TGG TCA GGG CAT CAA        960
Ile Tyr Thr Asp Ala His Arg Gly Glu Tyr Tyr Trp Ser Gly His Gln
305                 310                 315                 320

ATA ATG GCT TCT CCT GTA GGG TTT TCG GGG CCA GAA TTC ACT TTT CCG       1008
Ile Met Ala Ser Pro Val Gly Phe Ser Gly Pro Glu Phe Thr Phe Pro
                325                 330                 335

CTA TAT GGA ACT ATG GGA AAT GCA GCT CCA CAA CAA CGT ATT GTT GCT       1056
Leu Tyr Gly Thr Met Gly Asn Ala Ala Pro Gln Gln Arg Ile Val Ala
            340                 345                 350

CAA CTA GGT CAG GGC GTG TAT AGA ACA TTA TCG TCC ACT TTA TAT AGA       1104
Gln Leu Gly Gln Gly Val Tyr Arg Thr Leu Ser Ser Thr Leu Tyr Arg
            355                 360                 365

AGA CCT TTT AAT ATA GGG ATA AAT AAT CAA CAA CTA TCT GTT CTT GAC       1152
Arg Pro Phe Asn Ile Gly Ile Asn Asn Gln Gln Leu Ser Val Leu Asp
    370                 375                 380

GGG ACA GAA TTT GCT TAT GGA ACC TCC TCA AAT TTG CCA TCC GCT GTA       1200
Gly Thr Glu Phe Ala Tyr Gly Thr Ser Ser Asn Leu Pro Ser Ala Val
385                 390                 395                 400
```

```
                                               -continued

TAC AGA AAA AGC GGA ACG GTA GAT TCG CTG GAT GAA ATA CCG CCA CAG       1248
Tyr Arg Lys Ser Gly Thr Val Asp Ser Leu Asp Glu Ile Pro Pro Gln
                    405                 410                 415

AAT AAC AAC GTG CCA CCT AGG CAA GGA TTT AGT CAT CGA TTA AGC CAT       1296
Asn Asn Asn Val Pro Pro Arg Gln Gly Phe Ser His Arg Leu Ser His
                420                 425                 430

GTT TCA ATG TTT CGT TCA GGC TTT AGT AAT AGT AGT GTA AGT ATA ATA       1344
Val Ser Met Phe Arg Ser Gly Phe Ser Asn Ser Ser Val Ser Ile Ile
            435                 440                 445

AGA GCT CCT ATG TTC TCT TGG ATA CAT CGT AGT GCA ACT CTT ACA AAT       1392
Arg Ala Pro Met Phe Ser Trp Ile His Arg Ser Ala Thr Leu Thr Asn
        450                 455                 460

ACA ATT GAT CCA GAG AGA ATT AAT CAA ATA CCT TTA GTG AAA GGA TTT       1440
Thr Ile Asp Pro Glu Arg Ile Asn Gln Ile Pro Leu Val Lys Gly Phe
465                 470                 475                 480

AGA GTT TGG GGG GGC ACC TCT GTC ATT ACA GGA CCA GGA TTT ACA GGA       1488
Arg Val Trp Gly Gly Thr Ser Val Ile Thr Gly Pro Gly Phe Thr Gly
                    485                 490                 495

GGG GAT ATC CTT CGA AGA AAT ACC TTT GGT GAT TTT GTA TCT CTA CAA       1536
Gly Asp Ile Leu Arg Arg Asn Thr Phe Gly Asp Phe Val Ser Leu Gln
                500                 505                 510

GTC AAT ATT AAT TCA CCA ATT ACC CAA AGA TAC CGT TTA AGA TTT CGT       1584
Val Asn Ile Asn Ser Pro Ile Thr Gln Arg Tyr Arg Leu Arg Phe Arg
            515                 520                 525

TAC GCT TCC AGT AGG GAT GCA CGA GTT ATA GTA TTA ACA GGA GCG GCA       1632
Tyr Ala Ser Ser Arg Asp Ala Arg Val Ile Val Leu Thr Gly Ala Ala
        530                 535                 540

TCC ACA GGA GTG GGA GGC CAA GTT AGT GTA AAT ATG CCT CTT CAG AAA       1680
Ser Thr Gly Val Gly Gly Gln Val Ser Val Asn Met Pro Leu Gln Lys
545                 550                 555                 560

ACT ATG GAA ATA GGG GAG AAC TTA ACA TCT AGA ACA TTT AGA TAT ACC       1728
Thr Met Glu Ile Gly Glu Asn Leu Thr Ser Arg Thr Phe Arg Tyr Thr
                    565                 570                 575

GAT TTT AGT AAT CCT TTT TCA TTT AGA GCT AAT CCA GAT ATA ATT GGG       1776
Asp Phe Ser Asn Pro Phe Ser Phe Arg Ala Asn Pro Asp Ile Ile Gly
                580                 585                 590

ATA AGT GAA CAA CCT CTA TTT GGT GCA GGT TCT ATT AGT AGC GGT GAA       1824
Ile Ser Glu Gln Pro Leu Phe Gly Ala Gly Ser Ile Ser Ser Gly Glu
            595                 600                 605

CTT TAT ATA GAT AAA ATT GAA ATT ATT CTA GCA GAT GCA ACA TTT GAA       1872
Leu Tyr Ile Asp Lys Ile Glu Ile Ile Leu Ala Asp Ala Thr Phe Glu
        610                 615                 620

GCA GAA TCT GAT TTA GAA AGA GCA CAA AAG GCG GTG AAT GCC CTG TTT       1920
Ala Glu Ser Asp Leu Glu Arg Ala Gln Lys Ala Val Asn Ala Leu Phe
625                 630                 635                 640

ACT TCT TCC AAT CAA ATC GGG TTA AAA ACC GAT GTG ACG GAT TAT CAT       1968
Thr Ser Ser Asn Gln Ile Gly Leu Lys Thr Asp Val Thr Asp Tyr His
                    645                 650                 655

ATT GAT CAA GTA TCC AAT TTA GTG GAT TGT TTA TCA GAT GAA TTT TGT       2016
Ile Asp Gln Val Ser Asn Leu Val Asp Cys Leu Ser Asp Glu Phe Cys
                660                 665                 670

CTG GAT GAA AAG CGA GAA TTG TCC GAG AAA GTC AAA CAT GCG AAG CGA       2064
Leu Asp Glu Lys Arg Glu Leu Ser Glu Lys Val Lys His Ala Lys Arg
            675                 680                 685

CTC AGT GAT GAG CGG AAT TTA CTT CAA GAT CCA AAC TTC AGA GGG ATC       2112
Leu Ser Asp Glu Arg Asn Leu Leu Gln Asp Pro Asn Phe Arg Gly Ile
        690                 695                 700

AAT AGA CAA CCA GAC CGT GGC TGG AGA GGA AGT ACA GAT ATT ACC ATC       2160
Asn Arg Gln Pro Asp Arg Gly Trp Arg Gly Ser Thr Asp Ile Thr Ile
705                 710                 715                 720
```

-continued

| | | |
|---|---|---|
| CAA GGA GGA GAT GAC GTA TTC AAA GAG AAT TAC GTC ACA CTA CCG GGT<br>Gln Gly Gly Asp Asp Val Phe Lys Glu Asn Tyr Val Thr Leu Pro Gly<br>                725                      730                    735 | 2208 |
| ACC GTT GAT GAG TGC TAT CCA ACG TAT TTA TAT CAG AAA ATA GAT GAG<br>Thr Val Asp Glu Cys Tyr Pro Thr Tyr Leu Tyr Gln Lys Ile Asp Glu<br>                740                      745                    750 | 2256 |
| TCG AAA TTA AAA GCT TAT ACC CGT TAT GAA TTA AGA GGG TAT ATC GAA<br>Ser Lys Leu Lys Ala Tyr Thr Arg Tyr Glu Leu Arg Gly Tyr Ile Glu<br>        755                      760                    765 | 2304 |
| GAT AGT CAA GAC TTA GAA ATC TAT TTG ATC CGT TAC AAT GCA AAA CAC<br>Asp Ser Gln Asp Leu Glu Ile Tyr Leu Ile Arg Tyr Asn Ala Lys His<br>770                      775                    780 | 2352 |
| GAA ATA GTA AAT GTG CCA GGC ACG GGT TCC TTA TGG CCG CTT TCA GCC<br>Glu Ile Val Asn Val Pro Gly Thr Gly Ser Leu Trp Pro Leu Ser Ala<br>785                      790                    795                    800 | 2400 |
| CAA AGT CCA ATC GGA AAG TGT GGA GAA CCG AAT CGA TGC GCG CCA CAC<br>Gln Ser Pro Ile Gly Lys Cys Gly Glu Pro Asn Arg Cys Ala Pro His<br>                      805                      810                    815 | 2448 |
| CTT GAA TGG AAT CCT GAT CTA GAT TGT TCC TGC AGA GAC GGG GAA AAA<br>Leu Glu Trp Asn Pro Asp Leu Asp Cys Ser Cys Arg Asp Gly Glu Lys<br>            820                      825                    830 | 2496 |
| TGT GCA CAT CAT TCC CAT CAT TTC ACC TTG GAT ATT GAT GTT GGA TGT<br>Cys Ala His His Ser His His Phe Thr Leu Asp Ile Asp Val Gly Cys<br>                835                      840                    845 | 2544 |
| ACA GAC TTA AAT GAG GAC TTA GGT GTA TGG GTG ATA TTC AAG ATT AAG<br>Thr Asp Leu Asn Glu Asp Leu Gly Val Trp Val Ile Phe Lys Ile Lys<br>850                      855                    860 | 2592 |
| ACG CAA GAT GGC CAT GCA AGA CTA GGG AAT CTA GAG TTT CTC GAA GAG<br>Thr Gln Asp Gly His Ala Arg Leu Gly Asn Leu Glu Phe Leu Glu Glu<br>865                      870                    875                    880 | 2640 |
| AAA CCA TTA TTA GGG GAA GCA CTA GCT CGT GTG AAA AGA GCG GAG AAG<br>Lys Pro Leu Leu Gly Glu Ala Leu Ala Arg Val Lys Arg Ala Glu Lys<br>                    885                      890                    895 | 2688 |
| AAG TGG AGA GAC AAA CGA GAG AAA CTG CAG TTG GAA ACA AAT ATT GTT<br>Lys Trp Arg Asp Lys Arg Glu Lys Leu Gln Leu Glu Thr Asn Ile Val<br>            900                      905                    910 | 2736 |
| TAT AAA GAG GCA AAA GAA TCT GTA GAT GCT TTA TTT GTA AAC TCT CAA<br>Tyr Lys Glu Ala Lys Glu Ser Val Asp Ala Leu Phe Val Asn Ser Gln<br>                915                      920                    925 | 2784 |
| TAT GAT AGA TTA CAA GTG GAT ACG AAC ATC GCG ATG ATT CAT GCG GCA<br>Tyr Asp Arg Leu Gln Val Asp Thr Asn Ile Ala Met Ile His Ala Ala<br>930                      935                    940 | 2832 |
| GAT AAA CGC GTT CAT AGA ATC CGG GAA GCG TAT CTG CCA GAG TTG TCT<br>Asp Lys Arg Val His Arg Ile Arg Glu Ala Tyr Leu Pro Glu Leu Ser<br>945                      950                    955                    960 | 2880 |
| GTG ATT CCA GGT GTC AAT GCG GCC ATT TTC GAA GAA TTA GAG GGA CGT<br>Val Ile Pro Gly Val Asn Ala Ala Ile Phe Glu Glu Leu Glu Gly Arg<br>                965                      970                    975 | 2928 |
| ATT TTT ACA GCG TAT TCC TTA TAT GAT GCG AGA AAT GTC ATT AAA AAT<br>Ile Phe Thr Ala Tyr Ser Leu Tyr Asp Ala Arg Asn Val Ile Lys Asn<br>            980                      985                    990 | 2976 |
| GGC GAT TTC AAT AAT GGC TTA TTA TGC TGG AAC GTG AAA GGT CAT GTA<br>Gly Asp Phe Asn Asn Gly Leu Leu Cys Trp Asn Val Lys Gly His Val<br>        995                    1000                    1005 | 3024 |
| GAT GTA GAA GAG CAA AAC AAC CAC CGT TCG GTC CTT GTT ATC CCA GAA<br>Asp Val Glu Glu Gln Asn Asn His Arg Ser Val Leu Val Ile Pro Glu<br>1010                    1015                    1020 | 3072 |
| TGG GAG GCA GAA GTG TCA CAA GAG GTT CGT GTC TGT CCA GGT CGT GGC<br>Trp Glu Ala Glu Val Ser Gln Glu Val Arg Val Cys Pro Gly Arg Gly | 3120 |

```
1025            1030            1035            1040
TAT ATC CTT CGT GTC ACA GCA TAT AAA GAG GGA TAT GGA GAG GGC TGC        3168
Tyr Ile Leu Arg Val Thr Ala Tyr Lys Glu Gly Tyr Gly Glu Gly Cys
                    1045            1050            1055

GTA ACG ATC CAT GAG ATC GAA GAC AAT ACA GAC GAA CTG AAA TTC AGC        3216
Val Thr Ile His Glu Ile Glu Asp Asn Thr Asp Glu Leu Lys Phe Ser
            1060            1065            1070

AAC TGT GTA GAA GAG GAA GTA TAT CCA AAC AAC ACA GTA ACG TGT AAT        3264
Asn Cys Val Glu Glu Glu Val Tyr Pro Asn Asn Thr Val Thr Cys Asn
        1075            1080            1085

AAT TAT ACT GGG ACT CAA GAA GAA TAT GAG GGT ACG TAC ACT TCT CGT        3312
Asn Tyr Thr Gly Thr Gln Glu Glu Tyr Glu Gly Thr Tyr Thr Ser Arg
    1090            1095            1100

AAT CAA GGA TAT GAC GAA GCC TAT GGT AAT AAC CCT TCC GTA CCA GCT        3360
Asn Gln Gly Tyr Asp Glu Ala Tyr Gly Asn Asn Pro Ser Val Pro Ala
1105            1110            1115            1120

GAT TAC GCT TCA GTC TAT GAA GAA AAA TCG TAT ACA GAT GGA CGA AGA        3408
Asp Tyr Ala Ser Val Tyr Glu Glu Lys Ser Tyr Thr Asp Gly Arg Arg
                1125            1130            1135

GAG AAT CCT TGT GAA TCT AAC AGA GGC TAT GGG GAT TAC ACA CCA CTA        3456
Glu Asn Pro Cys Glu Ser Asn Arg Gly Tyr Gly Asp Tyr Thr Pro Leu
            1140            1145            1150

CCG GCT GGT TAT GTA ACA AAG GAT TTA GAG TAC TTC CCA GAG ACC GAT        3504
Pro Ala Gly Tyr Val Thr Lys Asp Leu Glu Tyr Phe Pro Glu Thr Asp
        1155            1160            1165

AAG GTA TGG ATT GAG ATC GGA GAA ACA GAA GGA ACA TTC ATC GTG GAT        3552
Lys Val Trp Ile Glu Ile Gly Glu Thr Glu Gly Thr Phe Ile Val Asp
    1170            1175            1180

AGC GTG GAA TTA CTC CTT ATG GAG GAA                                     3579
Ser Val Glu Leu Leu Leu Met Glu Glu
1185            1190

(2) INFORMATION FOR SEQ ID NO: 8:

(i) SEQUENCE CHARACTERISTICS:
        (A) LENGTH: 1193 amino acids
        (B) TYPE: amino acid
        (D) TOPOLOGY: linear (ii) MOLECULE TYPE: protein (xi) SEQUENCE DESCRIPTION: SEQ ID NO: 8:

Met Asp Asn Asn Pro Asn Ile Asn Glu Cys Ile Pro Tyr Asn Cys Leu
 1               5                  10                  15

Ser Asn Pro Glu Val Glu Val Leu Gly Gly Glu Arg Ile Glu Thr Gly
                20                  25                  30

Tyr Thr Pro Ile Asp Ile Ser Leu Ser Leu Thr Gln Phe Leu Leu Ser
            35                  40                  45

Glu Phe Val Pro Gly Ala Gly Phe Val Leu Gly Leu Val Asp Ile Ile
        50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
```

-continued

```
            130                 135                 140
Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
                180                 185                 190

Tyr Asn Asp Leu Thr Arg Leu Ile Gly Asn Tyr Thr Asp His Ala Val
                195                 200                 205

Arg Trp Tyr Asn Thr Gly Leu Glu Arg Val Trp Gly Pro Asp Ser Arg
210                 215                 220

Asp Trp Ile Arg Tyr Asn Gln Phe Arg Arg Glu Leu Thr Leu Thr Val
225                 230                 235                 240

Leu Asp Ile Val Ser Leu Phe Pro Asn Tyr Asp Ser Arg Thr Tyr Pro
                245                 250                 255

Ile Arg Thr Val Ser Gln Leu Thr Arg Glu Ile Tyr Thr Asn Pro Val
                260                 265                 270

Leu Glu Asn Phe Asp Gly Ser Phe Arg Gly Ser Ala Gln Gly Ile Glu
                275                 280                 285

Gly Ser Ile Arg Ser Pro His Leu Met Asp Ile Leu Asn Ser Ile Thr
290                 295                 300

Ile Tyr Thr Asp Ala His Arg Gly Glu Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
                340                 345                 350

Gln Leu Gly Gln Gly Val Tyr Arg Thr Leu Ser Ser Thr Leu Tyr Arg
                355                 360                 365

Arg Pro Phe Asn Ile Gly Ile Asn Asn Gln Gln Leu Ser Val Leu Asp
370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
                420                 425                 430

Val Ser Met Phe Arg Ser Gly Phe Ser Asn Ser Ser Val Ser Ile Ile
                435                 440                 445

Arg Ala Pro Met Phe Ser Trp Ile His Arg Ser Ala Thr Leu Thr Asn
450                 455                 460

Thr Ile Asp Pro Glu Arg Ile Asn Gln Ile Pro Leu Val Lys Gly Phe
465                 470                 475                 480

Arg Val Trp Gly Gly Thr Ser Val Ile Thr Gly Pro Gly Phe Thr Gly
                485                 490                 495

Gly Asp Ile Leu Arg Arg Asn Thr Phe Gly Asp Phe Val Ser Leu Gln
                500                 505                 510

Val Asn Ile Asn Ser Pro Ile Thr Gln Arg Tyr Arg Leu Arg Phe Arg
                515                 520                 525

Tyr Ala Ser Ser Arg Asp Ala Arg Val Ile Val Leu Thr Gly Ala Ala
                530                 535                 540

Ser Thr Gly Val Gly Gly Gln Val Ser Val Asn Met Pro Leu Gln Lys
545                 550                 555                 560
```

-continued

```
Thr Met Glu Ile Gly Glu Asn Leu Thr Ser Arg Thr Phe Arg Tyr Thr
            565                 570                 575
Asp Phe Ser Asn Pro Phe Ser Phe Arg Ala Asn Pro Asp Ile Ile Gly
            580                 585                 590
Ile Ser Glu Gln Pro Leu Phe Gly Ala Gly Ser Ile Ser Ser Gly Glu
            595                 600                 605
Leu Tyr Ile Asp Lys Ile Glu Ile Ile Leu Ala Asp Ala Thr Phe Glu
            610                 615                 620
Ala Glu Ser Asp Leu Glu Arg Ala Gln Lys Ala Val Asn Ala Leu Phe
625                 630                 635                 640
Thr Ser Ser Asn Gln Ile Gly Leu Lys Thr Asp Val Thr Asp Tyr His
            645                 650                 655
Ile Asp Gln Val Ser Asn Leu Val Asp Cys Leu Ser Asp Glu Phe Cys
            660                 665                 670
Leu Asp Glu Lys Arg Glu Leu Ser Glu Lys Val Lys His Ala Lys Arg
            675                 680                 685
Leu Ser Asp Glu Arg Asn Leu Leu Gln Asp Pro Asn Phe Arg Gly Ile
            690                 695                 700
Asn Arg Gln Pro Asp Arg Gly Trp Arg Gly Ser Thr Asp Ile Thr Ile
705                 710                 715                 720
Gln Gly Gly Asp Asp Val Phe Lys Glu Asn Tyr Val Thr Leu Pro Gly
            725                 730                 735
Thr Val Asp Glu Cys Tyr Pro Thr Tyr Leu Tyr Gln Lys Ile Asp Glu
            740                 745                 750
Ser Lys Leu Lys Ala Tyr Thr Arg Tyr Glu Leu Arg Gly Tyr Ile Glu
            755                 760                 765
Asp Ser Gln Asp Leu Glu Ile Tyr Leu Ile Arg Tyr Asn Ala Lys His
            770                 775                 780
Glu Ile Val Asn Val Pro Gly Thr Gly Ser Leu Trp Pro Leu Ser Ala
785                 790                 795                 800
Gln Ser Pro Ile Gly Lys Cys Gly Glu Pro Asn Arg Cys Ala Pro His
            805                 810                 815
Leu Glu Trp Asn Pro Asp Leu Asp Cys Ser Cys Arg Asp Gly Glu Lys
            820                 825                 830
Cys Ala His His Ser His His Phe Thr Leu Asp Ile Asp Val Gly Cys
            835                 840                 845
Thr Asp Leu Asn Glu Asp Leu Gly Val Trp Val Ile Phe Lys Ile Lys
850                 855                 860
Thr Gln Asp Gly His Ala Arg Leu Gly Asn Leu Glu Phe Leu Glu Glu
865                 870                 875                 880
Lys Pro Leu Leu Gly Glu Ala Leu Ala Arg Val Lys Arg Ala Glu Lys
            885                 890                 895
Lys Trp Arg Asp Lys Arg Glu Lys Leu Gln Leu Glu Thr Asn Ile Val
            900                 905                 910
Tyr Lys Glu Ala Lys Glu Ser Val Asp Ala Leu Phe Val Asn Ser Gln
            915                 920                 925
Tyr Asp Arg Leu Gln Val Asp Thr Asn Ile Ala Met Ile His Ala Ala
            930                 935                 940
Asp Lys Arg Val His Arg Ile Arg Glu Ala Tyr Leu Pro Glu Leu Ser
945                 950                 955                 960
Val Ile Pro Gly Val Asn Ala Ala Ile Phe Glu Glu Leu Glu Gly Arg
            965                 970                 975
```

```
Ile Phe Thr Ala Tyr Ser Leu Tyr Asp Ala Arg Asn Val Ile Lys Asn
                980             985                 990

Gly Asp Phe Asn Asn Gly Leu Leu Cys Trp Asn Val Lys Gly His Val
            995                 1000                1005

Asp Val Glu Glu Gln Asn Asn His Arg Ser Val Leu Val Ile Pro Glu
        1010                1015                1020

Trp Glu Ala Glu Val Ser Gln Glu Val Arg Val Cys Pro Gly Arg Gly
1025                1030                1035                1040

Tyr Ile Leu Arg Val Thr Ala Tyr Lys Glu Gly Tyr Gly Glu Gly Cys
                1045                1050                1055

Val Thr Ile His Glu Ile Glu Asp Asn Thr Asp Glu Leu Lys Phe Ser
            1060                1065                1070

Asn Cys Val Glu Glu Val Tyr Pro Asn Asn Thr Val Thr Cys Asn
            1075                1080                1085

Asn Tyr Thr Gly Thr Gln Glu Glu Tyr Glu Gly Thr Tyr Thr Ser Arg
    1090                1095                1100

Asn Gln Gly Tyr Asp Glu Ala Tyr Gly Asn Asn Pro Ser Val Pro Ala
1105                1110                1115                1120

Asp Tyr Ala Ser Val Tyr Glu Glu Lys Ser Tyr Thr Asp Gly Arg Arg
                1125                1130                1135

Glu Asn Pro Cys Glu Ser Asn Arg Gly Tyr Gly Asp Tyr Thr Pro Leu
            1140                1145                1150

Pro Ala Gly Tyr Val Thr Lys Asp Leu Glu Tyr Phe Pro Glu Thr Asp
                1155                1160                1165

Lys Val Trp Ile Glu Ile Gly Glu Thr Glu Gly Thr Phe Ile Val Asp
    1170                1175                1180

Ser Val Glu Leu Leu Leu Met Glu Glu
1185                1190

(2) INFORMATION FOR SEQ ID NO: 9:

(i) SEQUENCE CHARACTERISTICS:
        (A) LENGTH: 3468 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Bacillus thuringiensis (ix) FEATURE:
        (A) NAME/KEY: CDS
        (B) LOCATION: 1..3468

(xi) SEQUENCE DESCRIPTION: SEQ ID NO: 9:

ATG AAT CAA AAT AAA CAC GGA ATT ATT GGC GCT TCC AAT TGT GGT TGT     48
Met Asn Gln Asn Lys His Gly Ile Ile Gly Ala Ser Asn Cys Gly Cys
1               5                   10                  15

GCA TCT GAT GAT GTT GCG AAA TAT CCT TTA GCC AAC AAT CCA TAT TCA     96
Ala Ser Asp Asp Val Ala Lys Tyr Pro Leu Ala Asn Asn Pro Tyr Ser
                20                  25                  30

TCT GCT TTA AAT TTA AAT TCT TGT CAA AAT AGT AGT ATT CTC AAC TGG    144
Ser Ala Leu Asn Leu Asn Ser Cys Gln Asn Ser Ser Ile Leu Asn Trp
        35                  40                  45

ATT AAC ATA ATA GGC GAT GCA GCA AAA GAA GCA GTA TCT ATT GGG ACA    192
Ile Asn Ile Ile Gly Asp Ala Ala Lys Glu Ala Val Ser Ile Gly Thr
    50                  55                  60

ACC ATA GTC TCT CTT ATC ACA GCA CCT TCT CTT ACT GGA TTA ATT TCA    240
```

```
Thr Ile Val Ser Leu Ile Thr Ala Pro Ser Leu Thr Gly Leu Ile Ser
 65                  70                  75                  80

ATA GTA TAT GAC CTT ATA GGT AAA GTA CTA GGA GGT AGT AGT GGA CAA        288
Ile Val Tyr Asp Leu Ile Gly Lys Val Leu Gly Gly Ser Ser Gly Gln
                     85                  90                  95

TCC ATA TCA GAT TTG TCT ATA TGT GAC TTA TTA TCT ATT ATT GAT TTA        336
Ser Ile Ser Asp Leu Ser Ile Cys Asp Leu Leu Ser Ile Ile Asp Leu
                100                 105                 110

CGG GTA AGT CAG AGT GTT TTA AAT GAT GGG ATT GCA GAT TTT AAT GGT        384
Arg Val Ser Gln Ser Val Leu Asn Asp Gly Ile Ala Asp Phe Asn Gly
            115                 120                 125

TCT GTA CTC TTA TAC AGG AAC TAT TTA GAG GCT CTG GAT AGC TGG AAT        432
Ser Val Leu Leu Tyr Arg Asn Tyr Leu Glu Ala Leu Asp Ser Trp Asn
        130                 135                 140

AAG AAT CCT AAT TCT GCT TCT GCT GAA GAA CTC CGT ACT CGT TTT AGA        480
Lys Asn Pro Asn Ser Ala Ser Ala Glu Glu Leu Arg Thr Arg Phe Arg
145                 150                 155                 160

ATC GCC GAC TCA GAA TTT GAT AGA ATT TTA ACC CGA GGG TCT TTA ACG        528
Ile Ala Asp Ser Glu Phe Asp Arg Ile Leu Thr Arg Gly Ser Leu Thr
                165                 170                 175

AAT GGT GGC TCG TTA GCT AGA CAA AAT GCC CAA ATA TTA TTA TTA CCT        576
Asn Gly Gly Ser Leu Ala Arg Gln Asn Ala Gln Ile Leu Leu Leu Pro
            180                 185                 190

TCT TTT GCG AGC GCT GCA TTT TTC CAT TTA TTA CTA CTA AGG GAT GCT        624
Ser Phe Ala Ser Ala Ala Phe Phe His Leu Leu Leu Leu Arg Asp Ala
        195                 200                 205

ACT AGA TAT GGC ACT AAT TGG GGG CTA TAC AAT GCT ACA CCT TTT ATA        672
Thr Arg Tyr Gly Thr Asn Trp Gly Leu Tyr Asn Ala Thr Pro Phe Ile
210                 215                 220

AAT TAT CAA TCA AAA CTA GTA GAG CTT ATT GAA CTA TAT ACT GAT TAT        720
Asn Tyr Gln Ser Lys Leu Val Glu Leu Ile Glu Leu Tyr Thr Asp Tyr
225                 230                 235                 240

TGC GTA CAT TGG TAT AAT CGA GGT TTC AAC GAA CTA AGA CAA CGA GGC        768
Cys Val His Trp Tyr Asn Arg Gly Phe Asn Glu Leu Arg Gln Arg Gly
                245                 250                 255

ACT AGT GCT ACA GCT TGG TTA GAA TTT CAT AGA TAT CGT AGA GAG ATG        816
Thr Ser Ala Thr Ala Trp Leu Glu Phe His Arg Tyr Arg Arg Glu Met
            260                 265                 270

ACA TTG ATG GTA TTA GAT ATA GTA GCA TCA TTT TCA AGT CTT GAT ATT        864
Thr Leu Met Val Leu Asp Ile Val Ala Ser Phe Ser Ser Leu Asp Ile
        275                 280                 285

ACT AAT TAC CCA ATA GAA ACA GAT TTT CAG TTG AGT AGG GTC ATT TAT        912
Thr Asn Tyr Pro Ile Glu Thr Asp Phe Gln Leu Ser Arg Val Ile Tyr
290                 295                 300

ACA GAT CCA ATT GGT TTT GTA CAT CGT AGT AGT CTT AGG GGA GAA AGT        960
Thr Asp Pro Ile Gly Phe Val His Arg Ser Ser Leu Arg Gly Glu Ser
305                 310                 315                 320

TGG TTT AGC TTT GTT AAT AGA GCT AAT TTC TCA GAT TTA GAA AAT GCA       1008
Trp Phe Ser Phe Val Asn Arg Ala Asn Phe Ser Asp Leu Glu Asn Ala
                325                 330                 335

ATA CCT AAT CCT AGA CCG TCT TGG TTT TTA AAT AAT ATG ATT ATA TCT       1056
Ile Pro Asn Pro Arg Pro Ser Trp Phe Leu Asn Asn Met Ile Ile Ser
            340                 345                 350

ACT GGT TCA CTT ACA TTG CCG GTT AGC CCA AGT ACT GAT AGA GCG AGG       1104
Thr Gly Ser Leu Thr Leu Pro Val Ser Pro Ser Thr Asp Arg Ala Arg
        355                 360                 365

GTA TGG TAT GGA AGT CGA GAT CGA ATT TCC CCT GCT AAT TCA CAA TTT       1152
Val Trp Tyr Gly Ser Arg Asp Arg Ile Ser Pro Ala Asn Ser Gln Phe
370                 375                 380
```

-continued

```
ATT ACT GAA CTA ATC TCT GGA CAA CAT ACG ACT GCT ACA CAA ACT ATT      1200
Ile Thr Glu Leu Ile Ser Gly Gln His Thr Thr Ala Thr Gln Thr Ile
385                 390                 395                 400

TTA GGG CGA AAT ATA TTT AGA GTA GAT TCT CAA GCT TGT AAT TTA AAT      1248
Leu Gly Arg Asn Ile Phe Arg Val Asp Ser Gln Ala Cys Asn Leu Asn
                405                 410                 415

GAT ACC ACA TAT GGA GTG AAT AGG GCG GTA TTT TAT CAT GAT GCG AGT      1296
Asp Thr Thr Tyr Gly Val Asn Arg Ala Val Phe Tyr His Asp Ala Ser
        420                 425                 430

GAA GGT TCT CAA AGA TCC GTG TAC GAG GGG TAT ATT CGA ACA ACT GGG      1344
Glu Gly Ser Gln Arg Ser Val Tyr Glu Gly Tyr Ile Arg Thr Thr Gly
            435                 440                 445

ATA GAT AAC CCT AGA GTT CAA AAT ATT AAC ACT TAT TTA CCT GGA GAA      1392
Ile Asp Asn Pro Arg Val Gln Asn Ile Asn Thr Tyr Leu Pro Gly Glu
450                 455                 460

AAT TCA GAT ATC CCA ACT CCA GAA GAC TAT ACT CAT ATA TTA AGC ACA      1440
Asn Ser Asp Ile Pro Thr Pro Glu Asp Tyr Thr His Ile Leu Ser Thr
465                 470                 475                 480

ACA ATA AAT TTA ACA GGA GGA CTT AGA CAA GTA GCA TCT AAT CGC CGT      1488
Thr Ile Asn Leu Thr Gly Gly Leu Arg Gln Val Ala Ser Asn Arg Arg
                485                 490                 495

TCA TCT TTA GTA ATG TAT GGT TGG ACA CAT AAA AGT CTG GCT CGT AAC      1536
Ser Ser Leu Val Met Tyr Gly Trp Thr His Lys Ser Leu Ala Arg Asn
        500                 505                 510

AAT ACC ATT AAT CCA GAT AGA ATT ACA CAG ATA CCA TTG ACG AAG GTT      1584
Asn Thr Ile Asn Pro Asp Arg Ile Thr Gln Ile Pro Leu Thr Lys Val
            515                 520                 525

GAT ACC CGA GGC ACA GGT GTT TCT TAT GTG AAT GAT CCA GGA TTT ATA      1632
Asp Thr Arg Gly Thr Gly Val Ser Tyr Val Asn Asp Pro Gly Phe Ile
530                 535                 540

GGA GGA GCT CTA CTT CAA AGG ACT GAC CAT GGT TCG CTT GGA GTA TTG      1680
Gly Gly Ala Leu Leu Gln Arg Thr Asp His Gly Ser Leu Gly Val Leu
545                 550                 555                 560

AGG GTC CAA TTT CCA CTT CAC TTA AGA CAA CAA TAT CGT ATT AGA GTC      1728
Arg Val Gln Phe Pro Leu His Leu Arg Gln Gln Tyr Arg Ile Arg Val
                565                 570                 575

CGT TAT GCT TCT ACA ACA AAT ATT CGA TTG AGT GTG AAT GGC AGT TTC      1776
Arg Tyr Ala Ser Thr Thr Asn Ile Arg Leu Ser Val Asn Gly Ser Phe
        580                 585                 590

GGT ACT ATT TCT CAA AAT CTC CCT AGT ACA ATG AGA TTA GGA GAG GAT      1824
Gly Thr Ile Ser Gln Asn Leu Pro Ser Thr Met Arg Leu Gly Glu Asp
            595                 600                 605

TTA AGA TAC GGA TCT TTT GCT ATA AGA GAG TTT AAT ACT TCT ATT AGA      1872
Leu Arg Tyr Gly Ser Phe Ala Ile Arg Glu Phe Asn Thr Ser Ile Arg
610                 615                 620

CCC ACT GCA AGT CCG GAC CAA ATT CGA TTG ACA ATA GAA CCA TCT TTT      1920
Pro Thr Ala Ser Pro Asp Gln Ile Arg Leu Thr Ile Glu Pro Ser Phe
625                 630                 635                 640

ATT AGA CAA GAG GTC TAT GTA GAT AGA ATT GAG TTC ATT CCA GTT AAT      1968
Ile Arg Gln Glu Val Tyr Val Asp Arg Ile Glu Phe Ile Pro Val Asn
                645                 650                 655

CCG ACG CGA GAG GCG AAA GAG GAT CTA GAA GCA GCA AAA AAA GCG GTG      2016
Pro Thr Arg Glu Ala Lys Glu Asp Leu Glu Ala Ala Lys Lys Ala Val
        660                 665                 670

GCG AGC TTG TTT ACA CGC ACA AGG GAC GGA TTA CAA GTA AAT GTG AAA      2064
Ala Ser Leu Phe Thr Arg Thr Arg Asp Gly Leu Gln Val Asn Val Lys
            675                 680                 685

GAT TAT CAA GTC GAT CAA GCG GCA AAT TTA GTG TCA TGC TTA TCA GAT      2112
Asp Tyr Gln Val Asp Gln Ala Ala Asn Leu Val Ser Cys Leu Ser Asp
690                 695                 700
```

```
                                        -continued

GAA CAA TAT GGG TAT GAC AAA AAG ATG TTA TTG GAA GCG GTA CGT GCG      2160
Glu Gln Tyr Gly Tyr Asp Lys Lys Met Leu Leu Glu Ala Val Arg Ala
705                 710                 715                 720

GCA AAA CGA CTT AGC CGA GAA CGC AAC TTA CTT CAG GAT CCA GAT TTT      2208
Ala Lys Arg Leu Ser Arg Glu Arg Asn Leu Leu Gln Asp Pro Asp Phe
                725                 730                 735

AAT ACA ATC AAT AGT ACA GAA GAA AAT GGA TGG AAA GCA AGT AAC GGC      2256
Asn Thr Ile Asn Ser Thr Glu Glu Asn Gly Trp Lys Ala Ser Asn Gly
            740                 745                 750

GTT ACT ATT AGT GAG GGC GGG CCA TTC TAT AAA GGC CGT GCA ATT CAG      2304
Val Thr Ile Ser Glu Gly Gly Pro Phe Tyr Lys Gly Arg Ala Ile Gln
        755                 760                 765

CTA GCA AGT GCA CGA GAA AAT TAC CCA ACA TAC ATC TAT CAA AAA GTA      2352
Leu Ala Ser Ala Arg Glu Asn Tyr Pro Thr Tyr Ile Tyr Gln Lys Val
770                 775                 780

GAT GCA TCG GAG TTA AAG CCG TAT ACA CGT TAT AGA CTG GAT GGG TTC      2400
Asp Ala Ser Glu Leu Lys Pro Tyr Thr Arg Tyr Arg Leu Asp Gly Phe
785                 790                 795                 800

GTG AAG AGT AGT CAA GAT TTA GAA ATT GAT CTC ATT CAC CAT CAT AAA      2448
Val Lys Ser Ser Gln Asp Leu Glu Ile Asp Leu Ile His His His Lys
                805                 810                 815

GTC CAT CTT GTG AAA AAT GTA CCA GAT AAT TTA GTA TCT GAT ACT TAC      2496
Val His Leu Val Lys Asn Val Pro Asp Asn Leu Val Ser Asp Thr Tyr
            820                 825                 830

CCA GAT GAT TCT TGT AGT GGA ATC AAT CGA TGT CAG GAA CAA CAG ATG      2544
Pro Asp Asp Ser Cys Ser Gly Ile Asn Arg Cys Gln Glu Gln Gln Met
        835                 840                 845

GTA AAT GCG CAA CTG GAA ACA GAG CAT CAT CAT CCG ATG GAT TGC TGT      2592
Val Asn Ala Gln Leu Glu Thr Glu His His His Pro Met Asp Cys Cys
850                 855                 860

GAA GCA GCT CAA ACA CAT GAG TTT TCT TCC TAT ATT GAT ACA GGG GAT      2640
Glu Ala Ala Gln Thr His Glu Phe Ser Ser Tyr Ile Asp Thr Gly Asp
865                 870                 875                 880

TTA AAT TCG AGT GTA GAC CAG GGA ATC TGG GCG ATC TTT AAA GTT CGA      2688
Leu Asn Ser Ser Val Asp Gln Gly Ile Trp Ala Ile Phe Lys Val Arg
                885                 890                 895

ACA ACC GAT GGT TAT GCG ACG TTA GGA AAT CTT GAA TTG GTA GAG GTC      2736
Thr Thr Asp Gly Tyr Ala Thr Leu Gly Asn Leu Glu Leu Val Glu Val
            900                 905                 910

GGA CCG TTA TCG GGT GAA TCT TTA GAA CGT GAA CAA AGG GAT AAT ACA      2784
Gly Pro Leu Ser Gly Glu Ser Leu Glu Arg Glu Gln Arg Asp Asn Thr
        915                 920                 925

AAA TGG AGT GCA GAG CTA GGA AGA AAG CGT GCA GAA ACA GAT CGC GTG      2832
Lys Trp Ser Ala Glu Leu Gly Arg Lys Arg Ala Glu Thr Asp Arg Val
930                 935                 940

TAT CAA GAT GCC AAA CAA TCC ATC AAT CAT TTA TTT GTG GAT TAT CAA      2880
Tyr Gln Asp Ala Lys Gln Ser Ile Asn His Leu Phe Val Asp Tyr Gln
945                 950                 955                 960

GAT CAA CAA TTA AAT CCA GAA ATA GGG ATG GCA GAT ATT ATG GAC GCT      2928
Asp Gln Gln Leu Asn Pro Glu Ile Gly Met Ala Asp Ile Met Asp Ala
                965                 970                 975

CAA AAT CTT GTC GCA TCA ATT TCA GAT GTA TAT AGC GAT GCC GTA CTG      2976
Gln Asn Leu Val Ala Ser Ile Ser Asp Val Tyr Ser Asp Ala Val Leu
            980                 985                 990

CAA ATC CCT GGA ATT AAC TAT GAG ATT TAC ACA GAG CTG TCC AAT CGC      3024
Gln Ile Pro Gly Ile Asn Tyr Glu Ile Tyr Thr Glu Leu Ser Asn Arg
        995                 1000                1005

TTA CAA CAA GCA TCG TAT CTG TAT ACG TCT CGA AAT GCG GTG CAA AAT      3072
Leu Gln Gln Ala Ser Tyr Leu Tyr Thr Ser Arg Asn Ala Val Gln Asn
```

```
                1010                1015                1020
GGG GAC TTT AAC AAC GGG CTA GAT AGC TGG AAT GCA ACA GCG GGT GCA          3120
Gly Asp Phe Asn Asn Gly Leu Asp Ser Trp Asn Ala Thr Ala Gly Ala
1025                1030                1035                1040

TCG GTA CAA CAG GAT GGC AAT ACG CAT TTC TTA GTT CTT TCT CAT TGG          3168
Ser Val Gln Gln Asp Gly Asn Thr His Phe Leu Val Leu Ser His Trp
            1045                1050                1055

GAT GCA CAA GTT TCT CAA CAA TTT AGA GTG CAG CCG AAT TGT AAA TAT          3216
Asp Ala Gln Val Ser Gln Gln Phe Arg Val Gln Pro Asn Cys Lys Tyr
        1060                1065                1070

GTA TTA CGT GTA ACA GCA GAG AAA GTA GGC GGC GGA GAC GGA TAC GTG          3264
Val Leu Arg Val Thr Ala Glu Lys Val Gly Gly Gly Asp Gly Tyr Val
    1075                1080                1085

ACT ATC CGG GAT GAT GCT CAT CAT ACA GAA ACG CTT ACA TTT AAT GCA          3312
Thr Ile Arg Asp Asp Ala His His Thr Glu Thr Leu Thr Phe Asn Ala
1090                1095                1100

TGT GAT TAT GAT ATA AAT GGC ACG TAC GTG ACT GAT AAT ACG TAT CTA          3360
Cys Asp Tyr Asp Ile Asn Gly Thr Tyr Val Thr Asp Asn Thr Tyr Leu
1105                1110                1115                1120

ACA AAA GAA GTG GTA TTC CAT CCG GAG ACA CAA CAC ATG TGG GTA GAG          3408
Thr Lys Glu Val Val Phe His Pro Glu Thr Gln His Met Trp Val Glu
            1125                1130                1135

GTA AAT GAA ACA GAA GGT GCA TTT CAT ATA GAT AGT ATT GAA TTC GTT          3456
Val Asn Glu Thr Glu Gly Ala Phe His Ile Asp Ser Ile Glu Phe Val
        1140                1145                1150

GAA ACA GAA AAG                                                          3468
Glu Thr Glu Lys
    1155
```

(2) INFORMATION FOR SEQ ID NO: 10:

(i) SEQUENCE CHARACTERISTICS:
        (A) LENGTH: 1156 amino acids
        (B) TYPE: amino acid
        (D) TOPOLOGY: linear (ii) MOLECULE TYPE: protein (xi) SEQUENCE DESCRIPTION: SEQ ID NO: 10:

```
Met Asn Gln Asn Lys His Gly Ile Ile Gly Ala Ser Asn Cys Gly Cys
1               5                   10                  15

Ala Ser Asp Asp Val Ala Lys Tyr Pro Leu Ala Asn Asn Pro Tyr Ser
            20                  25                  30

Ser Ala Leu Asn Leu Asn Ser Cys Gln Asn Ser Ser Ile Leu Asn Trp
        35                  40                  45

Ile Asn Ile Ile Gly Asp Ala Ala Lys Glu Ala Val Ser Ile Gly Thr
    50                  55                  60

Thr Ile Val Ser Leu Ile Thr Ala Pro Ser Leu Thr Gly Leu Ile Ser
65                  70                  75                  80

Ile Val Tyr Asp Leu Ile Gly Lys Val Leu Gly Gly Ser Ser Gly Gln
                85                  90                  95

Ser Ile Ser Asp Leu Ser Ile Cys Asp Leu Leu Ser Ile Ile Asp Leu
            100                 105                 110

Arg Val Ser Gln Ser Val Leu Asn Asp Gly Ile Ala Asp Phe Asn Gly
        115                 120                 125

Ser Val Leu Leu Tyr Arg Asn Tyr Leu Glu Ala Leu Asp Ser Trp Asn
    130                 135                 140

Lys Asn Pro Asn Ser Ala Ser Ala Glu Glu Leu Arg Thr Arg Phe Arg
145                 150                 155                 160
```

```
Ile Ala Asp Ser Glu Phe Asp Arg Ile Leu Thr Arg Gly Ser Leu Thr
                165                 170                 175
Asn Gly Gly Ser Leu Ala Arg Gln Asn Ala Gln Ile Leu Leu Leu Pro
            180                 185                 190
Ser Phe Ala Ser Ala Ala Phe Phe His Leu Leu Leu Arg Asp Ala
        195                 200                 205
Thr Arg Tyr Gly Thr Asn Trp Gly Leu Tyr Asn Ala Thr Pro Phe Ile
    210                 215                 220
Asn Tyr Gln Ser Lys Leu Val Glu Leu Ile Glu Leu Tyr Thr Asp Tyr
225                 230                 235                 240
Cys Val His Trp Tyr Asn Arg Gly Phe Asn Glu Leu Arg Gln Arg Gly
                245                 250                 255
Thr Ser Ala Thr Ala Trp Leu Glu Phe His Arg Tyr Arg Arg Glu Met
            260                 265                 270
Thr Leu Met Val Leu Asp Ile Val Ala Ser Phe Ser Ser Leu Asp Ile
        275                 280                 285
Thr Asn Tyr Pro Ile Glu Thr Asp Phe Gln Leu Ser Arg Val Ile Tyr
    290                 295                 300
Thr Asp Pro Ile Gly Phe Val His Arg Ser Ser Leu Arg Gly Glu Ser
305                 310                 315                 320
Trp Phe Ser Phe Val Asn Arg Ala Asn Phe Ser Asp Leu Glu Asn Ala
                325                 330                 335
Ile Pro Asn Pro Arg Pro Ser Trp Phe Leu Asn Asn Met Ile Ile Ser
            340                 345                 350
Thr Gly Ser Leu Thr Leu Pro Val Ser Pro Ser Thr Asp Arg Ala Arg
        355                 360                 365
Val Trp Tyr Gly Ser Arg Asp Arg Ile Ser Pro Ala Asn Ser Gln Phe
    370                 375                 380
Ile Thr Glu Leu Ile Ser Gly Gln His Thr Thr Ala Thr Gln Thr Ile
385                 390                 395                 400
Leu Gly Arg Asn Ile Phe Arg Val Asp Ser Gln Ala Cys Asn Leu Asn
                405                 410                 415
Asp Thr Thr Tyr Gly Val Asn Arg Ala Val Phe Tyr His Asp Ala Ser
            420                 425                 430
Glu Gly Ser Gln Arg Ser Val Tyr Glu Gly Tyr Ile Arg Thr Thr Gly
        435                 440                 445
Ile Asp Asn Pro Arg Val Gln Asn Ile Asn Thr Tyr Leu Pro Gly Glu
    450                 455                 460
Asn Ser Asp Ile Pro Thr Pro Glu Asp Tyr Thr His Ile Leu Ser Thr
465                 470                 475                 480
Thr Ile Asn Leu Thr Gly Gly Leu Arg Gln Val Ala Ser Asn Arg Arg
                485                 490                 495
Ser Ser Leu Val Met Tyr Gly Trp Thr His Lys Ser Leu Ala Arg Asn
            500                 505                 510
Asn Thr Ile Asn Pro Asp Arg Ile Thr Gln Ile Pro Leu Thr Lys Val
        515                 520                 525
Asp Thr Arg Gly Thr Gly Val Ser Tyr Val Asn Asp Pro Gly Phe Ile
    530                 535                 540
Gly Gly Ala Leu Leu Gln Arg Thr Asp His Gly Ser Leu Gly Val Leu
545                 550                 555                 560
Arg Val Gln Phe Pro Leu His Leu Arg Gln Gln Tyr Arg Ile Arg Val
                565                 570                 575
```

-continued

```
Arg Tyr Ala Ser Thr Thr Asn Ile Arg Leu Ser Val Asn Gly Ser Phe
            580                 585                 590
Gly Thr Ile Ser Gln Asn Leu Pro Ser Thr Met Arg Leu Gly Glu Asp
        595                 600                 605
Leu Arg Tyr Gly Ser Phe Ala Ile Arg Glu Phe Asn Thr Ser Ile Arg
    610                 615                 620
Pro Thr Ala Ser Pro Asp Gln Ile Arg Leu Thr Ile Glu Pro Ser Phe
625                 630                 635                 640
Ile Arg Gln Glu Val Tyr Val Asp Arg Ile Glu Phe Ile Pro Val Asn
            645                 650                 655
Pro Thr Arg Glu Ala Lys Glu Asp Leu Glu Ala Ala Lys Lys Ala Val
        660                 665                 670
Ala Ser Leu Phe Thr Arg Thr Arg Asp Gly Leu Gln Val Asn Val Lys
    675                 680                 685
Asp Tyr Gln Val Asp Gln Ala Ala Asn Leu Val Ser Cys Leu Ser Asp
690                 695                 700
Glu Gln Tyr Gly Tyr Asp Lys Lys Met Leu Leu Glu Ala Val Arg Ala
705                 710                 715                 720
Ala Lys Arg Leu Ser Arg Glu Arg Asn Leu Leu Gln Asp Pro Asp Phe
            725                 730                 735
Asn Thr Ile Asn Ser Thr Glu Glu Asn Gly Trp Lys Ala Ser Asn Gly
        740                 745                 750
Val Thr Ile Ser Glu Gly Gly Pro Phe Tyr Lys Gly Arg Ala Ile Gln
    755                 760                 765
Leu Ala Ser Ala Arg Glu Asn Tyr Pro Thr Tyr Ile Tyr Gln Lys Val
    770                 775                 780
Asp Ala Ser Glu Leu Lys Pro Tyr Thr Arg Tyr Arg Leu Asp Gly Phe
785                 790                 795                 800
Val Lys Ser Ser Gln Asp Leu Glu Ile Asp Leu Ile His His Lys
            805                 810                 815
Val His Leu Val Lys Asn Val Pro Asp Asn Leu Val Ser Asp Thr Tyr
        820                 825                 830
Pro Asp Asp Ser Cys Ser Gly Ile Asn Arg Cys Gln Glu Gln Gln Met
835                 840                 845
Val Asn Ala Gln Leu Glu Thr Glu His His Pro Met Asp Cys Cys
850                 855                 860
Glu Ala Ala Gln Thr His Glu Phe Ser Ser Tyr Ile Asp Thr Gly Asp
865                 870                 875                 880
Leu Asn Ser Ser Val Asp Gln Gly Ile Trp Ala Ile Phe Lys Val Arg
            885                 890                 895
Thr Thr Asp Gly Tyr Ala Thr Leu Gly Asn Leu Glu Leu Val Glu Val
        900                 905                 910
Gly Pro Leu Ser Gly Glu Ser Leu Glu Arg Glu Gln Arg Asp Asn Thr
    915                 920                 925
Lys Trp Ser Ala Glu Leu Gly Arg Lys Arg Ala Glu Thr Asp Arg Val
    930                 935                 940
Tyr Gln Asp Ala Lys Gln Ser Ile Asn His Leu Phe Val Asp Tyr Gln
945                 950                 955                 960
Asp Gln Gln Leu Asn Pro Glu Ile Gly Met Ala Asp Ile Met Asp Ala
            965                 970                 975
Gln Asn Leu Val Ala Ser Ile Ser Asp Val Tyr Ser Asp Ala Val Leu
        980                 985                 990
Gln Ile Pro Gly Ile Asn Tyr Glu Ile Tyr Thr Glu Leu Ser Asn Arg
```

-continued

```
                995               1000                1005
Leu Gln Gln Ala Ser Tyr Leu Tyr Thr Ser Arg Asn Ala Val Gln Asn
    1010                1015                1020

Gly Asp Phe Asn Asn Gly Leu Asp Ser Trp Asn Ala Thr Ala Gly Ala
1025                1030                1035                1040

Ser Val Gln Gln Asp Gly Asn Thr His Phe Leu Val Leu Ser His Trp
                1045                1050                1055

Asp Ala Gln Val Ser Gln Gln Phe Arg Val Gln Pro Asn Cys Lys Tyr
            1060                1065                1070

Val Leu Arg Val Thr Ala Glu Lys Val Gly Gly Gly Asp Gly Tyr Val
        1075                1080                1085

Thr Ile Arg Asp Asp Ala His His Thr Glu Thr Leu Thr Phe Asn Ala
    1090                1095                1100

Cys Asp Tyr Asp Ile Asn Gly Thr Tyr Val Thr Asp Asn Thr Tyr Leu
1105                1110                1115                1120

Thr Lys Glu Val Val Phe His Pro Glu Thr Gln His Met Trp Val Glu
                1125                1130                1135

Val Asn Glu Thr Glu Gly Ala Phe His Ile Asp Ser Ile Glu Phe Val
            1140                1145                1150

Glu Thr Glu Lys
        1155

(2) INFORMATION FOR SEQ ID NO: 11:

(i) SEQUENCE CHARACTERISTICS:
          (A) LENGTH: 3726 base pairs
          (B) TYPE: nucleic acid
          (C) STRANDEDNESS: single
          (D) TOPOLOGY: linear (ii) MOLECULE TYPE: cDNA (ix) FEATURE:
          (A) NAME/KEY: CDS
          (B) LOCATION: 1..3726

(xi) SEQUENCE DESCRIPTION: SEQ ID NO: 11:

ATG AAT CAA AAT AAA CAC GGA ATT ATT GGC GCT TCC AAT TGT GGT TGT         48
Met Asn Gln Asn Lys His Gly Ile Ile Gly Ala Ser Asn Cys Gly Cys
1               5                   10                  15

GCA TCT GAT GAT GTT GCG AAA TAT CCT TTA GCC AAC AAT CCA TAT TCA         96
Ala Ser Asp Asp Val Ala Lys Tyr Pro Leu Ala Asn Asn Pro Tyr Ser
                20                  25                  30

TCT GCT TTA AAT TTA AAT TCT TGT CAA AAT AGT AGT ATT CTC AAC TGG        144
Ser Ala Leu Asn Leu Asn Ser Cys Gln Asn Ser Ser Ile Leu Asn Trp
        35                  40                  45

ATT AAC ATA ATA GGC GAT GCA GCA AAA GAA GCA GTA TCT ATT GGG ACA        192
Ile Asn Ile Ile Gly Asp Ala Ala Lys Glu Ala Val Ser Ile Gly Thr
    50                  55                  60

ACC ATA GTC TCT CTT ATC ACA GCA CCT TCT CTT ACT GGA TTA ATT TCA        240
Thr Ile Val Ser Leu Ile Thr Ala Pro Ser Leu Thr Gly Leu Ile Ser
65                  70                  75                  80

ATA GTA TAT GAC CTT ATA GGT AAA GTA CTA GGA GGT AGT AGT GGA CAA        288
Ile Val Tyr Asp Leu Ile Gly Lys Val Leu Gly Gly Ser Ser Gly Gln
                85                  90                  95

TCC ATA TCA GAT TTG TCT ATA TGT GAC TTA TTA TCT ATT ATT GAT TTA        336
Ser Ile Ser Asp Leu Ser Ile Cys Asp Leu Leu Ser Ile Ile Asp Leu
            100                 105                 110

CGG GTA AGT CAG AGT GTT TTA AAT GAT GGG ATT GCA GAT TTT AAT GGT        384
Arg Val Ser Gln Ser Val Leu Asn Asp Gly Ile Ala Asp Phe Asn Gly
```

-continued

```
              115                 120                 125
TCT GTA CTC TTA TAC AGG AAC TAT TTA GAG GCT CTG GAT AGC TGG AAT      432
Ser Val Leu Leu Tyr Arg Asn Tyr Leu Glu Ala Leu Asp Ser Trp Asn
130                 135                 140

AAG AAT CCT AAT TCT GCT TCT GCT GAA GAA CTC CGT ACT CGT TTT AGA      480
Lys Asn Pro Asn Ser Ala Ser Ala Glu Glu Leu Arg Thr Arg Phe Arg
145                 150                 155                 160

ATC GCC GAC TCA GAA TTT GAT AGA ATT TTA ACC CGA GGG TCT TTA ACG      528
Ile Ala Asp Ser Glu Phe Asp Arg Ile Leu Thr Arg Gly Ser Leu Thr
                165                 170                 175

AAT GGT GGC TCG TTA GCT AGA CAA AAT GCC CAA ATA TTA TTA TTA CCT      576
Asn Gly Gly Ser Leu Ala Arg Gln Asn Ala Gln Ile Leu Leu Leu Pro
            180                 185                 190

TCT TTT GCG AGC GCT GCA TTT TTC CAT TTA TTA CTA CTA AGG GAT GCT      624
Ser Phe Ala Ser Ala Ala Phe Phe His Leu Leu Leu Leu Arg Asp Ala
        195                 200                 205

ACT AGA TAT GGC ACT AAT TGG GGG CTA TAC AAT GCT ACA CCT TTT ATA      672
Thr Arg Tyr Gly Thr Asn Trp Gly Leu Tyr Asn Ala Thr Pro Phe Ile
    210                 215                 220

AAT TAT CAA TCA AAA CTA GTA GAG CTT ATT GAA CTA TAT ACT GAT TAT      720
Asn Tyr Gln Ser Lys Leu Val Glu Leu Ile Glu Leu Tyr Thr Asp Tyr
225                 230                 235                 240

TGC GTA CAT TGG TAT AAT CGA GGT TTC AAC GAA CTA AGA CAA CGA GGC      768
Cys Val His Trp Tyr Asn Arg Gly Phe Asn Glu Leu Arg Gln Arg Gly
                245                 250                 255

ACT AGT GCT ACA GCT TGG TTA GAA TTT CAT AGA TAT CGT AGA GAG ATG      816
Thr Ser Ala Thr Ala Trp Leu Glu Phe His Arg Tyr Arg Arg Glu Met
            260                 265                 270

ACA TTG ATG GTA TTA GAT ATA GTA GCA TCA TTT TCA AGT CTT GAT ATT      864
Thr Leu Met Val Leu Asp Ile Val Ala Ser Phe Ser Ser Leu Asp Ile
        275                 280                 285

ACT AAT TAC CCA ATA GAA ACA GAT TTT CAG TTG AGT AGG GTC ATT TAT      912
Thr Asn Tyr Pro Ile Glu Thr Asp Phe Gln Leu Ser Arg Val Ile Tyr
    290                 295                 300

ACA GAT CCA ATT GGT TTT GTA CAT CGT AGT AGT CTT AGG GGA GAA AGT      960
Thr Asp Pro Ile Gly Phe Val His Arg Ser Ser Leu Arg Gly Glu Ser
305                 310                 315                 320

TGG TTT AGC TTT GTT AAT AGA GCT AAT TTC TCA GAT TTA GAA AAT GCA     1008
Trp Phe Ser Phe Val Asn Arg Ala Asn Phe Ser Asp Leu Glu Asn Ala
                325                 330                 335

ATA CCT AAT CCT AGA CCG TCT TGG TTT TTA AAT AAT ATG ATT ATA TCT     1056
Ile Pro Asn Pro Arg Pro Ser Trp Phe Leu Asn Asn Met Ile Ile Ser
            340                 345                 350

ACT GGT TCA CTT ACA TTG CCG GTT AGC CCA AGT ACT GAT AGA GCG AGG     1104
Thr Gly Ser Leu Thr Leu Pro Val Ser Pro Ser Thr Asp Arg Ala Arg
        355                 360                 365

GTA TGG TAT GGA AGT CGA GAT CGA ATT TCC CCT GCT AAT TCA CAA TTT     1152
Val Trp Tyr Gly Ser Arg Asp Arg Ile Ser Pro Ala Asn Ser Gln Phe
    370                 375                 380

ATT ACT GAA CTA ATC TCT GGA CAA CAT ACG ACT GCT ACA CAA ACT ATT     1200
Ile Thr Glu Leu Ile Ser Gly Gln His Thr Thr Ala Thr Gln Thr Ile
385                 390                 395                 400

TTA GGG CGA AAT ATA TTT AGA GTA GAT TCT CAA GCT TGT AAT TTA AAT     1248
Leu Gly Arg Asn Ile Phe Arg Val Asp Ser Gln Ala Cys Asn Leu Asn
                405                 410                 415

GAT ACC ACA TAT GGA GTG AAT AGG GCG GTA TTT TAT CAT GAT GCG AGT     1296
Asp Thr Thr Tyr Gly Val Asn Arg Ala Val Phe Tyr His Asp Ala Ser
            420                 425                 430

GAA GGT TCT CAA AGA TCC GTG TAC GAG GGG TAT ATT CGA ACA ACT GGG     1344
Glu Gly Ser Gln Arg Ser Val Tyr Glu Gly Tyr Ile Arg Thr Thr Gly
```

```
                Glu Gly Ser Gln Arg Ser Val Tyr Glu Gly Tyr Ile Arg Thr Thr Gly
                            435                 440                 445

ATA GAT AAC CCT AGA GTT CAA AAT ATT AAC ACT TAT TTA CCT GGA GAA                    1392
Ile Asp Asn Pro Arg Val Gln Asn Ile Asn Thr Tyr Leu Pro Gly Glu
            450                 455                 460

AAT TCA GAT ATC CCA ACT CCA GAA GAC TAT ACT CAT ATA TTA AGC ACA                    1440
Asn Ser Asp Ile Pro Thr Pro Glu Asp Tyr Thr His Ile Leu Ser Thr
465                 470                 475                 480

ACA ATA AAT TTA ACA GGA GGA CTT AGA CAA GTA GCA TCT AAT CGC CGT                    1488
Thr Ile Asn Leu Thr Gly Gly Leu Arg Gln Val Ala Ser Asn Arg Arg
                485                 490                 495

TCA TCT TTA GTA ATG TAT GGT TGG ACA CAT AAA AGT CTG GCT CGT AAC                    1536
Ser Ser Leu Val Met Tyr Gly Trp Thr His Lys Ser Leu Ala Arg Asn
            500                 505                 510

AAT ACC ATT AAT CCA GAT AGA ATT ACA CAG ATA CCT TTA GTG AAA GGA                    1584
Asn Thr Ile Asn Pro Asp Arg Ile Thr Gln Ile Pro Leu Val Lys Gly
            515                 520                 525

TTT AGA GTT TGG GGG GGC ACC TCT GTC ATT ACA GGA CCA GGA TTT ACA                    1632
Phe Arg Val Trp Gly Gly Thr Ser Val Ile Thr Gly Pro Gly Phe Thr
            530                 535                 540

GGA GGG GAT ATC CTT CGA AGA AAT ACC TTT GGT GAT TTT GTA TCT CTA                    1680
Gly Gly Asp Ile Leu Arg Arg Asn Thr Phe Gly Asp Phe Val Ser Leu
545                 550                 555                 560

CAA GTC AAT ATT AAT TCA CCA ATT ACC CAA AGA TAC CGT TTA AGA TTT                    1728
Gln Val Asn Ile Asn Ser Pro Ile Thr Gln Arg Tyr Arg Leu Arg Phe
                565                 570                 575

CGT TAC GCT TCC AGT AGG GAT GCA CGA GTT ATA GTA TTA ACA GGA GCG                    1776
Arg Tyr Ala Ser Ser Arg Asp Ala Arg Val Ile Val Leu Thr Gly Ala
            580                 585                 590

GCA TCC ACA GGA GTG GGA GGC CAA GTT AGT GTA AAT ATG CCT CTT CAG                    1824
Ala Ser Thr Gly Val Gly Gly Gln Val Ser Val Asn Met Pro Leu Gln
            595                 600                 605

AAA ACT ATG GAA ATA GGG GAG AAC TTA ACA TCT AGA ACA TTT AGA TAT                    1872
Lys Thr Met Glu Ile Gly Glu Asn Leu Thr Ser Arg Thr Phe Arg Tyr
            610                 615                 620

ACC GAT TTT AGT AAT CCT TTT TCA TTT AGA GCT AAT CCA GAT ATA ATT                    1920
Thr Asp Phe Ser Asn Pro Phe Ser Phe Arg Ala Asn Pro Asp Ile Ile
625                 630                 635                 640

GGG ATA AGT GAA CAA CCT CTA TTT GGT GCA GGT TCT ATT AGT AGC GGT                    1968
Gly Ile Ser Glu Gln Pro Leu Phe Gly Ala Gly Ser Ile Ser Ser Gly
                645                 650                 655

GAA CTT TAT ATA GAT AAA ATT GAA ATT ATT CTA GCA GAT GCA ACA TTT                    2016
Glu Leu Tyr Ile Asp Lys Ile Glu Ile Ile Leu Ala Asp Ala Thr Phe
            660                 665                 670

GAA GCA GAA TCT GAT TTA GAA AGA GCA CAA AAG GCG GTG AAT GCC CTG                    2064
Glu Ala Glu Ser Asp Leu Glu Arg Ala Gln Lys Ala Val Asn Ala Leu
            675                 680                 685

TTT ACT TCT TCC AAT CAA ATC GGG TTA AAA ACC GAT GTG ACG GAT TAT                    2112
Phe Thr Ser Ser Asn Gln Ile Gly Leu Lys Thr Asp Val Thr Asp Tyr
            690                 695                 700

CAT ATT GAT CAA GTA TCC AAT TTA GTG GAT TGT TTA TCA GAT GAA TTT                    2160
His Ile Asp Gln Val Ser Asn Leu Val Asp Cys Leu Ser Asp Glu Phe
705                 710                 715                 720

TGT CTG GAT GAA AAG CGA GAA TTG TCC GAG AAA GTC AAA CAT GCG AAG                    2208
Cys Leu Asp Glu Lys Arg Glu Leu Ser Glu Lys Val Lys His Ala Lys
                725                 730                 735

CGA CTC AGT GAT GAG CGG AAT TTA CTT CAA GAT CCA AAC TTC AGA GGG                    2256
Arg Leu Ser Asp Glu Arg Asn Leu Leu Gln Asp Pro Asn Phe Arg Gly
            740                 745                 750
```

```
ATC AAT AGA CAA CCA GAC CGT GGC TGG AGA GGA AGT ACA GAT ATT ACC    2304
Ile Asn Arg Gln Pro Asp Arg Gly Trp Arg Gly Ser Thr Asp Ile Thr
            755                 760                 765

ATC CAA GGA GGA GAT GAC GTA TTC AAA GAG AAT TAC GTC ACA CTA CCG    2352
Ile Gln Gly Gly Asp Asp Val Phe Lys Glu Asn Tyr Val Thr Leu Pro
        770                 775                 780

GGT ACC GTT GAT GAG TGC TAT CCA ACG TAT TTA TAT CAG AAA ATA GAT    2400
Gly Thr Val Asp Glu Cys Tyr Pro Thr Tyr Leu Tyr Gln Lys Ile Asp
785                 790                 795                 800

GAG TCG AAA TTA AAA GCT TAT ACC CGT TAT GAA TTA AGA GGG TAT ATC    2448
Glu Ser Lys Leu Lys Ala Tyr Thr Arg Tyr Glu Leu Arg Gly Tyr Ile
            805                 810                 815

GAA GAT AGT CAA GAC TTA GAA ATC TAT TTG ATC CGT TAC AAT GCA AAA    2496
Glu Asp Ser Gln Asp Leu Glu Ile Tyr Leu Ile Arg Tyr Asn Ala Lys
        820                 825                 830

CAC GAA ATA GTA AAT GTG CCA GGC ACG GGT TCC TTA TGG CCG CTT TCA    2544
His Glu Ile Val Asn Val Pro Gly Thr Gly Ser Leu Trp Pro Leu Ser
            835                 840                 845

GCC CAA AGT CCA ATC GGA AAG TGT GGA GAA CCG AAT CGA TGC GCG CCA    2592
Ala Gln Ser Pro Ile Gly Lys Cys Gly Glu Pro Asn Arg Cys Ala Pro
850                 855                 860

CAC CTT GAA TGG AAT CCT GAT CTA GAT TGT TCC TGC AGA GAC GGG GAA    2640
His Leu Glu Trp Asn Pro Asp Leu Asp Cys Ser Cys Arg Asp Gly Glu
865                 870                 875                 880

AAA TGT GCA CAT CAT TCC CAT CAT TTC ACC TTG GAT ATT GAT GTT GGA    2688
Lys Cys Ala His His Ser His His Phe Thr Leu Asp Ile Asp Val Gly
            885                 890                 895

TGT ACA GAC TTA AAT GAG GAC TTA GGT GTA TGG GTG ATA TTC AAG ATT    2736
Cys Thr Asp Leu Asn Glu Asp Leu Gly Val Trp Val Ile Phe Lys Ile
        900                 905                 910

AAG ACG CAA GAT GGC CAT GCA AGA CTA GGG AAT CTA GAG TTT CTC GAA    2784
Lys Thr Gln Asp Gly His Ala Arg Leu Gly Asn Leu Glu Phe Leu Glu
            915                 920                 925

GAG AAA CCA TTA TTA GGG GAA GCA CTA GCT CGT GTG AAA AGA GCG GAG    2832
Glu Lys Pro Leu Leu Gly Glu Ala Leu Ala Arg Val Lys Arg Ala Glu
930                 935                 940

AAG AAG TGG AGA GAC AAA CGA GAG AAA CTG CAG TTG GAA ACA AAT ATT    2880
Lys Lys Trp Arg Asp Lys Arg Glu Lys Leu Gln Leu Glu Thr Asn Ile
945                 950                 955                 960

GTT TAT AAA GAG GCA AAA GAA TCT GTA GAT GCT TTA TTT GTA AAC TCT    2928
Val Tyr Lys Glu Ala Lys Glu Ser Val Asp Ala Leu Phe Val Asn Ser
            965                 970                 975

CAA TAT GAT AGA TTA CAA GTG GAT ACG AAC ATC GCG ATG ATT CAT GCG    2976
Gln Tyr Asp Arg Leu Gln Val Asp Thr Asn Ile Ala Met Ile His Ala
        980                 985                 990

GCA GAT AAA CGC GTT CAT AGA ATC CGG GAA GCG TAT CTG CCA GAG TTG    3024
Ala Asp Lys Arg Val His Arg Ile Arg Glu Ala Tyr Leu Pro Glu Leu
            995                 1000                1005

TCT GTG ATT CCA GGT GTC AAT GCG GCC ATT TTC GAA GAA TTA GAG GGA    3072
Ser Val Ile Pro Gly Val Asn Ala Ala Ile Phe Glu Glu Leu Glu Gly
        1010                1015                1020

CGT ATT TTT ACA GCG TAT TCC TTA TAT GAT GCG AGA AAT GTC ATT AAA    3120
Arg Ile Phe Thr Ala Tyr Ser Leu Tyr Asp Ala Arg Asn Val Ile Lys
1025                1030                1035                1040

AAT GGC GAT TTC AAT AAT GGC TTA TTA TGC TGG AAC GTG AAA GGT CAT    3168
Asn Gly Asp Phe Asn Asn Gly Leu Leu Cys Trp Asn Val Lys Gly His
                    1045                1050                1055

GTA GAT GTA GAA GAG CAA AAC AAC CAC CGT TCG GTC CTT GTT ATC CCA    3216
Val Asp Val Glu Glu Gln Asn Asn His Arg Ser Val Leu Val Ile Pro
            1060                1065                1070
```

-continued

```
GAA TGG GAG GCA GAA GTG TCA CAA GAG GTT CGT GTC TGT CCA GGT CGT      3264
Glu Trp Glu Ala Glu Val Ser Gln Glu Val Arg Val Cys Pro Gly Arg
        1075                1080                1085

GGC TAT ATC CTT CGT GTC ACA GCA TAT AAA GAG GGA TAT GGA GAG GGC      3312
Gly Tyr Ile Leu Arg Val Thr Ala Tyr Lys Glu Gly Tyr Gly Glu Gly
    1090                1095                1100

TGC GTA ACG ATC CAT GAG ATC GAA GAC AAT ACA GAC GAA CTG AAA TTC      3360
Cys Val Thr Ile His Glu Ile Glu Asp Asn Thr Asp Glu Leu Lys Phe
1105                1110                1115                1120

AGC AAC TGT GTA GAA GAG GAA GTA TAT CCA AAC AAC ACA GTA ACG TGT      3408
Ser Asn Cys Val Glu Glu Glu Val Tyr Pro Asn Asn Thr Val Thr Cys
                1125                1130                1135

AAT AAT TAT ACT GGG ACT CAA GAA GAA TAT GAG GGT ACG TAC ACT TCT      3456
Asn Asn Tyr Thr Gly Thr Gln Glu Glu Tyr Glu Gly Thr Tyr Thr Ser
            1140                1145                1150

CGT AAT CAA GGA TAT GAC GAA GCC TAT GGT AAT AAC CCT TCC GTA CCA      3504
Arg Asn Gln Gly Tyr Asp Glu Ala Tyr Gly Asn Asn Pro Ser Val Pro
        1155                1160                1165

GCT GAT TAC GCT TCA GTC TAT GAA GAA AAA TCG TAT ACA GAT GGA CGA      3552
Ala Asp Tyr Ala Ser Val Tyr Glu Glu Lys Ser Tyr Thr Asp Gly Arg
    1170                1175                1180

AGA GAG AAT CCT TGT GAA TCT AAC AGA GGC TAT GGG GAT TAC ACA CCA      3600
Arg Glu Asn Pro Cys Glu Ser Asn Arg Gly Tyr Gly Asp Tyr Thr Pro
1185                1190                1195                1200

CTA CCG GCT GGT TAT GTA ACA AAG GAT TTA GAG TAC TTC CCA GAG ACC      3648
Leu Pro Ala Gly Tyr Val Thr Lys Asp Leu Glu Tyr Phe Pro Glu Thr
                1205                1210                1215

GAT AAG GTA TGG ATT GAG ATC GGA GAA ACA GAA GGA ACA TTC ATC GTG      3696
Asp Lys Val Trp Ile Glu Ile Gly Glu Thr Glu Gly Thr Phe Ile Val
            1220                1225                1230

GAT AGC GTG GAA TTA CTC CTT ATG GAG GAA                              3726
Asp Ser Val Glu Leu Leu Leu Met Glu Glu
        1235                1240

(2) INFORMATION FOR SEQ ID NO: 12:

(i) SEQUENCE CHARACTERISTICS:
        (A) LENGTH: 1242 amino acids
        (B) TYPE: amino acid
        (D) TOPOLOGY: linear (ii) MOLECULE TYPE: protein (xi) SEQUENCE DESCRIPTION: SEQ ID NO: 12:

Met Asn Gln Asn Lys His Gly Ile Ile Gly Ala Ser Asn Cys Gly Cys
 1               5                  10                  15

Ala Ser Asp Asp Val Ala Lys Tyr Pro Leu Ala Asn Asn Pro Tyr Ser
                20                  25                  30

Ser Ala Leu Asn Leu Asn Ser Cys Gln Asn Ser Ser Ile Leu Asn Trp
            35                  40                  45

Ile Asn Ile Ile Gly Asp Ala Ala Lys Glu Ala Val Ser Ile Gly Thr
        50                  55                  60

Thr Ile Val Ser Leu Ile Thr Ala Pro Ser Leu Thr Gly Leu Ile Ser
65                  70                  75                  80

Ile Val Tyr Asp Leu Ile Gly Lys Val Leu Gly Gly Ser Ser Gly Gln
                85                  90                  95

Ser Ile Ser Asp Leu Ser Ile Cys Asp Leu Leu Ser Ile Ile Asp Leu
            100                 105                 110

Arg Val Ser Gln Ser Val Leu Asn Asp Gly Ile Ala Asp Phe Asn Gly
```

-continued

```
           115                 120                 125
Ser Val Leu Leu Tyr Arg Asn Tyr Leu Glu Ala Leu Asp Ser Trp Asn
       130                 135                 140
Lys Asn Pro Asn Ser Ala Ser Ala Glu Glu Leu Arg Thr Arg Phe Arg
145                 150                 155                 160
Ile Ala Asp Ser Glu Phe Asp Arg Ile Leu Thr Arg Gly Ser Leu Thr
                165                 170                 175
Asn Gly Gly Ser Leu Ala Arg Gln Asn Ala Gln Ile Leu Leu Leu Pro
                180                 185                 190
Ser Phe Ala Ser Ala Ala Phe His Leu Leu Leu Leu Arg Asp Ala
        195                 200                 205
Thr Arg Tyr Gly Thr Asn Trp Gly Leu Tyr Asn Ala Thr Pro Phe Ile
        210                 215                 220
Asn Tyr Gln Ser Lys Leu Val Glu Leu Ile Glu Leu Tyr Thr Asp Tyr
225                 230                 235                 240
Cys Val His Trp Tyr Asn Arg Gly Phe Asn Glu Leu Arg Gln Arg Gly
                245                 250                 255
Thr Ser Ala Thr Ala Trp Leu Glu Phe His Arg Tyr Arg Arg Glu Met
                260                 265                 270
Thr Leu Met Val Leu Asp Ile Val Ala Ser Phe Ser Ser Leu Asp Ile
        275                 280                 285
Thr Asn Tyr Pro Ile Glu Thr Asp Phe Gln Leu Ser Arg Val Ile Tyr
        290                 295                 300
Thr Asp Pro Ile Gly Phe Val His Arg Ser Leu Arg Gly Glu Ser
305                 310                 315                 320
Trp Phe Ser Phe Val Asn Arg Ala Asn Phe Ser Asp Leu Glu Asn Ala
                325                 330                 335
Ile Pro Asn Pro Arg Pro Ser Trp Phe Leu Asn Asn Met Ile Ile Ser
                340                 345                 350
Thr Gly Ser Leu Thr Leu Pro Val Ser Pro Ser Thr Asp Arg Ala Arg
        355                 360                 365
Val Trp Tyr Gly Ser Arg Asp Arg Ile Ser Pro Ala Asn Ser Gln Phe
        370                 375                 380
Ile Thr Glu Leu Ile Ser Gly Gln His Thr Thr Ala Thr Gln Thr Ile
385                 390                 395                 400
Leu Gly Arg Asn Ile Phe Arg Val Asp Ser Gln Ala Cys Asn Leu Asn
                405                 410                 415
Asp Thr Thr Tyr Gly Val Asn Arg Ala Val Phe Tyr His Asp Ala Ser
                420                 425                 430
Glu Gly Ser Gln Arg Ser Val Tyr Glu Gly Tyr Ile Arg Thr Thr Gly
        435                 440                 445
Ile Asp Asn Pro Arg Val Gln Asn Ile Asn Thr Tyr Leu Pro Gly Glu
450                 455                 460
Asn Ser Asp Ile Pro Thr Pro Glu Asp Tyr Thr His Ile Leu Ser Thr
465                 470                 475                 480
Thr Ile Asn Leu Thr Gly Gly Leu Arg Gln Val Ala Ser Asn Arg Arg
                485                 490                 495
Ser Ser Leu Val Met Tyr Gly Trp Thr His Lys Ser Leu Ala Arg Asn
                500                 505                 510
Asn Thr Ile Asn Pro Asp Arg Ile Thr Gln Ile Pro Leu Val Lys Gly
        515                 520                 525
Phe Arg Val Trp Gly Gly Thr Ser Val Ile Thr Gly Pro Gly Phe Thr
        530                 535                 540
```

```
Gly Gly Asp Ile Leu Arg Arg Asn Thr Phe Gly Asp Phe Val Ser Leu
545                 550                 555                 560

Gln Val Asn Ile Asn Ser Pro Ile Thr Gln Arg Tyr Arg Leu Arg Phe
                565                 570                 575

Arg Tyr Ala Ser Ser Arg Asp Ala Arg Val Ile Val Leu Thr Gly Ala
            580                 585                 590

Ala Ser Thr Gly Val Gly Gly Gln Val Ser Val Asn Met Pro Leu Gln
        595                 600                 605

Lys Thr Met Glu Ile Gly Glu Asn Leu Thr Ser Arg Thr Phe Arg Tyr
    610                 615                 620

Thr Asp Phe Ser Asn Pro Phe Ser Phe Arg Ala Asn Pro Asp Ile Ile
625                 630                 635                 640

Gly Ile Ser Glu Gln Pro Leu Phe Gly Ala Gly Ser Ile Ser Ser Gly
                645                 650                 655

Glu Leu Tyr Ile Asp Lys Ile Glu Ile Ile Leu Ala Asp Ala Thr Phe
            660                 665                 670

Glu Ala Glu Ser Asp Leu Glu Arg Ala Gln Lys Ala Val Asn Ala Leu
        675                 680                 685

Phe Thr Ser Ser Asn Gln Ile Gly Leu Lys Thr Asp Val Thr Asp Tyr
690                 695                 700

His Ile Asp Gln Val Ser Asn Leu Val Asp Cys Leu Ser Asp Glu Phe
705                 710                 715                 720

Cys Leu Asp Glu Lys Arg Glu Leu Ser Glu Lys Val Lys His Ala Lys
                725                 730                 735

Arg Leu Ser Asp Glu Arg Asn Leu Leu Gln Asp Pro Asn Phe Arg Gly
            740                 745                 750

Ile Asn Arg Gln Pro Asp Arg Gly Trp Arg Gly Ser Thr Asp Ile Thr
        755                 760                 765

Ile Gln Gly Gly Asp Asp Val Phe Lys Glu Asn Tyr Val Thr Leu Pro
770                 775                 780

Gly Thr Val Asp Glu Cys Tyr Pro Thr Tyr Leu Tyr Gln Lys Ile Asp
785                 790                 795                 800

Glu Ser Lys Leu Lys Ala Tyr Thr Arg Tyr Glu Leu Arg Gly Tyr Ile
                805                 810                 815

Glu Asp Ser Gln Asp Leu Glu Ile Tyr Leu Ile Arg Tyr Asn Ala Lys
            820                 825                 830

His Glu Ile Val Asn Val Pro Gly Thr Gly Ser Leu Trp Pro Leu Ser
        835                 840                 845

Ala Gln Ser Pro Ile Gly Lys Cys Gly Glu Pro Asn Arg Cys Ala Pro
850                 855                 860

His Leu Glu Trp Asn Pro Asp Leu Asp Cys Ser Cys Arg Asp Gly Glu
865                 870                 875                 880

Lys Cys Ala His His Ser His His Phe Thr Leu Asp Ile Asp Val Gly
                885                 890                 895

Cys Thr Asp Leu Asn Glu Asp Leu Gly Val Trp Val Ile Phe Lys Ile
            900                 905                 910

Lys Thr Gln Asp Gly His Ala Arg Leu Gly Asn Leu Glu Phe Leu Glu
        915                 920                 925

Glu Lys Pro Leu Leu Gly Glu Ala Leu Ala Arg Val Lys Arg Ala Glu
930                 935                 940

Lys Lys Trp Arg Asp Lys Arg Glu Lys Leu Gln Leu Glu Thr Asn Ile
945                 950                 955                 960
```

-continued

```
Val Tyr Lys Glu Ala Lys Glu Ser Val Asp Ala Leu Phe Val Asn Ser
            965                 970                 975
Gln Tyr Asp Arg Leu Gln Val Asp Thr Asn Ile Ala Met Ile His Ala
        980                 985                 990
Ala Asp Lys Arg Val His Arg Ile Arg Glu Ala Tyr Leu Pro Glu Leu
    995                 1000                1005
Ser Val Ile Pro Gly Val Asn Ala Ala Ile Phe Glu Glu Leu Glu Gly
    1010                1015                1020
Arg Ile Phe Thr Ala Tyr Ser Leu Tyr Asp Ala Arg Asn Val Ile Lys
1025                1030                1035                1040
Asn Gly Asp Phe Asn Asn Gly Leu Leu Cys Trp Asn Val Lys Gly His
                1045                1050                1055
Val Asp Val Glu Glu Gln Asn Asn His Arg Ser Val Leu Val Ile Pro
            1060                1065                1070
Glu Trp Glu Ala Glu Val Ser Gln Glu Val Arg Val Cys Pro Gly Arg
        1075                1080                1085
Gly Tyr Ile Leu Arg Val Thr Ala Tyr Lys Glu Gly Tyr Gly Glu Gly
    1090                1095                1100
Cys Val Thr Ile His Glu Ile Glu Asp Asn Thr Asp Glu Leu Lys Phe
1105                1110                1115                1120
Ser Asn Cys Val Glu Glu Glu Val Tyr Pro Asn Asn Thr Val Thr Cys
                1125                1130                1135
Asn Asn Tyr Thr Gly Thr Gln Glu Glu Tyr Glu Gly Thr Tyr Thr Ser
            1140                1145                1150
Arg Asn Gln Gly Tyr Asp Glu Ala Tyr Gly Asn Asn Pro Ser Val Pro
        1155                1160                1165
Ala Asp Tyr Ala Ser Val Tyr Glu Glu Lys Ser Tyr Thr Asp Gly Arg
    1170                1175                1180
Arg Glu Asn Pro Cys Glu Ser Asn Arg Gly Tyr Gly Asp Tyr Thr Pro
1185                1190                1195                1200
Leu Pro Ala Gly Tyr Val Thr Lys Asp Leu Glu Tyr Phe Pro Glu Thr
                1205                1210                1215
Asp Lys Val Trp Ile Glu Ile Gly Glu Thr Glu Gly Thr Phe Ile Val
            1220                1225                1230
Asp Ser Val Glu Leu Leu Leu Met Glu Glu
        1235                1240
```

(2) INFORMATION FOR SEQ ID NO: 13:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "BglII site downstream of (xi) SEQUENCE DESCRIPTION: SEQ ID NO: 13:

ATAAGATCTG TT                                        12

(2) INFORMATION FOR SEQ ID NO: 14:

(i) SEQUENCE CHARACTERISTICS:
        (A) LENGTH: 35 base pairs
        (B) TYPE: nucleic acid
        (C) STRANDEDNESS: single
        (D) TOPOLOGY: linear -continued

```
    (ii) MOLECULE TYPE: other nucleic acid
         (A) DESCRIPTION: /desc = "primer"

(xi) SEQUENCE DESCRIPTION: SEQ ID NO: 14:

GCTAGCCATG GATCAAAATA AACACGGAAT TATTG                                35

(2) INFORMATION FOR SEQ ID NO: 15:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "primer"

(xi) SEQUENCE DESCRIPTION: SEQ ID NO: 15:

CTGGTCAGAT CTTTGAAGTA GAGCTCC                                         27
```

What is claimed is:

1. An isolated DNA molecule encoding a polypeptide comprising an insecticidal *Bacillus thuringiensis* hybrid toxin fragment, comprising:
   a) at a C-terminus of said fragment, domain III of a first Cry protein; and
   b) at an N-terminus of said fragment, domains I and II of a second Cry protein different from the first Cry protein.

2. An isolated DNA molecule according to claim 1, wherein said hybrid toxin fragment binds to a binding site in an insect gut that is different than the site bound by said first Cry protein.

3. An isolated DNA molecule according to claim 1, which further encodes a protein having at least one of the following properties: herbicide resistance, plant growth-promoting, anti-fungal, anti-bacterial, anti-viral, and anti-nematode properties.

4. An isolated DNA molecule according to claim 1, which is modified to optimize expression in a heterologous host, said modifications selected from the group consisting of codon optimization for the intended host and removal of known mRNA instability motifs or polyadenylation signals.

5. An isolated DNA molecule that is complementary to the DNA molecule of claim 1.

6. A recombinant vector comprising the DNA molecule of claim 1.

7. An isolated cell transformed with the DNA molecule of claim 1.

8. A plant transformed with the DNA molecule of claim 1, wherein the progeny of such plant contains the DNA molecule stably incorporated and heritable in a Mendelian manner.

9. Seeds of the plant of claim 8.

10. A method of producing a protein, comprising expressing the DNA molecule of claim 1.

11. An insecticidal composition comprising the isolated cell of claim 7.

12. A process for controlling insects, comprising exposing them to the insecticidal composition of claim 11.

13. An isolated DNA molecule according to claim 1, wherein said first Cry protein is CryIC.

14. An isolated DNA molecule according to claim 1, wherein said second Cry protein is selected from the group consisting of CryIA, CryIE, and CryIG.

15. An isolated DNA molecule according to claim 14, wherein said second Cry protein is CryIA.

16. An isolated DNA molecule according to claim 14, wherein said second Cry protein is CryIE.

17. An isolated DNA molecule according to claim 14, wherein said second Cry protein is cryIG.

18. An isolated DNA molecule according to claim 1, wherein said first Cry protein is CryIC, and wherein said second Cry protein is CryIA, CryIE, or CryIG.

19. An isolated DNA molecule according to claim 1, wherein said C-terminus comprises the sequence from amino acid position 454 to position 602 of SEQ ID NO:2.

20. An isolated DNA molecule according to claim 1, wherein said C-terminus comprises the sequence from amino acid position 478 to position 602 of SEQ ID NO:2.

21. An isolated DNA molecule according to claim 1, wherein said insecticidal *Bacillus thuringiensis* hybrid toxin fragment comprises an amino acid sequence at least 90% similar to amino acids 1–620 of SEQ ID NO:6.

22. An isolated DNA molecule according to claim 1, wherein said insecticidal *Bacillus thuringiensis* hybrid toxin fragment comprises an amino acid sequence at least 90% similar to amino acids 1–627 of SEQ ID NO:8.

23. An isolated DNA molecule according to claim 1, wherein said insecticidal *Bacillus thuringiensis* hybrid toxin fragment comprises an amino acid sequence at least 90% similar to amino acids 1–602 of SEQ ID NO:12.

24. An isolated DNA molecule according to claim 1, comprising a nucleotide sequence that hybridizes to nucleotides 1–1860 of SEQ ID NO:5 under the following set of conditions: hybridization at 7% sodium dodecyl sulfate (SDS), 0.5 M $NaPO_4$ pH 7.0, 1 mM EDTA at 50° C.; wash with 2×SSC, 1% SDS, at 50° C.

25. An isolated DNA molecule according to claim 1, comprising a nucleotide sequence that hybridizes to nucleotides 1–1881 of SEQ ID NO:7 under the following set of conditions: hybridization at 7% sodium dodecyl sulfate (SDS), 0.5 M $NaPO_4$ pH 7.0, 1 mM EDTA at 50° C.; wash with 2×SSC, 1% SDS, at 50° C.

26. An isolated DNA molecule according to claim 1, comprising a nucleotide sequence that hybridizes to nucleotides 1–1806 of SEQ ID NO:11 under the following set of conditions: hybridization at 7% sodium dodecyl sulfate (SDS), 0.5 M $NaPO_4$ pH 7.0, 1 mM EDTA at 50° C.; wash with 2×SSC, 1% SDS, at 50° C.

27. An isolated DNA molecule according to claim 1, comprising a nucleotide sequence that is at least 90% identical to nucleotides 1–1860 of SEQ ID NO:5.

28. An isolated DNA molecule according to claim 1, comprising a nucleotide sequence that is at least 90% identical to nucleotides 1–1881 of SEQ ID NO:7.

29. An isolated DNA molecule according to claim 1, comprising a nucleotide sequence that is at least 90% identical to nucleotides 1–1806 of SEQ ID NO:11.

* * * * *